(12) United States Patent
Borchert et al.

(10) Patent No.: US 9,994,838 B2
(45) Date of Patent: Jun. 12, 2018

(54) POLYPEPTIDES HAVING PROTEASE ACTIVITY AND POLYNUCLEOTIDES ENCODING SAME

(71) Applicant: Novozymes A/S, Bagsvaerd (DK)

(72) Inventors: Martin Simon Borchert, Hilleroed (DK); Jeppe Wegener Tams, Gentofte (DK)

(73) Assignee: Novozymes A/S, Bagsvaerd (DK)

( * ) Notice: Subject to any disclaimer, the term of this patent is extended or adjusted under 35 U.S.C. 154(b) by 0 days. days.

(21) Appl. No.: 15/461,710

(22) Filed: Mar. 17, 2017

(65) Prior Publication Data

US 2017/0204392 A1    Jul. 20, 2017

Related U.S. Application Data

(63) Continuation of application No. 14/125,645, filed as application No. PCT/EP2012/062144 on Jun. 22, 2012.

(60) Provisional application No. 61/501,319, filed on Jun. 27, 2011.

(30) Foreign Application Priority Data

Jun. 24, 2011 (EP) ...................................... 11171317

(51) Int. Cl.
*C12N 9/54* (2006.01)
*C11D 3/386* (2006.01)

(52) U.S. Cl.
CPC ................ *C12N 9/54* (2013.01); *C11D 3/386* (2013.01); *C12Y 304/21* (2013.01)

(58) Field of Classification Search
None
See application file for complete search history.

(56) References Cited

PUBLICATIONS

Anonymous, MEROPS Peptidase Database (2011).
Be'er et al., EMBL Accession No. GQ891986 (2009).
Be'er et al., PNAS, vol. 107, No. 14, pp. 6258-6263 (2010).
Bernard et al., Current Protocols in Protein Science, unit 5.3, sections 5.3.1-5.3.18 (1995).
Foophow et al., Protein Engineering, Design & Selection, vol. 23, No. 5, pp. 347-355 (2010).
Goddette et al., J. Mol. Biol., vol. 228, No. 2, pp. 580-595 (1992).
Goddette et al., Alignment of SID2 and P29599 (1992).
Jones et al., UniProt Accession No. H3WMP5 (2012).
Page et al., Cellular and Molecular Life Sciences, vol. 65, Nos. 7-8, pp. 1220-1236 (2008).
Seizen et el., Protein Science, vol. 6, No. 3, pp. 501-523 (1997).
Strauss et al., Current Protocols in Molecular Biology, unit 63, sections 63.1-63.6 (1993).

*Primary Examiner* — Sheridan Swope
(74) *Attorney, Agent, or Firm* — David Fazzolare

(57) ABSTRACT

The present invention relates to isolated polypeptides having protease activity and isolated polynucleotides encoding the polypeptides. The invention also relates to nucleic acid constructs, vectors, and host cells comprising the polynucleotides as well as methods of producing and using the polypeptides.

20 Claims, No Drawings

SEQUENCE LISTING

```
<160> NUMBER OF SEQ ID NOS: 52

<210> SEQ ID NO 1
<211> LENGTH: 2100
<212> TYPE: DNA
<213> ORGANISM: Bacillus sp.
<220> FEATURE:
<221> NAME/KEY: CDS
<222> LOCATION: (204)..(1847)
<220> FEATURE:
<221> NAME/KEY: sig_peptide
<222> LOCATION: (204)..(281)
<220> FEATURE:
<221> NAME/KEY: mat_peptide
<222> LOCATION: (711)..(1535)

<400> SEQUENCE: 1
tactaggttt ttatattcac tcattctttg ttagtcttga aaacagaagc tcctatcaga      60
gcagtcatca ttttatagga agggctgtga ttatcgtgaa agactatcag aaaattgata     120
gctagataat tagtgaagtt tcaaaaaagg aaagggcgta tgttcactca agtctaacga     180
taaaaatatt gggaggaaac aca atg aaa aag act ctt ggc ttg tca ttt        230
                         Met Lys Lys Thr Leu Gly Leu Ser Phe
                                     -165 ttg atg ctt gta atg ttc att tcc atg ttt tct atc aac acc cta           275
Leu Met Leu Val Met Phe Ile Ser Met Phe Ser Ile Asn Thr Leu
-160                 -155                 -150 gca agt gat gat atg aag aaa gaa gac tat att gaa ggt cag tta           320
Ala Ser Asp Asp Met Lys Lys Glu Asp Tyr Ile Glu Gly Gln Leu
-145                 -140                 -135 atc gtt tct gtg gaa gga aaa gta aaa gaa aaa gca aaa aat gtt           365
Ile Val Ser Val Glu Gly Lys Val Lys Glu Lys Ala Lys Asn Val
-130                 -125                 -120 tcc tta att caa gaa atg aac agt gta agt gac tta cta ttt gac           410
Ser Leu Ile Gln Glu Met Asn Ser Val Ser Asp Leu Leu Phe Asp
-115                 -110                 -105 aat gca aac ttg aat aaa aaa ggc ttt aaa ttt gtg gat tct tta ctt       458
Asn Ala Asn Leu Asn Lys Lys Gly Phe Lys Phe Val Asp Ser Leu Leu
-100                  -95                  -90                  -85 gaa gga aaa gat gcc aat tct gtt gca ttg ttt gat aac aaa ttc aaa       506
Glu Gly Lys Asp Ala Asn Ser Val Ala Leu Phe Asp Asn Lys Phe Lys
                  -80                  -75                  -70 gaa aaa gct gca aaa aag atg gga tat gta tac ctt gta gaa tat tct       554
Glu Lys Ala Ala Lys Lys Met Gly Tyr Val Tyr Leu Val Glu Tyr Ser
                  -65                  -60                  -55
```

| | | | | | | | | | | | | | | | | |
|---|---|---|---|---|---|---|---|---|---|---|---|---|---|---|---|---|
| aca | gag | gat | tat | gaa | tct | att | gat | gcg | gca | aag | aaa | gaa | ctt | aaa | aag | 602 |
| Thr | Glu | Asp | Tyr | Glu | Ser | Ile | Asp | Ala | Ala | Lys | Lys | Glu | Leu | Lys | Lys | |
| | | | | -50 | | | | -45 | | | | -40 | | | | |
| cta | tta | aag | gaa | ctt | gat | tta | aaa | gtt | aaa | gat | gtg | act | gaa | aac | ttt | 650 |
| Leu | Leu | Lys | Glu | Leu | Asp | Leu | Lys | Val | Lys | Asp | Val | Thr | Glu | Asn | Phe | |
| | -35 | | | | -30 | | | | | -25 | | | | | | |
| aca | atg | cat | tta | tta | gaa | gat | gga | gcc | gca | aca | gct | tca | gca | act | gaa | 698 |
| Thr | Met | His | Leu | Leu | Glu | Asp | Gly | Ala | Ala | Thr | Ala | Ser | Ala | Thr | Glu | |
| -20 | | | | | -15 | | | | | -10 | | | | | -5 | |
| ata | gca | cca | tta | atg | cac | aac | aat | caa | cgt | tgg | cat | tat | gaa | atg | att | 746 |
| Ile | Ala | Pro | Leu | Met | His | Asn | Asn | Gln | Arg | Trp | His | Tyr | Glu | Met | Ile | |
| | | | -1 | 1 | | | | 5 | | | | | | 10 | | |
| aac | gca | cct | caa | gca | tgg | gga | att | aca | act | gga | agc | agt | aat | gta | aga | 794 |
| Asn | Ala | Pro | Gln | Ala | Trp | Gly | Ile | Thr | Thr | Gly | Ser | Ser | Asn | Val | Arg | |
| | | 15 | | | | | 20 | | | | | 25 | | | | |
| att | gcc | gtc | tta | gac | aca | ggt | att | gat | gct | aac | cat | cca | aac | tta | cgt | 842 |
| Ile | Ala | Val | Leu | Asp | Thr | Gly | Ile | Asp | Ala | Asn | His | Pro | Asn | Leu | Arg | |
| | 30 | | | | | 35 | | | | | 40 | | | | | |
| aat | cta | gtt | gat | aca | agt | ctt | ggt | aga | agc | ttt | gtt | gga | ggc | gga | aca | 890 |
| Asn | Leu | Val | Asp | Thr | Ser | Leu | Gly | Arg | Ser | Phe | Val | Gly | Gly | Gly | Thr | |
| 45 | | | | | 50 | | | | | 55 | | | | | 60 | |
| gga | gat | gtg | caa | ggt | cac | gga | acg | cat | gtt | gca | ggg | aca | att | gcc | agt | 938 |
| Gly | Asp | Val | Gln | Gly | His | Gly | Thr | His | Val | Ala | Gly | Thr | Ile | Ala | Ser | |
| | | | | 65 | | | | | 70 | | | | | 75 | | |
| tat | ggt | tcc | gtg | tct | ggt | gtc | atg | caa | aat | gct | cgc | ctt | att | cct | gta | 986 |
| Tyr | Gly | Ser | Val | Ser | Gly | Val | Met | Gln | Asn | Ala | Arg | Leu | Ile | Pro | Val | |
| | | 80 | | | | | 85 | | | | | 90 | | | | |
| aaa | gta | tta | ggg | gac | aac | gga | agt | ggc | agt | atg | tat | ggg | atc | caa | caa | 1034 |
| Lys | Val | Leu | Gly | Asp | Asn | Gly | Ser | Gly | Ser | Met | Tyr | Gly | Ile | Gln | Gln | |
| | | 95 | | | | | 100 | | | | | 105 | | | | |
| gga | att | ctc | tac | gct | gct | agt | att | aac | gcg | gat | gta | ata | aat | atg | tca | 1082 |
| Gly | Ile | Leu | Tyr | Ala | Ala | Ser | Ile | Asn | Ala | Asp | Val | Ile | Asn | Met | Ser | |
| | 110 | | | | | 115 | | | | | 120 | | | | | |
| cta | ggt | ggc | ggt | ggt | tat | gat | tct | gga | atg | aac | aat | gcc | att | aat | act | 1130 |
| Leu | Gly | Gly | Gly | Gly | Tyr | Asp | Ser | Gly | Met | Asn | Asn | Ala | Ile | Asn | Thr | |
| 125 | | | | | 130 | | | | | 135 | | | | | 140 | |
| gct | gtt | agt | tct | ggt | act | ctc | gta | att | gct | gct | tct | ggg | aat | gat | gga | 1178 |
| Ala | Val | Ser | Ser | Gly | Thr | Leu | Val | Ile | Ala | Ala | Ser | Gly | Asn | Asp | Gly | |
| | | | | 145 | | | | | 150 | | | | | 155 | | |
| aga | gga | agt | att | tct | tat | ccg | gct | gct | tat | agt | aat | gct | att | gca | gtg | 1226 |
| Arg | Gly | Ser | Ile | Ser | Tyr | Pro | Ala | Ala | Tyr | Ser | Asn | Ala | Ile | Ala | Val | |
| | | | 160 | | | | | 165 | | | | | 170 | | | |
| ggt | tct | gta | aca | tcg | aat | aga | act | aga | tcc | aac | ttc | tca | aat | tat | ggt | 1274 |
| Gly | Ser | Val | Thr | Ser | Asn | Arg | Thr | Arg | Ser | Asn | Phe | Ser | Asn | Tyr | Gly | |
| | | 175 | | | | | 180 | | | | | 185 | | | | |
| agc | gga | tta | gaa | cta | atg | gcc | cca | gga | tca | aat | att | tat | agt | act | tat | 1322 |
| Ser | Gly | Leu | Glu | Leu | Met | Ala | Pro | Gly | Ser | Asn | Ile | Tyr | Ser | Thr | Tyr | |
| | | 190 | | | | | 195 | | | | | 200 | | | | |
| ccg | aat | ggt | caa | ttc | cgt | aca | tta | tca | ggt | aca | tct | atg | gcc | aca | cca | 1370 |
| Pro | Asn | Gly | Gln | Phe | Arg | Thr | Leu | Ser | Gly | Thr | Ser | Met | Ala | Thr | Pro | |
| 205 | | | | | 210 | | | | | 215 | | | | | 220 | |
| cac | gta | gct | ggg | gtt | gca | ggt | tta | att | aaa | tca | gca | aat | cca | aat | cta | 1418 |
| His | Val | Ala | Gly | Val | Ala | Gly | Leu | Ile | Lys | Ser | Ala | Asn | Pro | Asn | Leu | |
| | | | | 225 | | | | | 230 | | | | | 235 | | |
| tca | gtc | aca | caa | gtt | aga | aat | atc | cta | aga | gat | act | gcg | cag | tat | gca | 1466 |
| Ser | Val | Thr | Gln | Val | Arg | Asn | Ile | Leu | Arg | Asp | Thr | Ala | Gln | Tyr | Ala | |
| | | | 240 | | | | | 245 | | | | | 250 | | | |
| gga | agt | tct | aac | caa | tat | gga | tat | gga | att | gtt | aat | gct | tat | gcg | gca | 1514 |
| Gly | Ser | Ser | Asn | Gln | Tyr | Gly | Tyr | Gly | Ile | Val | Asn | Ala | Tyr | Ala | Ala | |
| | | 255 | | | | | 260 | | | | | 265 | | | | |

-continued

```
gtt caa gct gct ggt ggg gga gcg gta agt tat gaa act aat aca tcc    1562
Val Gln Ala Ala Gly Gly Gly Ala Val Ser Tyr Glu Thr Asn Thr Ser
        270                 275                 280 gtt tct aca aat caa agt acc tac tat aga ggg aat aac gtg aca atg    1610
Val Ser Thr Asn Gln Ser Thr Tyr Tyr Arg Gly Asn Asn Val Thr Met
285                 290                 295                 300 acg gct atc gtc act gac caa aac aat agt aga ttg caa ggg gca act    1658
Thr Ala Ile Val Thr Asp Gln Asn Asn Ser Arg Leu Gln Gly Ala Thr
                305                 310                 315 gta aac ttt aca att act cgt ccg aac ggt acc aca gtt aca aat gct    1706
Val Asn Phe Thr Ile Thr Arg Pro Asn Gly Thr Thr Val Thr Asn Ala
            320                 325                 330 aca acg aca aat tca tct ggt gtt gcg aca tgg acc att gga tcc aac    1754
Thr Thr Thr Asn Ser Ser Gly Val Ala Thr Trp Thr Ile Gly Ser Asn
        335                 340                 345 tca tcc aca gct gtg ggg acg tat caa gtt cgt gca caa aca acg tat    1802
Ser Ser Thr Ala Val Gly Thr Tyr Gln Val Arg Ala Gln Thr Thr Tyr
    350                 355                 360 ccg aat tat caa tct agc tca gca aca aca tct ttt cga tta caa        1847
Pro Asn Tyr Gln Ser Ser Ser Ala Thr Thr Ser Phe Arg Leu Gln
365                 370                 375 taaatcgtaa atctagtgaa gtattccttt acctttatta actacccct tttaaaatag   1907 tacgtgtatg tacgaccgaa tgccccgagc gttcggtctt ttttttactg gtttaaaat   1967 gaagtataag gtatcaaaca ttagcaaacg taaaaaatac aagctgtatt ctaaaaattt  2027 gttattttc aggaagctta taaacttgga acgttacagg tggatgcttt ccgcgggcag   2087
catcagcctc ctc                                                     2100

<210> SEQ ID NO 2
<211> LENGTH: 548
<212> TYPE: PRT
<213> ORGANISM: Bacillus sp.

<400> SEQUENCE: 2

Met Lys Lys Thr Leu Gly Leu Ser Phe Leu Met Leu Val Met Phe
                -165                -160                -155

Ile Ser Met Phe Ser  Ile Asn Thr Leu Ala  Ser Asp Asp Met Lys
                -150                -145                -140

Lys Glu Asp Tyr Ile  Glu Gly Gln Leu Ile  Val Ser Val Glu Gly
                -135                -130                -125

Lys Val Lys Glu Lys  Ala Lys Asn Val Ser  Leu Ile Gln Glu Met
                -120                -115                -110

Asn Ser Val Ser Asp  Leu Leu Phe Asp Asn  Ala Asn Leu Asn Lys Lys
                -105                -100                 -95

Gly Phe Lys Phe Val Asp Ser Leu Leu Glu Gly Lys Asp Ala Asn Ser
            -90                 -85                 -80

Val Ala Leu Phe Asp Asn Lys Phe Lys Glu Lys Ala Ala Lys Lys Met
        -75                 -70                 -65

Gly Tyr Val Tyr Leu Val Glu Tyr Ser Thr Glu Asp Tyr Glu Ser Ile
    -60                 -55                 -50

Asp Ala Ala Lys Lys Glu Leu Lys Lys Leu Leu Lys Glu Leu Asp Leu
-45                 -40                 -35                 -30

Lys Val Lys Asp Val Thr Glu Asn Phe Thr Met His Leu Leu Glu Asp
                -25                 -20                 -15

Gly Ala Ala Thr Ala Ser Ala Thr Glu Ile Ala Pro Leu Met His Asn
            -10                 -5                 -1   1
```

Asn Gln Arg Trp His Tyr Glu Met Ile Asn Ala Pro Gln Ala Trp Gly
    5                   10                  15

Ile Thr Thr Gly Ser Ser Asn Val Arg Ile Ala Val Leu Asp Thr Gly
 20              25                  30                  35

Ile Asp Ala Asn His Pro Asn Leu Arg Asn Leu Val Asp Thr Ser Leu
                 40                  45                  50

Gly Arg Ser Phe Val Gly Gly Thr Gly Asp Val Gln Gly His Gly
             55                  60                  65

Thr His Val Ala Gly Thr Ile Ala Ser Tyr Gly Ser Val Ser Gly Val
         70                  75                  80

Met Gln Asn Ala Arg Leu Ile Pro Val Lys Val Leu Gly Asp Asn Gly
 85                  90                  95

Ser Gly Ser Met Tyr Gly Ile Gln Gln Gly Ile Leu Tyr Ala Ala Ser
100                 105                 110                 115

Ile Asn Ala Asp Val Ile Asn Met Ser Leu Gly Gly Gly Gly Tyr Asp
                120                 125                 130

Ser Gly Met Asn Asn Ala Ile Asn Thr Ala Val Ser Ser Gly Thr Leu
            135                 140                 145

Val Ile Ala Ala Ser Gly Asn Asp Gly Arg Gly Ser Ile Ser Tyr Pro
150                 155                 160

Ala Ala Tyr Ser Asn Ala Ile Ala Val Gly Ser Val Thr Ser Asn Arg
165                 170                 175

Thr Arg Ser Asn Phe Ser Asn Tyr Gly Ser Gly Leu Glu Leu Met Ala
180                 185                 190                 195

Pro Gly Ser Asn Ile Tyr Ser Thr Tyr Pro Asn Gly Gln Phe Arg Thr
                200                 205                 210

Leu Ser Gly Thr Ser Met Ala Thr Pro His Val Ala Gly Val Ala Gly
            215                 220                 225

Leu Ile Lys Ser Ala Asn Pro Asn Leu Ser Val Thr Gln Val Arg Asn
        230                 235                 240

Ile Leu Arg Asp Thr Ala Gln Tyr Ala Gly Ser Ser Asn Gln Tyr Gly
245                 250                 255

Tyr Gly Ile Val Asn Ala Tyr Ala Ala Val Gln Ala Ala Gly Gly Gly
260                 265                 270                 275

Ala Val Ser Tyr Glu Thr Asn Thr Ser Val Ser Thr Asn Gln Ser Thr
                280                 285                 290

Tyr Tyr Arg Gly Asn Asn Val Thr Met Thr Ala Ile Val Thr Asp Gln
            295                 300                 305

Asn Asn Ser Arg Leu Gln Gly Ala Thr Val Asn Phe Thr Ile Thr Arg
        310                 315                 320

Pro Asn Gly Thr Thr Val Thr Asn Ala Thr Thr Asn Ser Ser Gly
325                 330                 335

Val Ala Thr Trp Thr Ile Gly Ser Asn Ser Thr Ala Val Gly Thr
340                 345                 350                 355

Tyr Gln Val Arg Ala Gln Thr Thr Tyr Pro Asn Tyr Gln Ser Ser Ser
                360                 365                 370

Ala Thr Thr Ser Phe Arg Leu Gln
            375

<210> SEQ ID NO 3
<211> LENGTH: 1823
<212> TYPE: DNA
<213> ORGANISM: Bacillus borgouniensis
<220> FEATURE:

```
<221> NAME/KEY: CDS
<222> LOCATION: (101)..(1723)
<220> FEATURE:
<221> NAME/KEY: sig_peptide
<222> LOCATION: (101)..(187)
<220> FEATURE:
<221> NAME/KEY: mat_peptide
<222> LOCATION: (581)..(1405)

<400> SEQUENCE: 3
tggaggtcag tctaaaaaag tagactaggt ttaatagtct atgaaaaatg tcggacatca      60
ctgcatttgc ataaatcaga atatttaaaa aataggagga atg aaa atg aaa aaa     115
                                              Met Lys Met Lys Lys
                                                      -160 tgg ttg ggg atg tct gca gtc gtg gtg ctc atg gtt ttc tct atg         160
Trp Leu Gly Met Ser Ala Val Val Val Leu Met Val Phe Ser Met
-155                -150                -145 ttc acg ggg gcc gga ttt gcg aat gaa tcg aaa ggt aaa aat aac         205
Phe Thr Gly Ala Gly Phe Ala Asn Glu Ser Lys Gly Lys Asn Asn
-140                -135                -130 ggt gat tat att gaa ggt caa ctt gtc att tcg atc gaa gac cag         250
Gly Asp Tyr Ile Glu Gly Gln Leu Val Ile Ser Ile Glu Asp Gln
-125                -120                -115 tca caa ttt tcc att caa gca aca aat aac atc att aac aaa gat         295
Ser Gln Phe Ser Ile Gln Ala Thr Asn Asn Ile Ile Asn Lys Asp
-110                -105                -100 gag gta tta gaa aat aac gga ttt gag att gta gat tcg cta tta gga     343
Glu Val Leu Glu Asn Asn Gly Phe Glu Ile Val Asp Ser Leu Leu Gly
-95                 -90                 -85                 -80 caa aac aat ccg aat gaa att caa gca tat aat cat gac ttt act gca     391
Gln Asn Asn Pro Asn Glu Ile Gln Ala Tyr Asn His Asp Phe Thr Ala
                -75                 -70                 -65 act gtt gta aat gaa atg ggt ctt gtt tat ttg gtt gaa tac gat gtg     439
Thr Val Val Asn Glu Met Gly Leu Val Tyr Leu Val Glu Tyr Asp Val
            -60                 -55                 -50 aat aaa tat aag tcg att gat aaa gca aaa aaa gaa ctt gaa aaa aca     487
Asn Lys Tyr Lys Ser Ile Asp Lys Ala Lys Lys Glu Leu Glu Lys Thr
        -45                 -40                 -35 atg aaa gac ctt gga tta gaa gtt cga tac gtg tct gag aac ttt gtt     535
Met Lys Asp Leu Gly Leu Glu Val Arg Tyr Val Ser Glu Asn Phe Val
    -30                 -25                 -20 atg cat gcg atg gaa gaa gta aca gct gaa gat gtt tcg att gcg atg     583
Met His Ala Met Glu Glu Val Thr Ala Glu Asp Val Ser Ile Ala Met
-15                 -10                 -5                  -1  1 cat aat aac caa aga tgg cat tat gaa atg att aat gct cca caa gca     631
His Asn Asn Gln Arg Trp His Tyr Glu Met Ile Asn Ala Pro Gln Ala
                5                   10                  15 tgg aat gta aca aca ggt tca aga aat gtc cga atc gct gtt ctt gat     679
Trp Asn Val Thr Thr Gly Ser Arg Asn Val Arg Ile Ala Val Leu Asp
            20                  25                  30 act ggt att gat gcg aac cat ccc aat ctt cgt aac cta gtc aat acg     727
Thr Gly Ile Asp Ala Asn His Pro Asn Leu Arg Asn Leu Val Asn Thr
        35                  40                  45 agt tta gga cgt agc ttc gtt ggt ggt gga aca gga gat gtg caa ggg     775
Ser Leu Gly Arg Ser Phe Val Gly Gly Gly Thr Gly Asp Val Gln Gly
50                  55                  60                  65 cat ggg aca cat gta gcc gga aca att gca agt tat ggc tca gtt tct     823
His Gly Thr His Val Ala Gly Thr Ile Ala Ser Tyr Gly Ser Val Ser
                70                  75                  80 ggt gtg atg caa aac gct act tta att ccg gtg aaa gta ttg gga gat     871
Gly Val Met Gln Asn Ala Thr Leu Ile Pro Val Lys Val Leu Gly Asp
```

```
                     85                      90                       95
aat ggt agt ggt tcg atg tat ggt att cag caa ggg att tta tat gca        919
Asn Gly Ser Gly Ser Met Tyr Gly Ile Gln Gln Gly Ile Leu Tyr Ala
            100                 105                 110 gcg agt gta aat tct gat gtt att aat atg tct tta ggt ggc ggc ggc        967
Ala Ser Val Asn Ser Asp Val Ile Asn Met Ser Leu Gly Gly Gly Gly
        115                 120                 125 tat agt caa ggg atg gat gat gcg att cgt aca gct gta tca tca ggc       1015
Tyr Ser Gln Gly Met Asp Asp Ala Ile Arg Thr Ala Val Ser Ser Gly
130                 135                 140                 145 tca atc gtt gtt gct gct tct gga aac gac tca cgt gga agt att tct       1063
Ser Ile Val Val Ala Ala Ser Gly Asn Asp Ser Arg Gly Ser Ile Ser
                150                 155                 160 tat cca gct gct tac agt ggt gca atc gct gtt ggt tca gtt act tca       1111
Tyr Pro Ala Ala Tyr Ser Gly Ala Ile Ala Val Gly Ser Val Thr Ser
            165                 170                 175 aac cga act aga tca agc ttt tct aac tat ggt caa gga tta gag cta       1159
Asn Arg Thr Arg Ser Ser Phe Ser Asn Tyr Gly Gln Gly Leu Glu Leu
        180                 185                 190 atg gca cca ggt tca aat att tat agc aca tat cca aat gga cag ttc       1207
Met Ala Pro Gly Ser Asn Ile Tyr Ser Thr Tyr Pro Asn Gly Gln Phe
195                 200                 205 cgc act tta tct gga aca tca atg gca aca cca cat gtt gca ggt gta       1255
Arg Thr Leu Ser Gly Thr Ser Met Ala Thr Pro His Val Ala Gly Val
210                 215                 220                 225 gca gga tta att cga gca gca aac cct aat att tca gta gca gaa gca       1303
Ala Gly Leu Ile Arg Ala Ala Asn Pro Asn Ile Ser Val Ala Glu Ala
                230                 235                 240 aga acg att ttg cga aat aca gca caa tat gct gga agt ttc aat cag       1351
Arg Thr Ile Leu Arg Asn Thr Ala Gln Tyr Ala Gly Ser Phe Asn Gln
            245                 250                 255 tat gga tac gga att gtc gat gca aat gct gca gtt cga gct gct cgt       1399
Tyr Gly Tyr Gly Ile Val Asp Ala Asn Ala Ala Val Arg Ala Ala Arg
        260                 265                 270 ggt caa acg caa caa cca aga tat gaa acg aat aca aca gtg tct aca       1447
Gly Gln Thr Gln Gln Pro Arg Tyr Glu Thr Asn Thr Thr Val Ser Thr
275                 280                 285 aat gca tca act tat aga aga ggc caa tct gta act gta aga gct gat       1495
Asn Ala Ser Thr Tyr Arg Arg Gly Gln Ser Val Thr Val Arg Ala Asp
290                 295                 300                 305 gtt gtt gac caa gat ggt cga gca cta gcg aat tca acc gtt caa ttt       1543
Val Val Asp Gln Asp Gly Arg Ala Leu Ala Asn Ser Thr Val Gln Phe
                310                 315                 320 aca att aca cgt cca aat gga aca aca gta aca aat aca gca aca acg       1591
Thr Ile Thr Arg Pro Asn Gly Thr Thr Val Thr Asn Thr Ala Thr Thr
            325                 330                 335 aat aat tca ggt gtt gct aca tgg acg att gcg aca tca tcg tct aca       1639
Asn Asn Ser Gly Val Ala Thr Trp Thr Ile Ala Thr Ser Ser Ser Thr
        340                 345                 350 gca aga ggc acg tat ggt gta caa gcc gca acg tct ctt tca ggt tat       1687
Ala Arg Gly Thr Tyr Gly Val Gln Ala Ala Thr Ser Leu Ser Gly Tyr
355                 360                 365 gaa gga agt aca gcg aca acg agc ttt gtc ata aac taaagtaaat           1733
Glu Gly Ser Thr Ala Thr Thr Ser Phe Val Ile Asn
370                 375                 380 caatatatga aaaagctgcc gatatttaca cggcagcttt ttttaaaaga taagaaagca     1793
aaaatgttgg tatagcaatg aagcgttgaa                                      1823
```

-continued

<210> SEQ ID NO 4
<211> LENGTH: 541
<212> TYPE: PRT
<213> ORGANISM: Bacillus borgouniensis

<400> SEQUENCE: 4

Met Lys Met Lys Lys Trp Leu Gly Met Ser Ala Val Val Val Leu
-160 -155 -150

Met Val Phe Ser Met Phe Thr Gly Ala Gly Phe Ala Asn Glu Ser
-145 -140 -135

Lys Gly Lys Asn Asn Gly Asp Tyr Ile Glu Gly Gln Leu Val Ile
-130 -125 -120

Ser Ile Glu Asp Gln Ser Gln Phe Ser Ile Gln Ala Thr Asn Asn
-115 -110 -105

Ile Ile Asn Lys Asp Glu Val Leu Glu Asn Asn Gly Phe Glu Ile Val
-100 -95 -90 -85

Asp Ser Leu Leu Gly Gln Asn Asn Pro Asn Glu Ile Gln Ala Tyr Asn
-80 -75 -70

His Asp Phe Thr Ala Thr Val Val Asn Glu Met Gly Leu Val Tyr Leu
-65 -60 -55

Val Glu Tyr Asp Val Asn Lys Tyr Lys Ser Ile Asp Lys Ala Lys Lys
-50 -45 -40

Glu Leu Glu Lys Thr Met Lys Asp Leu Gly Leu Glu Val Arg Tyr Val
-35 -30 -25

Ser Glu Asn Phe Val Met His Ala Met Glu Glu Val Thr Ala Glu Asp
-20 -15 -10 -5

Val Ser Ile Ala Met His Asn Asn Gln Arg Trp His Tyr Glu Met Ile
-1 1 5 10

Asn Ala Pro Gln Ala Trp Asn Val Thr Thr Gly Ser Arg Asn Val Arg
15 20 25

Ile Ala Val Leu Asp Thr Gly Ile Asp Ala Asn His Pro Asn Leu Arg
30 35 40

Asn Leu Val Asn Thr Ser Leu Gly Arg Ser Phe Val Gly Gly Gly Thr
45 50 55 60

Gly Asp Val Gln Gly His Gly Thr His Val Ala Gly Thr Ile Ala Ser
65 70 75

Tyr Gly Ser Val Ser Gly Val Met Gln Asn Ala Thr Leu Ile Pro Val
80 85 90

Lys Val Leu Gly Asp Asn Gly Ser Gly Ser Met Tyr Gly Ile Gln Gln
95 100 105

Gly Ile Leu Tyr Ala Ala Ser Val Asn Ser Asp Val Ile Asn Met Ser
110 115 120

Leu Gly Gly Gly Gly Tyr Ser Gln Gly Met Asp Asp Ala Ile Arg Thr
125 130 135 140

Ala Val Ser Ser Gly Ser Ile Val Val Ala Ala Ser Gly Asn Asp Ser
145 150 155

Arg Gly Ser Ile Ser Tyr Pro Ala Ala Tyr Ser Gly Ala Ile Ala Val
160 165 170

Gly Ser Val Thr Ser Asn Arg Thr Arg Ser Ser Phe Ser Asn Tyr Gly
175 180 185

Gln Gly Leu Glu Leu Met Ala Pro Gly Ser Asn Ile Tyr Ser Thr Tyr
190 195 200

Pro Asn Gly Gln Phe Arg Thr Leu Ser Gly Thr Ser Met Ala Thr Pro
205 210 215 220

```
His Val Ala Gly Val Ala Gly Leu Ile Arg Ala Ala Asn Pro Asn Ile
            225                 230                 235

Ser Val Ala Glu Ala Arg Thr Ile Leu Arg Asn Thr Ala Gln Tyr Ala
        240                 245                 250

Gly Ser Phe Asn Gln Tyr Gly Tyr Gly Ile Val Asp Ala Asn Ala Ala
            255                 260                 265

Val Arg Ala Ala Arg Gly Gln Thr Gln Gln Pro Arg Tyr Glu Thr Asn
        270                 275                 280

Thr Thr Val Ser Thr Asn Ala Ser Thr Tyr Arg Arg Gly Gln Ser Val
285                 290                 295                 300

Thr Val Arg Ala Asp Val Val Asp Gln Asp Gly Arg Ala Leu Ala Asn
            305                 310                 315

Ser Thr Val Gln Phe Thr Ile Thr Arg Pro Asn Gly Thr Thr Val Thr
        320                 325                 330

Asn Thr Ala Thr Thr Asn Asn Ser Gly Val Ala Thr Trp Thr Ile Ala
            335                 340                 345

Thr Ser Ser Ser Thr Ala Arg Gly Thr Tyr Gly Val Gln Ala Ala Thr
        350                 355                 360

Ser Leu Ser Gly Tyr Glu Gly Ser Thr Ala Thr Thr Ser Phe Val Ile
365                 370                 375                 380

Asn
```

<210> SEQ ID NO 5
<211> LENGTH: 1737
<212> TYPE: DNA
<213> ORGANISM: Paenibacillus dendritiformis
<220> FEATURE:
<221> NAME/KEY: CDS
<222> LOCATION: (1)..(1734)
<220> FEATURE:
<221> NAME/KEY: sig_peptide
<222> LOCATION: (1)..(90)
<220> FEATURE:
<221> NAME/KEY: mat_peptide
<222> LOCATION: (475)..(1323)

<400> SEQUENCE: 5

```
atg aag aag ttt cta agc tct gtt tta gct gcc att ttg tta atg        45
Met Lys Lys Phe Leu Ser Ser Val Leu Ala Ala Ile Leu Leu Met
        -155                -150                -145 gtc act tta tta aca ggg gtg tcg ttt ggc agc ccc gct gag ggt        90
Val Thr Leu Leu Thr Gly Val Ser Phe Gly Ser Pro Ala Glu Gly
        -140                -135                -130 cac tcg agt gat tat att gaa ggt caa ctc gtg gtg tcg ctc gag       135
His Ser Ser Asp Tyr Ile Glu Gly Gln Leu Val Val Ser Leu Glu
        -125                -120                -115 gaa ccg ttc atg gat tcg agc caa agc gtg gat gat ata ttg atg       180
Glu Pro Phe Met Asp Ser Ser Gln Ser Val Asp Asp Ile Leu Met
        -110                -105                -100 gaa gcc gat tca ctc acg gag agc ggt ttt gct att gcc gat tca ctg   228
Glu Ala Asp Ser Leu Thr Glu Ser Gly Phe Ala Ile Ala Asp Ser Leu
            -95                 -90                 -85 ttc ggg cag gat gcc ggc act ttc tcg gtg cag gcg ctg gat agc gat   276
Phe Gly Gln Asp Ala Gly Thr Phe Ser Val Gln Ala Leu Asp Ser Asp
        -80                 -75                 -70 gtc agg gct acg gcg ata gag aaa atg gga ttg gtc tat ttg gtc gag   324
Val Arg Ala Thr Ala Ile Glu Lys Met Gly Leu Val Tyr Leu Val Glu
        -65                 -60                 -55 tac tct gta aag gac tac aag tca atc gag tcc gcc aaa aac act ttg   372
Tyr Ser Val Lys Asp Tyr Lys Ser Ile Glu Ser Ala Lys Asn Thr Leu
```

```
      -50            -45            -40            -35
gag aaa aaa tta gac aac ctt ggt ttc cat gtt cgg tac atc tcg gaa        420
Glu Lys Lys Leu Asp Asn Leu Gly Phe His Val Arg Tyr Ile Ser Glu
            -30            -25            -20 aac cgc aaa atg tac gcg ctt gaa acg gca acc gtg caa gat gtt tca        468
Asn Arg Lys Met Tyr Ala Leu Glu Thr Ala Thr Val Gln Asp Val Ser
            -15            -10             -5 cct caa gcc att cac aac aac caa cgt tgg cat tat gag atg att aag        516
Pro Gln Ala Ile His Asn Asn Gln Arg Trp His Tyr Glu Met Ile Lys
     -1   1               5                  10 gtt ccg caa gcc tgg gag atc acg gcc ggg tcg agc tca gtc cgg atc        564
Val Pro Gln Ala Trp Glu Ile Thr Ala Gly Ser Ser Ser Val Arg Ile
 15           20              25                      30 ggc gtg ctt gac acg gga att gac agc aac cat ccg agc ttg aaa gat        612
Gly Val Leu Asp Thr Gly Ile Asp Ser Asn His Pro Ser Leu Lys Asp
              35              40                      45 ctc gtg aac act agc ttg ggc agc agc ttt gta ggc ggt acc aca aac        660
Leu Val Asn Thr Ser Leu Gly Ser Ser Phe Val Gly Gly Thr Thr Asn
              50              55                      60 gat ggt aat ggg cat ggc act cat gtc gct gga acg att gcc agt tat        708
Asp Gly Asn Gly His Gly Thr His Val Ala Gly Thr Ile Ala Ser Tyr
          65              70              75 gga tcg gtg tca ggc gtc atg cag aac gcg acc ttg att cct att aaa        756
Gly Ser Val Ser Gly Val Met Gln Asn Ala Thr Leu Ile Pro Ile Lys
 80              85              90 gtg ctt aac gac agc ggt tca ggt tcg ctg tat ggc gtt caa caa ggt        804
Val Leu Asn Asp Ser Gly Ser Gly Ser Leu Tyr Gly Val Gln Gln Gly
 95             100             105                     110 att gtt tac gcc gct aat att aga gcc gat gtc atc aat atg tcg ctg        852
Ile Val Tyr Ala Ala Asn Ile Arg Ala Asp Val Ile Asn Met Ser Leu
                115             120             125 ggt ggc ggc ggt tac gat caa ggg atg gat gag gcg att caa acc gca        900
Gly Gly Gly Gly Tyr Asp Gln Gly Met Asp Glu Ala Ile Gln Thr Ala
            130             135             140 gtc agc ttg ggc acc atc gtg gtg gcg gcc gct ggc aat gac gga cgc        948
Val Ser Leu Gly Thr Ile Val Val Ala Ala Ala Gly Asn Asp Gly Arg
        145             150             155 cca agc atc tct tat ccg gcg gct tac agc ggc tcg atc gcg gtt ggt        996
Pro Ser Ile Ser Tyr Pro Ala Ala Tyr Ser Gly Ser Ile Ala Val Gly
    160             165             170 tcc gtg acc tcg agc aga acg cgt tca agc ttc tcc aat tat gga ccg       1044
Ser Val Thr Ser Ser Arg Thr Arg Ser Ser Phe Ser Asn Tyr Gly Pro
175             180             185                     190 ggt ctt gat gtg atg gct cct ggg tcg aac ata tac agc aca tat aag       1092
Gly Leu Asp Val Met Ala Pro Gly Ser Asn Ile Tyr Ser Thr Tyr Lys
                195             200             205 aac ggc caa tac aca act ttg tct gga acc tcg atg gca acc cct cat       1140
Asn Gly Gln Tyr Thr Thr Leu Ser Gly Thr Ser Met Ala Thr Pro His
            210             215             220 gtg act ggc gta ttc gga ctg atg aga tcg gtt aat ccg aat ctt agc       1188
Val Thr Gly Val Phe Gly Leu Met Arg Ser Val Asn Pro Asn Leu Ser
        225             230             235 cct gct gcg gcc gga gat att ctc cgc aat aca gcg cag cct gcc gga       1236
Pro Ala Ala Ala Gly Asp Ile Leu Arg Asn Thr Ala Gln Pro Ala Gly
    240             245             250 agc tct gat cag tat ggg cat ggc att gtt gat gcg cac gct gct gtg       1284
Ser Ser Asp Gln Tyr Gly His Gly Ile Val Asp Ala His Ala Ala Val
255             260             265                     270 cta gcg gca gcc ggc ggg ggc gat acg cca gcc ccg agc gca cct ggc       1332
```

```
Leu Ala Ala Ala Gly Gly Asp Thr Pro Ala Pro Ser Ala Pro Gly
            275             280             285 gat tta ata tcc acg ggc caa act ggc aca agc gta tcg ctt agc tgg      1380
Asp Leu Ile Ser Thr Gly Gln Thr Gly Thr Ser Val Ser Leu Ser Trp
        290             295             300 aat cct ccc acg gac aac gag ggc gta acc gct tat gaa gta tat aac      1428
Asn Pro Pro Thr Asp Asn Glu Gly Val Thr Ala Tyr Glu Val Tyr Asn
        305             310             315 gga gac tcg tta gcc gcc aca gtc gcg aat act tcg gcg acg gtt acc      1476
Gly Asp Ser Leu Ala Ala Thr Val Ala Asn Thr Ser Ala Thr Val Thr
    320             325             330 gac ttg acg gcc gat acc aca tat acg ttc aca gtt aga gcg gta gac      1524
Asp Leu Thr Ala Asp Thr Thr Tyr Thr Phe Thr Val Arg Ala Val Asp
335             340             345             350 gcc tca ggc aat cgg tcc gaa gca agc aat gcc gta acg gta acg acg      1572
Ala Ser Gly Asn Arg Ser Glu Ala Ser Asn Ala Val Thr Val Thr Thr
            355             360             365 gat tcc gat tcg tca caa ccg tct ccg act tgg gct ccg ggt ata tcg      1620
Asp Ser Asp Ser Ser Gln Pro Ser Pro Thr Trp Ala Pro Gly Ile Ser
        370             375             380 tat aag atc ggg gag gaa gtg act tac ggc gaa gca acg tac cag tgt      1668
Tyr Lys Ile Gly Glu Glu Val Thr Tyr Gly Glu Ala Thr Tyr Gln Cys
        385             390             395 ctt caa gaa cat att tcg atg gcg ggc tgg gaa ccg ctt aac gta ccg      1716
Leu Gln Glu His Ile Ser Met Ala Gly Trp Glu Pro Leu Asn Val Pro
400             405             410 gca tta tgg tta gag aaa tag                                          1737
Ala Leu Trp Leu Glu Lys
415             420

<210> SEQ ID NO 6
<211> LENGTH: 578
<212> TYPE: PRT
<213> ORGANISM: Paenibacillus dendritiformis

<400> SEQUENCE: 6

Met Lys Lys Phe Leu Ser Ser Val Leu Ala Ala Ile Leu Leu Met
            -155            -150            -145

Val Thr Leu Leu Thr Gly Val Ser Phe Gly Ser Pro Ala Glu Gly
            -140            -135            -130

His Ser Ser Asp Tyr Ile Glu Gly Gln Leu Val Val Ser Leu Glu
            -125            -120            -115

Glu Pro Phe Met Asp Ser Ser Gln Ser Val Asp Asp Ile Leu Met
            -110            -105            -100

Glu Ala Asp Ser Leu Thr Glu Ser Gly Phe Ala Ile Ala Asp Ser Leu
            -95             -90             -85

Phe Gly Gln Asp Ala Gly Thr Phe Ser Val Gln Ala Leu Asp Ser Asp
        -80             -75             -70

Val Arg Ala Thr Ala Ile Glu Lys Met Gly Leu Val Tyr Leu Val Glu
        -65             -60             -55

Tyr Ser Val Lys Asp Tyr Lys Ser Ile Glu Ser Ala Lys Asn Thr Leu
-50             -45             -40             -35

Glu Lys Lys Leu Asp Asn Leu Gly Phe His Val Arg Tyr Ile Ser Glu
            -30             -25             -20

Asn Arg Lys Met Tyr Ala Leu Glu Thr Ala Thr Val Gln Asp Val Ser
            -15             -10             -5

Pro Gln Ala Ile His Asn Asn Gln Arg Trp His Tyr Glu Met Ile Lys
    -1  1               5               10
```

```
Val Pro Gln Ala Trp Glu Ile Thr Ala Gly Ser Ser Val Arg Ile
 15              20                  25                  30

Gly Val Leu Asp Thr Gly Ile Asp Ser Asn His Pro Ser Leu Lys Asp
                 35                  40                  45

Leu Val Asn Thr Ser Leu Gly Ser Ser Phe Val Gly Thr Thr Asn
             50                  55                  60

Asp Gly Asn Gly His Gly Thr His Val Ala Gly Thr Ile Ala Ser Tyr
             65                  70                  75

Gly Ser Val Ser Gly Val Met Gln Asn Ala Thr Leu Ile Pro Ile Lys
         80                  85                  90

Val Leu Asn Asp Ser Gly Ser Gly Ser Leu Tyr Gly Val Gln Gln Gly
 95                 100                 105                 110

Ile Val Tyr Ala Ala Asn Ile Arg Ala Asp Val Ile Asn Met Ser Leu
                 115                 120                 125

Gly Gly Gly Gly Tyr Asp Gln Gly Met Asp Glu Ala Ile Gln Thr Ala
                 130                 135                 140

Val Ser Leu Gly Thr Ile Val Ala Ala Ala Gly Asn Asp Gly Arg
             145                 150                 155

Pro Ser Ile Ser Tyr Pro Ala Ala Tyr Ser Gly Ser Ile Ala Val Gly
         160                 165                 170

Ser Val Thr Ser Ser Arg Thr Arg Ser Ser Phe Ser Asn Tyr Gly Pro
175                 180                 185                 190

Gly Leu Asp Val Met Ala Pro Gly Ser Asn Ile Tyr Ser Thr Tyr Lys
                 195                 200                 205

Asn Gly Gln Tyr Thr Thr Leu Ser Gly Thr Ser Met Ala Thr Pro His
             210                 215                 220

Val Thr Gly Val Phe Gly Leu Met Arg Ser Val Asn Pro Asn Leu Ser
             225                 230                 235

Pro Ala Ala Ala Gly Asp Ile Leu Arg Asn Thr Ala Gln Pro Ala Gly
240                 245                 250

Ser Ser Asp Gln Tyr Gly His Gly Ile Val Asp Ala His Ala Ala Val
255                 260                 265                 270

Leu Ala Ala Ala Gly Gly Asp Thr Pro Ala Pro Ser Ala Pro Gly
                 275                 280                 285

Asp Leu Ile Ser Thr Gly Gln Thr Gly Thr Ser Val Ser Leu Ser Trp
             290                 295                 300

Asn Pro Pro Thr Asp Asn Glu Gly Val Thr Ala Tyr Glu Val Tyr Asn
             305                 310                 315

Gly Asp Ser Leu Ala Ala Thr Val Ala Asn Thr Ser Ala Thr Val Thr
             320                 325                 330

Asp Leu Thr Ala Asp Thr Thr Tyr Thr Phe Thr Val Arg Ala Val Asp
335                 340                 345                 350

Ala Ser Gly Asn Arg Ser Glu Ala Ser Asn Ala Val Thr Val Thr Thr
                 355                 360                 365

Asp Ser Asp Ser Ser Gln Pro Ser Pro Thr Trp Ala Pro Gly Ile Ser
             370                 375                 380

Tyr Lys Ile Gly Glu Glu Val Thr Tyr Gly Glu Ala Thr Tyr Gln Cys
             385                 390                 395

Leu Gln Glu His Ile Ser Met Ala Gly Trp Glu Pro Leu Asn Val Pro
         400                 405                 410

Ala Leu Trp Leu Glu Lys
415                 420
```

<210> SEQ ID NO 7
<211> LENGTH: 48
<212> TYPE: DNA
<213> ORGANISM: Artificial
<220> FEATURE:
<223> OTHER INFORMATION: Synthetic

<400> SEQUENCE: 7
gttcatcgat cgcatcggct gatgatatga agaaagaaga ctatattg         48

<210> SEQ ID NO 8
<211> LENGTH: 46
<212> TYPE: DNA
<213> ORGANISM: Artificial
<220> FEATURE:
<223> OTHER INFORMATION: Synthetic

<400> SEQUENCE: 8
ccaaggccgg ttttttatgt tttattgtaa tcgaaaagat gttgtt           46

<210> SEQ ID NO 9
<211> LENGTH: 47
<212> TYPE: DNA
<213> ORGANISM: Artificial
<220> FEATURE:
<223> OTHER INFORMATION: Synthetic

<400> SEQUENCE: 9
cttttagttc atcgatcgca tcggcttcga aggtaaaaa taacggt           47

<210> SEQ ID NO 10
<211> LENGTH: 42
<212> TYPE: DNA
<213> ORGANISM: Artificial
<220> FEATURE:
<223> OTHER INFORMATION: Synthetic

<400> SEQUENCE: 10
ccaaggccgg ttttttatgt tttagtttat gacaaagctc gt               42

<210> SEQ ID NO 11
<211> LENGTH: 9705
<212> TYPE: DNA
<213> ORGANISM: Artificial
<220> FEATURE:
<223> OTHER INFORMATION: Synthetic

<400> SEQUENCE: 11
gagtatcgcc agtaagggc gttttttgttt tctggttgtt ttcttcattt caggtttcgc    60
cctttccttg ccaaatataa gaaaaacggc gttccgataa tcgcggtgac aatgccgacc   120
ggtgattcat aaggaaatgc aatccatctg gccagaacat ctgcgtacac cagcaaaatg   180
gcaccgaaca gtgccgaaaa cggaagcacg tattgataat gttctccgat cagcttgcgg   240
acaatatgcg ggacgagcag cccgacaaag ccaatcggcc cggcgacggc tacgaaagcg   300
ccggaaagaa ttaaaataat caaactgatc agaatcctga tgccgttcat attttgtcca   360
agcccttttg ctgtttcgtc tccgagaccg agaacagaaa cagaaccgga aaatacgagg   420
gcaagcccga tgccaatgac agaaaaagga gcgatggtta tgacgtcctg ccagttgctg   480
ccgtcgattg cgcctgtcat ccagtacaga acatcctcac ctgactcatt taaataatg   540 atggcctgtg tcatagagga gaggaacaag tgcacggcca ttcctgacag cgccagcttg   600
acaggcgtca ttccgccgga tgaggcaatc atatacacaa tcgcgccgcc tgctgccgca   660

```
cccgcaaaag cgaatataac agatgaatag ggcgatgccg gcagaatgac gagagaagca      720
acaacaaaaa gcgatgcacc cgcattcaca ccgaaaattt ggggtgaagc cagaggattt      780
ctggtcatag cctgcatcag cgcccctgct acagctaggc tggcgccgac aaaaacgccg      840
attaatgtgc ggggaaggcg aagagtagag atgatgagct gttcctttga accgtcccat      900
acaaaaagat atttcaatga atctatgatg ctgatgtctg aggctcctac tgaaagattc      960
agcccaagcc caaatataaa aataatcagt gcaatgataa acatcatcag tcttgatgat     1020
gagcgccgtt tggctgaatg atacaacagt ctcacttcct tactgcgtct ggttgcaaaa     1080
acgaagaagc aaggattccc ctcgcttctc atttgtccta tttattatac actttttaa      1140 gcacatcttt ggcgcttgtt tcactagact tgatgcctct gaatcttgtc caagtgtcac     1200
ggtccgcatc atagacttgt ccatttttca ccgctttgag attttccag agcgggttcg      1260 ttttccactc atctacaatg gttttgcctt cgttggctga gatgaacaaa atatcaggat     1320
cgattttgct caattgctca aggctgacct cttgataggc gttatctgac ttcacagcgt     1380
gtgtaaagcc tagcatttta aagatttctc cgtcatagga tgatgatgta tgaagctgga     1440
aggaatccgc tcttgcaacg ccgagaacga tgttgcggtt ttcatctttc ggaagttcgg     1500
cttttagatc gttgatgact ttttgtgct cggcaagctt ttcttttcct tcatcttctt      1560
tatttaatgc tttagcaatg gtcgtaaagc tgtcgatcgt ttcgtcatat gtcgcttcac     1620 ggcttttaa ttcaatcgtc ggggcgattt ttttcagctg tttataaatg tttttatggc      1680
gctcagcgtc agcgatgatt aaatcaggct tcaaggaact gatgacctca agattgggtt     1740
cgctgcgtgt gcctacagat gtgtaatcaa tggagctgcc gacaagcttt ttaatcatat     1800 ctttttttgtt gtcatctgcg atgcccaccg gcgtaatgcc gagattgtga acggcatcca    1860
agaatgaaag ctcaagcaca accacccgct taggtgtgcc gcttactgtc gttttttcctt   1920 cttcgtcatg gatcactctg gaatccttag actcgctttt gccgcttccg ttgttattct     1980
ggcttgatga acagccggat acaatgaggc aggcgagcaa taaaacactc atgatggcaa     2040
tcaacttgtt agaataggtg cgcatgtcat tcttccttt ttcagattta gtaatgagaa      2100
tcattatcac atgtaacact ataatagcat ggcttatcat gtcaatattt ttttagtaaa     2160
gaaagctgcg ttttttactgc tttctcatga aagcatcatc agacacaaat aagtggtatg   2220
cagcgttacc gtgtcttcga gacaaaaacg catgggcgtt ggctttagag gtttcgaaca    2280
tatcagcagt gacataagga aggagagtgc tgagataacc ggacaatttc tttctatttt    2340
catctgttag tgcaaattca atgtcgccga tattcatgat aatcgagaaa acaaagtcga    2400
tatcgatatg aaaatgttcc tcggcaaaaa ccgcaagctc gtgaattcct ggtgaacatc     2460
cggcacgctt atggaaaatc tgtttgacta aatcactcac aatccaagca ttgtattgct    2520
gttctggtga aaagtattgc attagacata cctcctgctc gtacggataa aggcagcgtt    2580
tcatggtcgt gtgctccgtg cagcggcttc tccttaattt tgattttttct gaaataggt    2640 cccgttccta tcacttttacc atggacggaa acaaatagc tactaccatt cctcctgttt    2700
ttctcttcaa tgttctggaa tctgtttcag gtacagacga tcgggtatga agaaatata     2760 gaaaacatga aggaggaata tcgacatgaa accagttgta aaagagtata caaatgacga    2820
acagctcatg aaagatgtag aggaattgca gaaatgggt gttgcgaaag aggatgtata     2880
cgtcttagct cacgacgatg acagaacgga acgcctggct gacaacacga acgccaacac    2940
gatcggagcc aaagaaacag gtttcaagca cgcggtggga aatatcttca ataaaaagg    3000
```

```
agacgagctc cgcaataaaa ttcacgaaat cggttttcct gaagatgaag ccgctcaatt    3060
tgaaaaacgc ttagatgaag gaaaagtgct tctctttgtg acagataacg aaaaagtgaa    3120
agcttgggca taaagcaagg aaaaaaccaa aaggccaatg tcggcctttt ggtttttttg    3180
cggtctttgc ggtgggattt tgcagaatgc cgcaatagga tagcggaaca ttttcggttc    3240
tgaatgtccc tcaatttgct attatatttt tgtgataaat tggaataaaa tctcacaaaa    3300
tagaaaatgg gggtacatag tggccatcat ggccagctag catgcacatg ggatctggga    3360
ccaataataa tgactagaga agaaagaatg aagattgttc atgaaattaa ggaacgaata    3420
ttggataaag tggggtattt ttaaaatata tatttatgtt acagtaatat tgactttaa     3480 aaaaggattg attctaagaa gaaagcagac aagtaagcct cctaaattca ctttagataa    3540
aaatttagga ggcatatcaa atgaaccttta ataaaattga tttagacaat tggaagagaa   3600
aagagatatt taatcattat ttgaaccaac aaacgacttt tagtataacc acagaaattg    3660
atattagtgt tttataccga aacataaaac aagaaggata taaattttac cctgcattta    3720 tttttcttagt gacaagggtg ataaaactcaa atacagcttt tagaactggt tacaatagcg   3780
acggagagtt aggttattgg gataagttag agccactttta tacaattttt gatggtgtat   3840
ctaaaacatt ctctggtatt tggactcctg taaagaatga cttcaaagag ttttatgatt    3900 tataccttc tgatgtagag aaatataatg gttcggggaa attgtttccc aaaacaccta     3960
tacctgaaaa tgcttttct ctttctatta ttccatggac ttcatttact gggtttaact    4020
taaatatcaa taataatagt aattaccttc tacccattat tacagcagga aaattcatta   4080
ataaaggtaa ttcaatatat ttaccgctat ctttacaggt acatcattct gtttgtgatg   4140
gttatcatgc aggattgttt atgaactcta ttcaggaatt gtcagatagg cctaatgact   4200 ggctttata atatgagata atgccgactg tacttttta agtcggtttt ctaacgatac      4260
attaataggt acgaaaaagc aactttttt gcgcttaaaa ccagtcatac caataactta    4320
agggtaacta gcctcgccgg aaagagcgaa atgcctcac atttgtgcca cctaaaaagg    4380
agcgatttac atatgagtta tgcagtttgt agaatgcaaa aagtgaaatc agctggacta   4440
aaaggcatgg catgccttcg atagtttat aatattagtg gagctcagtg agagcgaagc    4500
gaacacttga ttttttaatt ttctatcttt tataggtcat tagagtatac ttatttgtcc    4560
tataaactat ttagcagcat aatagattta ttgaataggt catttaagtt gagcatatta    4620
ggggaggaaa atcttggaga aatatttgaa gaacccgagg atctagatca ggtaccgcaa    4680
cgttcgcaga tgctgctgaa gagattatta aaaagctgaa agcaaaaggc tatcaattgg    4740
taactgtatc tcagcttgaa gaagtgaaga agcagagagg ctattgaata aatgagtaga    4800
aagcgccata tcggcgcttt tcttttggaa gaaaatatag ggaaaatggt acttgttaaa    4860
aattcggaat atttatacaa tatcatatgt atcacattga aaggaggggc ctgctgtcca    4920
gactgtccgc tgtgtaaaaa aaaggaataa aggggggttg acattattt actgatatgt     4980 ataatataat ttgtataaga aaatggaggg gccctcgaaa cgtaagatga aaccttagat    5040
aaaagtgctt tttttgttgc aattgaagaa ttattaatgt taagcttaat taaagataat    5100
atctttgaat tgtaacgccc ctcaaaagta agaactacaa aaaagaata cgttatatag     5160 aaatatgttt gaaccttctt cagattacaa atatattcgg acggactcta cctcaaatgc    5220
ttatctaact atagaatgac atacaagcac aaccttgaaa atttgaaaat ataactacca    5280
atgaacttgt tcatgtgaat tatcgctgta tttaattttc tcaattcaat atataatatg    5340
ccaatacatt gttacaagta gaaattaaga caccccttgat agccttacta tacctaacat   5400
```

```
gatgtagtat taaatgaata tgtaaatata tttatgataa gaagcgactt atttataatc    5460
attacatatt tttctattgg aatgattaag attccaatag aatagtgtat aaattattta    5520
tcttgaaagg agggatgcct aaaaacgaag aacattaaaa acatatattt gcaccgtcta    5580
atggatttat gaaaaatcat tttatcagtt tgaaaattat gtattatgga gctctgaaaa    5640
aaaggagagg ataaagaatg aagaaaccgt tggggaaaat tgtcgcaagc accgcactac    5700
tcatttctgt tgcttttagt tcatcgatcg catcggctga tgatatgaag aaagaagact    5760
atattgaagg tcagttaatc gtttctgtgg aaggaaaagt aaagaaaaaa gcaaaaaatg    5820
tttccttaat tcaagaaatg aacagtgtaa gtgacttact atttgacaat gcaaacttga    5880
ataaaaaagg ctttaaattt gtggattctt tacttgaagg aaaagatgcc aattctgttg    5940
cattgtttga taacaaattc aaagaaaaag ctgcaaaaaa gatgggatat gtataccttg    6000
tagaatattc tacagaggat tatgaatcta ttgatgcggc aaagaaagaa cttaaaaagc    6060
tattaaagga acttgattta aaagttaaag atgtgactga aaactttaca atgcatttat    6120
tagaagatgg agccgcaaca gcttcagcaa ctgaaatagc accattaatg cacaacaatc    6180
aacgttggca ttatgaaatg attaacgcac ctcaagcatg gggaattaca actggaagca    6240
gtaatgtaag aattgccgtc ttagacacag gtattgatgc taaccatcca aacttacgta    6300
atctagttga tacaagtctt ggtagaagct ttgttgagg cggaacagga gatgtgcaag    6360
gtcacggaac gcatgttgca gggacaattg ccagttatgg ttccgtgtct ggtgtcatgc    6420
aaaatgctcg ccttattcct gtaaaagtat taggggacaa cggaagtggc agtatgtatg    6480
ggatccaaca aggaattctc tacgctgcta gtattaacgc ggatgtaata aatatgtcac    6540
taggtggcgg tggttatgat tctggaatga acaatgccat taatactgct gttagttctg    6600
gtactctcgt aattgctgct tctgggaatg atggaagagg aagtatttct tatccggctg    6660
cttatagtaa tgctattgca gtgggttctg taacatcgaa tagaactaga tccaacttct    6720
caaattatgg tagcggatta gaactaatgg ccccaggatc aaatatttat agtacttatc    6780
cgaatggtca attccgtaca ttatcaggta catctatggc cacaccacac gtagctgggg    6840
ttgcaggttt aattaaatca gcaaatccaa atctatcagt cacacaagtt agaaatatcc    6900
taagagatac tgcgcagtat gcaggaagtt ctaaccaata tggatatgga attgttaatg    6960
cttatgcggc agttcaagct gctggtgggg gagcggtaag ttatgaaact aatacatccg    7020
tttctacaaa tcaaagtacc tactatagag ggaataacgt gacaatgacg gctatcgtca    7080
ctgaccaaaa caatagtaga ttgcaagggg caactgtaaa ctttacaatt actcgtccga    7140
acggtaccac agttacaaat gctacaacga caaattcatc tggtgttgcg acatggacca    7200
ttggatccaa ctcatccaca gctgtgggga cgtatcaagt tcgtgcacaa caacgtatc    7260 cgaattatca atctagctca gcaacaacat cttttcgatt acaataaaac ataaaaaacc    7320
ggccttggcc ccgccggttt tttattattt ttcttcctcc gcatgttcaa tccgctccat    7380
aatcggtcga cgcggcggtt cgcgtccgga cagcacatca ccgaaatatt atggaagaaa    7440
atatcagcac catgacggcc aaacggatgc ttccaacggt gctaactata tcacgatgtc    7500
ctacaactat tatcacgatc atgataaaag ctccattttc ggatcaagtg acagcaaaac    7560
ctccgatgac ggcaaattaa aaattacgct gcatcataac cgctataaaa atattgtcca    7620
gcgcgcgccg agagtccgct tcgggcaagt gcacgtatac aacaactatt atgaaggaag    7680
cacaagctct tcaagttatc cttttagcta tgcatgggga atcggaaagt catctaaaat    7740
```

```
ctatgcccaa acaatgtca ttgacgtacc gggactgtca gctgctaaaa cgatcagcgt    7800
attcagcggg ggaacggctt tatatgactc cggcacgttg ctgaacggca cacagatcaa    7860
cgcatcggct gcaaacgggc tgagctcttc tgtcggctgg acgccgtctc tgcatggatc    7920
gattgatgct tctgctaatg tgaaatcaaa tgttataaat caagcgggtg cgggtaaatt    7980
aaattaagaa agtgaaaaac acaaagggtg ctaacctttg tgttttttaa ttaattaaaa    8040
tgtttattaa cttagttaag gagtagaatg gaaaagggga tcggaaaaca agtatatagg    8100
aggagaccta tttatggctt cagaaaaaga cgcaggaaaa cagtcagcag taaagcttgt    8160
tccattgctt attactgtcg ctgtgggact aatcatctgg tttattcccg ctccgtccgg    8220
acttgaacct aaagcttggc atttgtttgc gattttgtc gcaacaatta tcggctttat    8280
ctccaagccc ttgccaatgg gtgcaattgc aattttgca ttggcggtta ctgcactaac    8340
tggaacacta tcaattgagg atacattaag cggattcggg aataagacca tttggcttat    8400
cgttatcgca ttcttatt cccggggatt tatcaaaacc ggtctcggtg cgagaatttc    8460
gtatgtattc gttcagaaat tcggaaaaaa aacccttgga cttcttatt cactgctatt    8520
cagtgattta atactttcac ctgctattcc aagtaatacg gcgcgtgcag gaggcattat    8580
atttcctatt atcagatcat tatccgaaac attcggatca agcccggcaa atggaacaga    8640
gagaaaaatc ggtgcattct tattaaaaac cggttttcag gggaatctga tcacatctgc    8700
tatgttcctg acagcgatgg cggcgaaccc gctgattgcc aagctggccc atgatgtcgc    8760
aggggtggac ttaacatgga caagctgggc aattgccgcg attgtaccgg acttgtaag    8820
cttaatcatc acgccgcttg tgatttacaa actgtatccg ccggaaatca agaaacacc    8880
ggatgcggcg aaaatcgcaa cagaaaaact gaaagaaatg ggaccgttca aaaaatcgga    8940
gctttccatg gttatcgtgt ttcttttggt gcttgtgctg tggattttg gcggcagctt    9000
caacatcgac gctaccacaa ccgcattgat cggtttggcc gttctcttat tatcacaagt    9060
tctgacttgg gatgatatca agaaagaaca gggcgcttgg gatacgctca cttggtttgc    9120
ggcgcttgtc atgctcgcca acttcttgaa tgaattaggc atggtgtctt ggttcagtaa    9180
tgccatgaaa tcatccgtat cagggttctc ttggattgtg gcattcatca ttttaattgt    9240
tgtgtattat tactctcact atttctttgc aagtgcgaca gcccacatca gtgcgatgta    9300
ttcagcattt ttggctgtcg tcgtggcagc gggcgcaccg ccgcttttag cagcgctgag    9360
cctcgcgttc atcagcaacc tgttcgggtc aacgactcac tacggttctg gagcggctcc    9420
ggtcttcttc ggagcaggct acatcccgca aggcaaatgg tggtccatcg gatttatcct    9480
gtcgattgtt catatcatcg tatggcttgt gatcggcgga ttatggtgga agtactagg    9540
aatatggtag aaagaaaaag gcagacgcgg tctgcctttt tttattttca ctccttcgta    9600
agaaaatgga ttttgaaaaa tgagaaaatt ccctgtgaaa aatggtatga tctaggtaga    9660
aaggacggct ggtgctgtgg tgaaaagcg gttccatttt tccct                    9705
```

<210> SEQ ID NO 12
<211> LENGTH: 9678
<212> TYPE: DNA
<213> ORGANISM: Bacillus borgouniensis

<400> SEQUENCE: 12

```
gagtatcgcc agtaagggc gttttgtttt tctggttgtt ttcttcatt caggtttcgc     60
cctttccttg ccaaatataa gaaaacggc gttccgataa tcgcggtgac aatgccgacc    120
ggtgattcat aaggaaatgc aatccatctg gccagaacat ctgcgtacac cagcaaaatg    180
```

```
gcaccgaaca gtgccgaaaa cggaagcacg tattgataat gttctccgat cagcttgcgg    240
acaatatgcg ggacgagcag cccgacaaag ccaatcggcc cggcgacggc tacggaagcg    300
ccggaaagaa ttaaaataat caaactgatc agaatcctga tgccgttcat attttgtcca    360 agccctttg ctgtttcgtc tccgagaccg agaacagaaa cagaaccgga aaatacgagg     420
gcaagcccga tgccaatgac agaaaaagga gcgatggtta tgacgtcctg ccagttgctg    480
ccgtcgattg cgcctgtcat ccagtacaga acatcctcac ctgactcatt taaaataatg    540
atggcctgtg tcatagagga gaggaacaag tgcacggcca ttcctgacag cgccagcttg    600
acaggcgtca ttccgccgga tgaggcaatc atatacacaa tcgcgccgcc tgctgccgca    660
cccgcaaaag cgaatataac agatgaatag ggcgatgccg cagaatgac gagagaagca     720 acaacaaaaa gcgatgcacc cgcattcaca ccgaaaattt ggggtgaagc cagaggattt    780
ctggtcatag cctgcatcag cgcccctgct acagctaggc tggcgccgac aaaaacgccg    840
attaatgtgc ggggaaggcg aagagtagag atgatgagct gttcctttga accgtcccat    900
acaaaaagat atttcaatga atctatgatg ctgatgtctg aggctcctac tgaaagattc    960
agcccaagcc caaatataaa aataatcagt gcaatgataa acatcatcag tcttgatgat   1020
gagcgccgtt tggctgaatg atacaacagt ctcacttcct tactgcgtct ggttgcaaaa   1080
acgaagaagc aaggattccc ctcgcttctc atttgtccta tttattatac acttttttaa   1140
gcacatcttt ggcgcttgtt tcactagact tgatgcctct gaatcttgtc caagtgtcac   1200
ggtccgcatc atagacttgt ccattttttca ccgctttgag atttttccag agcgggttcg   1260
ttttccactc atctacaatg gttttgcctt cgttggctga gatgaacaaa atatcaggat   1320
cgattttgct caattgctca aggctgacct cttgataggc gttatctgac ttcacagcgt   1380
gtgtaaagcc tagcatttta aagatttctc cgtcatagga tgatgatgta tgaagctgga   1440
aggaatccgc tcttgcaacg ccgagaacga tgttgcggtt ttcatctttc ggaagttcgg   1500
cttttagatc gttgatgact ttttgtgct cggcaagctt ttctttcct tcatcttctt    1560 tatttaatgc tttagcaatg gtcgtaaagc tgtcgatcgt ttcgtcatat gtcgcttcac   1620 ggcttttaa ttcaatcgtc ggggcgattt ttttcagctg tttataaatg ttttatggc     1680 gctcagcgtc agcgatgatt aaatcaggct tcaaggaact gatgacctca agattgggtt   1740
cgctgcgtgt gcctacagat gtgtaatcaa tggagctgcc gacaagcttt ttaatcatat   1800
cttttttgtt gtcatctgcg atgcccaccg gcgtaatgcc gagattgtga acggcatcca   1860
agaatgaaag ctcaagcaca accacccgct taggtgtgcc gcttactgtc gttttttcctt  1920 cttcgtcatg gatcactctg gaatccttag actcgctttt gccgcttccg ttgttattct   1980
ggcttgatga acagccggat acaatgaggc aggcgagcaa taaaacactc atgatggcaa   2040
tcaacttgtt agaataggtg cgcatgtcat tcttccttt ttcagattta gtaatgagaa     2100
tcattatcac atgtaacact ataatagcat ggcttatcat gtcaatattt ttttagtaaa   2160
gaaagctgcg ttttactgc tttctcatga agcatcatc agacacaaat aagtggtatg      2220
cagcgttacc gtgtcttcga gacaaaaacg catgggcgtt ggcttagag gtttcgaaca     2280 tatcagcagt gacataagga aggagagtgc tgagataacc ggacaatttc ttttctattt   2340
catctgttag tgcaaattca atgtcgccga tattcatgat aatcgagaaa acaaagtcga   2400
tatcgatatg aaaatgttcc tcggcaaaaa ccgcaagctc gtgaattcct ggtgaacatc   2460
cggcacgctt atggaaaatc tgtttgacta aatcactcac aatccaagca ttgtattgct   2520
```

```
gttctggtga aaagtattgc attagacata cctcctgctc gtacggataa aggcagcgtt      2580
tcatggtcgt gtgctccgtg cagcggcttc tccttaattt tgattttttct gaaaataggt     2640 cccgttccta tcactttacc atggacggaa aacaaatagc tactaccatt cctcctgttt      2700
ttctcttcaa tgttctggaa tctgtttcag gtacagacga tcgggtatga agaaatata      2760 gaaaacatga aggaggaata tcgacatgaa accagttgta aaagagtata caaatgacga      2820
acagctcatg aaagatgtag aggaattgca gaaaatgggt gttgcgaaag aggatgtata      2880
cgtcttagct cacgacgatg acagaacgga acgcctggct gacaacacga acgccaacac      2940
gatcggagcc aaagaaacag gtttcaagca cgcggtggga aatatcttca ataaaaaagg      3000
agacgagctc cgcaataaaa ttcacgaaat cggttttttct gaagatgaag ccgctcaatt     3060
tgaaaaacgc ttagatgaag aaaagtgct tctctttgtg acagataacg aaaaagtgaa      3120
agcttgggca taaagcaagg aaaaaaccaa aaggccaatg tcggcctttt ggttttttg      3180 cggtctttgc ggtgggattt tgcagaatgc cgcaatagga tagcggaaca ttttcggttc     3240
tgaatgtccc tcaatttgct attatatttt tgtgataaat tggaataaaa tctcacaaaa     3300
tagaaaatgg gggtacatag tggccatcat ggccagctag catgcacatg ggatctggga     3360
ccaataataa tgactagaga agaaagaatg aagattgttc atgaaattaa ggaacgaata     3420
ttggataaag tggggtattt ttaaaatata tatttatgtt acagtaatat tgacttttaa     3480
aaaaggattg attctaagaa gaaagcagac aagtaagcct cctaaattca ctttagataa     3540
aaatttagga ggcatatcaa atgaacttta ataaaattga tttagacaat tggaagagaa     3600
aagagatatt taatcattat ttgaaccaac aaacgacttt tagtataacc acagaaattg     3660
atattagtgt tttataccga aacataaaac aagaaggata taaatttttac cctgcattta     3720 ttttcttagt gacaagggtg ataaactcaa atacagcttt tagaactggt tacaatagcg     3780
acggagagtt aggttattgg gataagttag agccactta tacaattttt gatggtgtat      3840
ctaaaacatt ctctggtatt tggactcctg taaagaatga cttcaaagag ttttatgatt     3900 tataccttttc tgatgtagag aaatataatg gttcggggaa attgtttccc aaaacaccta    3960
tacctgaaaa tgcttttttct ctttctatta ttccatggac ttcatttact gggtttaact    4020
taaatatcaa taataatagt aattaccttc tacccattat tacagcagga aaattcatta    4080
ataaaggtaa ttcaatatat ttaccgctat ctttacaggt acatcattct gtttgtgatg    4140
gttatcatgc aggattgttt atgaactcta ttcaggaatt gtcagatagg cctaatgact    4200
ggcttttata atatgagata atgccgactg tactttttac agtcggtttt ctaacgatac    4260
attaataggt acgaaaaagc aacttttttt gcgcttaaaa ccagtcatac caataactta    4320
agggtaacta gcctcgccgg aaagagcgaa aatgcctcac atttgtgcca cctaaaaagg     4380
agcgatttac atatgagtta tgcagtttgt agaatgcaaa aagtgaaatc agctggacta    4440
aaaggcatgg catgccttcg atagtttatt aatattagtg gagctcagtg agagcgaagc    4500
gaacacttga ttttttaatt ttctatcttt tataggtcat tagagtatac ttatttgtcc    4560
tataaactat ttagcagcat aatagattta ttgaataggt catttaagtt gagcatatta    4620
ggggaggaaa atcttggaga aatatttgaa gaacccgagg atctagatca ggtaccgcaa    4680
cgttcgcaga tgctgctgaa gagattatta aaaagctgaa agcaaaaggc tatcaattgg    4740
taactgtatc tcagcttgaa gaagtgaaga agcagagagg ctattgaata aatgagtaga    4800
aagcgccata tcggcgcttt tcttttggaa gaaaatatag ggaaatggt acttgttaaa     4860 aattcggaat attttatacaa tatcatatgt atcacattga aaggagggc ctgctgtcca     4920
```

```
gactgtccgc tgtgtaaaaa aaaggaataa aggggggttg acattatttt actgatatgt    4980
ataatataat ttgtataaga aaatggaggg gccctcgaaa cgtaagatga aaccttagat    5040
aaaagtgctt tttttgttgc aattgaagaa ttattaatgt taagcttaat taaagataat    5100
atctttgaat tgtaacgccc ctcaaaagta agaactacaa aaaaagaata cgttatatag    5160
aaatatgttt gaaccttctt cagattacaa atatattcgg acggactcta cctcaaatgc    5220
ttatctaact atagaatgac atacaagcac aaccttgaaa atttgaaaat ataactacca    5280
atgaacttgt tcatgtgaat tatcgctgta tttaatttc tcaattcaat atataatatg     5340
ccaatacatt gttacaagta gaaattaaga caccccttgat agccttacta tacctaacat   5400
gatgtagtat taaatgaata tgtaaatata tttatgataa gaagcgactt attttataatc  5460
attacatatt tttctattgg aatgattaag attccaatag aatagtgtat aaattattta   5520
tcttgaaagg agggatgcct aaaaacgaag aacattaaaa acatatattt gcaccgtcta   5580
atggatttat gaaaaatcat tttatcagtt tgaaaattat gtattatgga gctctgaaaa   5640
aaaggagagg ataaagaatg aagaaaccgt tggggaaaat tgtcgcaagc accgcactac   5700
tcatttctgt tgcttttagt tcatcgatcg catcggcttc gaaaggtaaa aataacggtg   5760
attatattga aggtcaactt gtcatttcga tcgaagacca gtcacaattt tccattcaag   5820
caacaaataa catcattaac aaagatgagg tattagaaaa taacggattt gagattgtag   5880
attcgctatt aggacaaaac aatccgaatg aaattcaagc atataatcat gactttactg   5940
caactgttgt aaatgaaatg ggtcttgttt atttggttga atacgatgtg aataaaatata  6000
agtcgattga taaagcaaaa aaagaacttg aaaaaacaat gaaagacctt ggattagaag   6060
ttcgatacgt gtctgagaac tttgttatgc atgcgatgga agaagtaaca gctgaagatg   6120
tttcgattgc gatgcataat aaccaaagat ggcattatga aatgattaat gctccacaag   6180
catggaatgt aacaacaggt tcaagaaatg tccgaatcgc tgttcttgat actggtattg   6240
atgcgaacca tcccaatctt cgtaacctag tcaatacgag tttaggacgt agcttcgttg   6300
gtggtggaac aggagatgtg caagggcatg gacacatgt agccggaaca attgcaagtt   6360
atggctcagt ttctggtgtg atgcaaaacg ctactttaat tccggtgaaa gtattgggag   6420
ataatggtag tggttcgatg tatggtattc agcaagggat tttatatgca gcgagtgtaa   6480
attctgatgt tattaatatg tctttaggtg gcggcggcta tagtcaaggg atggatgatg   6540
cgattcgtac agctgtatca tcaggctcaa tcgttgttgc tgcttctgga aacgactcac   6600
gtggaagtat ttcttatcca gctgcttaca gtggtgcaat cgctgttggt tcagttactt   6660
caaaccgaac tagatcaagc ttttctaact atggtcaagg attagagcta atggcaccag   6720
gttcaaatat ttatagcaca tatccaaatg gacagttccg cactttatct ggaacatcaa   6780
tggcaacacc acatgttgca ggtgtagcag gattaattcg agcagcaaac cctaatattt   6840
cagtagcaga agcaagaacg attttgcgaa atacagcaca atatgctgga agtttcaatc   6900
agtatggata cggaattgtc gatgcaaatg ctgcagttcg agctgctcgt ggtcaaacgc   6960
aacaaccaag atatgaaacg aatacaacag tgtctacaaa tgcatcaact tatagaagag   7020
gccaatctgt aactgtaaga gctgatgttg ttgaccaaga tggtcgagca ctagcgaatt   7080
caaccgttca atttacaatt acacgtccaa atggaacaac agtaacaaat acagcaacaa   7140
cgaataattc aggtgttgct acatggacga ttgcgacatc atcgtctaca gcaagaggca   7200
cgtatggtgt acaagccgca acgtctcttt caggttatga aggaagtaca gcgacaacga   7260
```

```
gctttgtcat aaactaataa aacataaaaa accggccttg gccccgccgg ttttttatta    7320 ttttcttcc tccgcatgtt caatccgctc cataatcggt cgacgcggcg gttcgcgtcc     7380
ggacagcaca tcaccgaaat attatggaag aaaatatcag caccatgacg gccaaacgga    7440
tgcttccaac ggtgctaact atatcacgat gtcctacaac tattatcacg atcatgataa    7500
aagctccatt ttcggatcaa gtgacagcaa aacctccgat gacggcaaat taaaaattac    7560
gctgcatcat aaccgctata aaatattgt ccagcgcgcg ccgagagtcc gcttcgggca     7620
agtgcacgta tacaacaact attatgaagg aagcacaagc tcttcaagtt atccttttag    7680
ctatgcatgg ggaatcggaa agtcatctaa aatctatgcc caaaacaatg tcattgacgt    7740
accgggactg tcagctgcta aaacgatcag cgtattcagc ggggaacgg ctttatatga     7800 ctccggcacg ttgctgaacg gcacacagat caacgcatcg gctgcaaacg ggctgagctc    7860
ttctgtcggc tggacgccgt ctctgcatgg atcgattgat gcttctgcta atgtgaaatc    7920
aaatgttata aatcaagcgg gtgcgggtaa attaaattaa gaaagtgaaa aacacaaagg    7980
gtgctaacct ttgtgttttt taattaatta aaatgtttat taacttagtt aaggagtaga    8040
atggaaaagg ggatcggaaa acaagtatat aggaggagac ctatttatgg cttcagaaaa    8100
agacgcagga aaacagtcag cagtaaagct tgttccattg cttattactg tcgctgtggg    8160
actaatcatc tggtttattc ccgctccgtc cggacttgaa cctaaagctt ggcatttgtt    8220
tgcgattttt gtcgcaacaa ttatcggctt tatctccaag cccttgccaa tgggtgcaat    8280
tgcaattttt gcattggcgg ttactgcact aactggaaca ctatcaattg aggatacatt    8340
aagcggattc gggaataaga ccatttggct tatcgttatc gcattcttta tttcccgggg    8400
atttatcaaa accggtctcg gtgcgagaat tcgtatgta ttcgttcaga aattcggaaa     8460 aaaaacccctt ggactttctt attcactgct attcagtgat ttaatacttt cacctgctat   8520
tccaagtaat acggcgcgtg caggaggcat tatatttcct attatcagat cattatccga    8580
aacattcgga tcaagcccgg caaatggaac agagagaaaa atcggtgcat tcttattaaa    8640
aaccggtttt caggggaatc tgatcacatc tgctatgttc ctgacagcga tggcggcgaa    8700
cccgctgatt gccaagctgg cccatgatgt cgcaggggtg gacttaacat ggacaagctg    8760
ggcaattgcc gcgattgtac cgggacttgt aagcttaatc atcacgccgc ttgtgattta    8820
caaactgtat ccgccggaaa tcaaagaaac accggatgcg gcgaaaatcg caacagaaaa    8880
actgaaagaa atgggaccgt tcaaaaaatc ggagctttcc atggttatcg tgtttctttt    8940
ggtgcttgtg ctgtggattt ttggcggcag cttcaacatc gacgctacca caaccgcatt    9000
gatcggtttg gccgttctct tattatcaca agttctgact tgggatgata tcaagaaaga    9060
acagggcgct tgggatacgc tcacttggtt tgcggcgctt gtcatgctcg ccaacttctt    9120
gaatgaatta ggcatggtgt cttggttcag taatgccatg aaatcatccg tatcagggtt    9180
ctcttggatt gtggcattca tcattttaat tgttgtgtat tattactctc actatttctt    9240
tgcaagtgcg acagcccaca tcagtgcgat gtattcagca ttttggctg tcgtcgtggc     9300 agcgggcgca ccgccgcttt tagcagcgct gagcctcgcg ttcatcagca acctgttcgg    9360
gtcaacgact cactacggtt ctggagcggc tccggtcttc ttcggagcag gctacatccc    9420
gcaaggcaaa tggtggtcca tcggatttat cctgtcgatt gttcatatca tcgtatggct    9480
tgtgatcggc ggattatggt ggaaagtact aggaatatgg tagaaagaaa aaggcagacg    9540
cggtctgcct ttttttatt tcactccttc gtaagaaaat ggattttgaa aaatgagaaa     9600
attccctgtg aaaaatggta tgatctaggt agaaaggacg gctggtgctg tggtgaaaaa    9660
```
gcggttccat ttttccct                                                      9678

<210> SEQ ID NO 13
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid

<400> SEQUENCE: 13

His Gly Thr Xaa Xaa Xaa Xaa Xaa Xaa Ala Ser Tyr Gly Ser Val Ser
1               5                   10                  15

Gly

<210> SEQ ID NO 14
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(11)
<223> OTHER INFORMATION: Xaa can be any naturally occurring amino acid

<400> SEQUENCE: 14

His Gly Thr Xaa Xaa Xaa Xaa Xaa Xaa Xaa Tyr Gly Ser Val Ser
1               5                   10                  15

Gly

<210> SEQ ID NO 15
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 15

His Gly Thr Xaa Xaa Xaa Xaa Xaa Xaa Xaa Ser Xaa Gly Ser Val Ser
1               5                   10                  15

Gly

<210> SEQ ID NO 16
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 16

His Gly Thr Xaa Xaa Xaa Xaa Xaa Xaa Xaa Ser Tyr Xaa Ser Val Ser
1               5                   10                  15

Gly

<210> SEQ ID NO 17
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 17

His Gly Thr Xaa Xaa Xaa Xaa Xaa Xaa Xaa Ser Tyr Gly Xaa Val Ser
1               5                   10                  15

Gly

<210> SEQ ID NO 18
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 18

His Gly Thr Xaa Xaa Xaa Xaa Xaa Xaa Xaa Ser Tyr Gly Ser Xaa Ser
1               5                   10                  15

Gly

<210> SEQ ID NO 19
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 19

His Gly Thr Xaa Xaa Xaa Xaa Xaa Xaa Xaa Ser Tyr Gly Ser Val Xaa
1               5                   10                  15

Gly

<210> SEQ ID NO 20

```
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(10)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 20

His Gly Thr Xaa Xaa Xaa Xaa Xaa Xaa Xaa Ser Tyr Gly Ser Val Ser
1               5                   10                  15

Xaa

<210> SEQ ID NO 21
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 21

His Gly Thr Xaa Xaa Xaa Xaa Xaa Xaa Ala Xaa Xaa Gly Ser Val Ser
1               5                   10                  15

Gly

<210> SEQ ID NO 22
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 22

His Gly Thr Xaa Xaa Xaa Xaa Xaa Xaa Ala Xaa Tyr Xaa Ser Val Ser
1               5                   10                  15

Gly

<210> SEQ ID NO 23
<211> LENGTH: 17
<212> TYPE: PRT
<213> ORGANISM: Artificial
<220> FEATURE:
<223> OTHER INFORMATION: Motif
<220> FEATURE:
```

```
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 23

His Gly Thr Xaa Xaa Xaa Xaa Xaa Xaa Ala Xaa Tyr Gly Xaa Val Ser
1               5                   10                  15

Gly

<210> SEQ ID NO 24
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 24

His Gly Thr Xaa Xaa Xaa Xaa Xaa Xaa Ala Xaa Tyr Gly Ser Xaa Ser
1               5                   10                  15

Gly

<210> SEQ ID NO 25
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 25

His Gly Thr Xaa Xaa Xaa Xaa Xaa Xaa Ala Xaa Tyr Gly Ser Val Xaa
1               5                   10                  15

Gly

<210> SEQ ID NO 26
<211> LENGTH: 17
<212> TYPE: PRT
<213> ORGANISM: Artificial
<220> FEATURE:
```

```
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 26

His Gly Thr Xaa Xaa Xaa Xaa Xaa Xaa Ala Xaa Tyr Gly Ser Val Ser
1               5                   10                  15

Xaa

<210> SEQ ID NO 27
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 27

His Gly Thr Xaa Xaa Xaa Xaa Xaa Xaa Ala Ser Xaa Xaa Ser Val Ser
1               5                   10                  15

Gly

<210> SEQ ID NO 28
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 28

His Gly Thr Xaa Xaa Xaa Xaa Xaa Xaa Ala Ser Xaa Gly Xaa Val Ser
1               5                   10                  15

Gly

<210> SEQ ID NO 29
<211> LENGTH: 17
<212> TYPE: PRT
<213> ORGANISM: Artificial
<220> FEATURE:
<223> OTHER INFORMATION: Motif
<220> FEATURE:
```

```
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 29

His Gly Thr Xaa Xaa Xaa Xaa Xaa Xaa Ala Ser Xaa Gly Ser Xaa Ser
1               5                   10                  15

Gly

<210> SEQ ID NO 30
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 30

His Gly Thr Xaa Xaa Xaa Xaa Xaa Xaa Ala Ser Xaa Gly Ser Val Xaa
1               5                   10                  15

Gly

<210> SEQ ID NO 31
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 31

His Gly Thr Xaa Xaa Xaa Xaa Xaa Xaa Ala Ser Xaa Gly Ser Val Ser
1               5                   10                  15

Xaa

<210> SEQ ID NO 32
<211> LENGTH: 17
<212> TYPE: PRT
<213> ORGANISM: Artificial
<220> FEATURE:
```

<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid

<400> SEQUENCE: 32

His Gly Thr Xaa Xaa Xaa Xaa Xaa Xaa Ala Ser Tyr Xaa Xaa Val Ser
1               5                   10                  15

Gly

<210> SEQ ID NO 33
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 33

His Gly Thr Xaa Xaa Xaa Xaa Xaa Xaa Ala Ser Tyr Xaa Ser Xaa Ser
1               5                   10                  15

Gly

<210> SEQ ID NO 34
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 34

His Gly Thr Xaa Xaa Xaa Xaa Xaa Xaa Ala Ser Tyr Xaa Ser Val Xaa
1               5                   10                  15

Gly

<210> SEQ ID NO 35
<211> LENGTH: 17
<212> TYPE: PRT
<213> ORGANISM: Artificial
<220> FEATURE:
<223> OTHER INFORMATION: Motif
<220> FEATURE:

```
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 35

His Gly Thr Xaa Xaa Xaa Xaa Xaa Xaa Ala Ser Tyr Xaa Ser Val Ser
1               5                   10                  15

Xaa

<210> SEQ ID NO 36
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 36

His Gly Thr Xaa Xaa Xaa Xaa Xaa Xaa Ala Ser Tyr Gly Xaa Xaa Ser
1               5                   10                  15

Gly

<210> SEQ ID NO 37
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 37

His Gly Thr Xaa Xaa Xaa Xaa Xaa Xaa Ala Ser Tyr Gly Xaa Val Xaa
1               5                   10                  15

Gly

<210> SEQ ID NO 38
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
```

```
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 38

His Gly Thr Xaa Xaa Xaa Xaa Xaa Xaa Ala Ser Tyr Gly Xaa Val Ser
1               5                   10                  15

Xaa

<210> SEQ ID NO 39
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid

<400> SEQUENCE: 39

His Gly Thr Xaa Xaa Xaa Xaa Xaa Xaa Ala Ser Tyr Gly Ser Xaa Xaa
1               5                   10                  15

Gly

<210> SEQ ID NO 40
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 40

His Gly Thr Xaa Xaa Xaa Xaa Xaa Xaa Ala Ser Tyr Gly Ser Xaa Ser
1               5                   10                  15

Xaa

<210> SEQ ID NO 41
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
```

```
<221> NAME/KEY: misc_feature
<222> LOCATION: (16)..(17)
<223> OTHER INFORMATION: Xaa can be any naturally occurring amino acid

<400> SEQUENCE: 41

His Gly Thr Xaa Xaa Xaa Xaa Xaa Xaa Ala Ser Tyr Gly Ser Val Xaa
1               5                   10                  15

Xaa

<210> SEQ ID NO 42
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(10)
<223> OTHER INFORMATION: Xaa can be any naturally occurring amino acid

<400> SEQUENCE: 42

His Gly Thr Xaa Xaa Xaa Xaa Xaa Xaa Xaa Ser Tyr Gly Ser Val Ser
1               5                   10                  15

Gly

<210> SEQ ID NO 43
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 43

His Gly Thr Xaa Xaa Xaa Xaa Xaa Xaa Ala Xaa Tyr Gly Ser Val Ser
1               5                   10                  15

Gly

<210> SEQ ID NO 44
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 44

His Gly Thr Xaa Xaa Xaa Xaa Xaa Xaa Ala Ser Xaa Gly Ser Val Ser
1               5                   10                  15

Gly

<210> SEQ ID NO 45
<211> LENGTH: 17
```

```
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 45

His Gly Thr Xaa Xaa Xaa Xaa Xaa Xaa Ala Ser Tyr Xaa Ser Val Ser
1               5                   10                  15

Gly

<210> SEQ ID NO 46
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 46

His Gly Thr Xaa Xaa Xaa Xaa Xaa Xaa Ala Ser Tyr Gly Xaa Val Ser
1               5                   10                  15

Gly

<210> SEQ ID NO 47
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 47

His Gly Thr Xaa Xaa Xaa Xaa Xaa Xaa Ala Ser Tyr Gly Ser Xaa Ser
1               5                   10                  15

Gly

<210> SEQ ID NO 48
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
```

```
<222> LOCATION: (16)..(16)
<223> OTHER INFORMATION: Xaa can be any naturally occurring amino acid

<400> SEQUENCE: 48

His Gly Thr Xaa Xaa Xaa Xaa Xaa Xaa Ala Ser Tyr Gly Ser Val Xaa
1               5                   10                  15

Gly

<210> SEQ ID NO 49
<211> LENGTH: 17
<212> TYPE: PRT
<213> ORGANISM: Artificial
<220> FEATURE:
<223> OTHER INFORMATION: Motif
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 49

His Gly Thr Xaa Xaa Xaa Xaa Xaa Xaa Ala Ser Tyr Gly Ser Val Ser
1               5                   10                  15

Xaa

<210> SEQ ID NO 50
<211> LENGTH: 19
<212> TYPE: PRT
<213> ORGANISM: Bacillus amyloliquefaciens

<400> SEQUENCE: 50

His Gly Thr His Val Ala Gly Thr Val Ala Ala Leu Asn Asn Ser Ile
1               5                   10                  15

Gly Val Leu

<210> SEQ ID NO 51
<211> LENGTH: 19
<212> TYPE: PRT
<213> ORGANISM: Bacillus licheniformis

<400> SEQUENCE: 51

His Gly Thr His Val Ala Gly Thr Val Ala Ala Leu Asp Asn Thr Thr
1               5                   10                  15

Gly Val Leu

<210> SEQ ID NO 52
<211> LENGTH: 19
<212> TYPE: PRT
<213> ORGANISM: Bacillus lentus

<400> SEQUENCE: 52

His Gly Thr His Val Ala Gly Thr Ile Ala Ala Leu Asn Asn Ser Ile
1               5                   10                  15

Gly Val Leu
```

POLYPEPTIDES HAVING PROTEASE ACTIVITY AND POLYNUCLEOTIDES ENCODING SAME

CROSS-REFERENCE TO RELATED APPLICATIONS

This application is a continuation of U.S. application Ser. No. 14/125,645 filed Mar. 11, 2014, now pending, which is a 35 U.S.C. 371 national application of international application no. PCT/EP2012/062144 filed Jun. 22, 2012, which claims priority or the benefit under 35 U.S.C. 119 of European application no. 1117317.8 filed Jun. 24, 2011 and U.S. provisional application No. 61/501,319 filed Jun. 27, 2011. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having protease activity and polynucleotides encoding the polypeptides. The invention also relates to nucleic acid constructs, vectors, and host cells comprising the polynucleotides as well as methods of producing and using the polypeptides.

Description of the Related Art

The present invention provides polypeptides having protease activity and polynucleotides encoding the polypeptides.

The detergent industry has for more than 30 years implemented different enzymes in detergent formulations, most commonly used enzymes includes proteases, amylases and lipases each adapted for removing various types of stains. In addition to the enzymes detergent compositions typically include a complex combination of ingredients. For example, most cleaning products include surfactant system, bleaching agents or builders. Despite the complexity of current detergents, there remains a need for developing new detergent compositions comprising new enzymes and/or enzyme blends.

Traditionally laundering has been done at elevated temperatures and well known detergents have been selected to perform at higher temperatures, typically in the range of 40-60° C.

The increased focus on improving the washing processes in order to make them more environmental friendly has resulted in a global tendency to lowering wash time, pH and temperature, decreasing the amount of detergent components which may influence the environment negatively.

There is therefore a desire to launder at lower temperature and therefore a need for detergent proteases having high performance at low temperatures.

The present invention is directed to these and other important ends.

SUMMARY OF THE INVENTION

The present invention relates to isolated polypeptides having protease activity selected from the group consisting of:

(a) a polypeptide having at least 60% sequence identity to the mature polypeptide of SEQ ID NO: 2 or 4;

(b) a polypeptide encoded by a polynucleotide that hybridizes under medium-high stringency conditions with (i) the mature polypeptide coding sequence of SEQ ID NO: 1 or 3, (ii) the mature polypeptide coding sequence of SEQ ID NO: 1 or 3, or (iii) the full-length complementary strand of (i) or (ii);

(c) a polypeptide encoded by a polynucleotide having at least 60% sequence identity to the mature polypeptide coding sequence of SEQ ID NO: 1 or 3;

(d) a variant comprising a substitution, deletion, and/or insertion of one or more (several) amino acids of the mature polypeptide of SEQ ID NO: 2 or 4; and (e) a fragment of a polypeptide of (a), (b), (c) or (d) that has protease activity.

The present invention also relates to isolated polypeptides comprising a catalytic domain selected from the group consisting of:

(a) a catalytic domain having at least 60% sequence identity to amino acids 7 to 270 of SEQ ID NO: 2;

(b) a catalytic domain encoded by a polynucleotide that hybridizes under medium stringency conditions with (i) nucleotides 729 to 1520 of SEQ ID NO: 1, (ii) the cDNA sequence encoding the catalytic domain of SEQ ID NO: 1, or (iii) the full-length complementary strand of (i) or (ii);

(c) a catalytic domain encoded by a polynucleotide having at least 60% sequence identity to the catalytic domain of SEQ ID NO: 1;

(d) a variant of a catalytic domain comprising a substitution, deletion, and/or insertion of one or more (several) amino acids of the catalytic domain of SEQ ID NO: 2; and (e) a fragment of a catalytic domain of (a), (b), (c), or (d) that has protease activity.

In another embodiment, the present invention relates to isolated polypeptides having protease activity, comprising the following motif:

```
                                    (SEQ ID NO: 13)
His Gly Thr (Xaa)6 Ala Ser Tyr Gly Ser Val Ser Gly
``` wherein Xaa is any natural amino acid and $(Xaa)_6$ mean 6 consecutive amino acids, where each amino acid may be any natural amino acid, or the corresponding motif comprising one or two substitutions among the last 8 amino acids in the motif.

The present invention also relates to composition comprising the polypeptides of the invention, in particular detergent compositions comprising the protease of the invention, such as detergent composition for laundry or for manual or automatic dishwash.

The present invention also relates to method for laundering textiles using a composition comprising the polypeptide of the invention, and to methods for cleaning hard surfaces.

The present invention also relates to a polynucleotide encoding a signal peptide comprising or consisting of amino acids −169 to −144 of SEQ ID NO: 2 or −160 to −132 of SEQ ID NO 4, a polynucleotide encoding a propeptide comprising or consisting of amino acids −143 to −1 of SEQ ID NO: 2 or amino acids −131 to −1 of SEQ ID NO 4, or a polynucleotide encoding a signal peptide and a propeptide comprising or consisting of amino acids −169 to −144 and −143 to −1 of SEQ ID NO: 2 or amino acids −160 to −132 and −131 to −1 of SEQ ID NO 4 respectively, each of which is operably linked to a gene encoding a protein; to nucleic acid constructs, expression vectors, and recombinant host cells comprising the polynucleotides; and to methods of producing a protein.

Overview of Sequence Listing

SEQ ID NO: 1 is the DNA sequence of the S8 protease as isolated from *Bacillus* sp. NN018132.

SEQ ID NO: 2 is the amino acid sequence as deduced from SEQ ID NO: 1.

SEQ ID NO: 3 is the DNA sequence of the S8 protease as isolated from *Bacillus borgouniensis*.

SEQ ID NO: 4 is the amino acid sequence as deduced from SEQ ID NO: 3.

SEQ ID NO: 5 is the DNA sequence of the S8 protease from *Paenibacillus dendritiformis* having the accession number EMBL:GQ891986.

SEQ ID NO: 6 is the amino acid public sequence of the *Paenibacillus dendritiformis* protease having the accession number SWISSPROT:D0EVD2.

SEQ ID NO: 7 and 8 are primers for amplifying *Bacillus* sp. NN018132.

SEQ ID NO: 9 and 10 are primers for amplifying *Bacillus borgouniensis*.

SEQ ID NO: 11 is the fused fragment of *Bacillus* sp. NN018132.

SEQ ID NO: 12 is the fused fragment of *Bacillus borgouniensis*.

SEQ ID NO: 13 to SEQ ID NO: 49 are motif sequences.

Definitions

Protease activity: The term "protease activity" means a proteolytic activity (EC 3.4.21.) that catalyzes the hydrolysis of amide bond or a protein by hydrolysis of the peptide bond that link amin acids together in a polypeptide chain. Several assays for determining protease activity is available in the art. For purposes of the present invention, protease activity may be determined using Protazyme AK tablet (cross-linked and dyed casein; from Megazyme) or in the Suc-AAPF-pNA assay as described in the Example section of the present application.

The polypeptides of the present invention have at least 20%, e.g., at least 40%, at least 50%, at least 60%, at least 70%, at least 80%, at least 90%, at least 95%, and at least 100% of the protease activity of the mature polypeptide of SEQ ID NO: 2 or 4.

Isolated polypeptide: The term "isolated polypeptide" means a polypeptide that is modified by the hand of man relative to that polypeptide as found in nature, whereby it has been completely or partially separated from at least one other compound with which the polypeptide is found in nature. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance)

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 275 of SEQ ID NO: 2. In another aspect the mature polypeptide is amino acids 1 to 275 of SEQ ID NO: 4. In another aspect the mature polypeptide is amino acids 1 to 283 of SEQ ID NO: 6.

Propeptide: The term "propeptide" means a polypeptide that is translated together with the mature polypeptide and are cleaved of before the mature polypeptide is released and obtain protease activity. In one aspect the propeptide is amino acids −143 to −1 of SEQ ID NO: 2, −131 to −1 of SEQ ID NO: 4 or −128 to −1 of SEQ ID NO: 6.

Signal peptide: The term "Signal peptide" means a short polypeptide that is translated together with the mature polypeptide and the propeptide is present. The signal peptide is located in the N-terminus of the translated polypeptide and is responsible for the secretion of the polypeptide. Usually, the signal peptide is removed during translocation of the polypeptide across a membrane, such as a plasma membrane or the membrane of the endoplasmatic reticulum.

Signal peptides are well known in the art and several methods for predicting signal peptides have been developed, e.g., SignalP (Nielsen et al., 1997, *Protein Engineering* 10: 1-6), which predicts that amino acids −169 to −144 of SEQ ID NO: 2, −160 to −132 of SEQ ID NO: 4 and −158 to −129 of SEQ ID NO: 6 are signal peptides.

Mature polypeptide coding sequence: The term "mature polypeptide coding sequence" means a polynucleotide that encodes a mature polypeptide having protease activity. In one aspect, the mature polypeptide coding sequence is nucleotides 711 to 1535 of SEQ ID NO: 1, 581 to 1405 of SEQ ID NO: 3 or 475 to 1323 of SEQ ID NO: 5.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the —nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment)

Fragment: The term "fragment" means a polypeptide having one or more (several) amino acids deleted from the amino and/or carboxyl terminus of a mature polypeptide; wherein the fragment has protease activity. In one aspect, a fragment contains at least 200 amino acid residues (e.g., amino acids 160 to 360 of SEQ ID NO: 2, 4 or 6), at least 230 amino acid residues (e.g., amino acids 150 to 380 of SEQ ID NO: 2, 4 or 6), and at least 260 amino acid residues (e.g., amino acids 150 to 410 of SEQ ID NO: 2, 4 or 6.

Subsequence: The term "subsequence" means a polynucleotide having one or more (several) nucleotides deleted from the 5' and/or 3' end of a mature polypeptide coding sequence; wherein the subsequence encodes a fragment having protease activity. In one aspect, a subsequence contains at least 600 nucleotides (e.g., nucleotides 759 to 1361 of SEQ ID NO: 1, 3 or 5), e.g., at least 700 nucleotides (e.g., nucleotides 731 to 1431 of SEQ ID NO: 1, 3 or 5) and at least 780 nucleotides (e.g., nucleotides 731 to 1514 of SEQ ID NO: 1, 3 or 5.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" means a polynucleotide that is modified by the hand of man relative to that polynucleotide as found in nature whereby it has been completely or partially separated from at least one other compound with which the polypeptide is found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" means all components necessary for the expression of a polynucleotide encoding a polypeptide of the present invention. Each control sequence may be native or foreign to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Operably linked: The term "operably linked" means a configuration in which a control sequence is placed at an appropriate position relative to the coding sequence of a polynucleotide such that the control sequence directs the expression of the coding sequence.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

Low stringency conditions: The term "low stringency conditions" means for probes of at least 100 nucleotides in length, prehybridization and hybridization at 42° C. in 5× SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Medium stringency conditions: The term "medium stringency conditions" means for probes of at least 100 nucleotides in length, prehybridization and hybridization at 42° C. in 5× SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2× SSC, 0.2% SDS at 55° C.

High stringency conditions: The term "high stringency conditions" means for probes of at least 100 nucleotides in length, prehybridization and hybridization at 42° C. in 5× SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2× SSC, 0.2% SDS at 65° C.

Cleaning compositions: The terms "cleaning compositions" and "cleaning formulations," refer to compositions that find use in the removal of undesired compounds from items to be cleaned, such as fabric, carpets, dishware including glassware, contact lenses, hard surfaces such as tiles, zincs, floors, and table surfaces, hair (shampoos), skin (soaps and creams), teeth (mouthwashes, toothpastes), etc. The terms encompass any materials/compounds selected for the particular type of cleaning composition desired and the form of the product (e.g., liquid, gel, granule, or spray compositions), as long as the composition is compatible with the metalloprotease and other enzyme(s) used in the composition. The specific selection of cleaning composition materials is readily made by considering the surface, item or fabric to be cleaned, and the desired form of the composition for the cleaning conditions during use. These terms further refer to any composition that is suited for cleaning, bleaching, disinfecting, and/or sterilizing any object and/or surface. It is intended that the terms include, but are not limited to detergent composition (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Detergent composition: The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. It is intended that in addition to the Thermolysin-Like Metalloprotease according to the invention, the term encompasses detergents that contains, e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

Fabric: The term, "fabric" encompasses any textile material. Thus, it is intended that the term encompass garments, as well as fabrics, yarns, fibers, non-woven materials, natural materials, synthetic materials, and any other textile material.

Textile: The term, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

Non-fabric detergent compositions: The term, "non-fabric detergent compositions" include non-textile surface detergent compositions, including but not limited to dishwashing detergent compositions, oral detergent compositions, denture detergent compositions, and personal cleansing compositions.

Effective amount of enzyme: The term, "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a metalloprotease refers to the quantity of metalloprotease described hereinbefore that achieves a desired level of enzymatic activity, e.g., in a defined detergent composition.

Wash performance: The term, "wash performance" of an enzyme refers to the contribution of an enzyme to washing that provides additional cleaning performance to the detergent without the addition of the enzyme to the composition. Wash performance is compared under relevant washing conditions. Wash performance of enzymes is conveniently measured by their ability to remove certain representative stains under appropriate test conditions. In these test systems, other relevant factors, such as detergent composition, detergent concentration, water hardness, washing mechanics, time, pH, and/or temperature, can be controlled in such a way that conditions typical for household application in a certain market segment are imitated.

Water hardness: The term "water hardness" or "degree of hardness" or "dH" or "°dH" as used herein refers to German degrees of hardness. One degree is defined as 10 milligrams of calcium oxide per litre of water.

Relevant washing conditions: The term "relevant washing conditions" is used herein to indicate the conditions, particularly washing temperature, time, washing mechanics, detergent concentration, type of detergent and water hardness, actually used in households in a detergent market segment.

Improved property: The term "improved property" is used to indicate that a better end result is obtained in a property compared to the same process performed without the enzyme. Exemplary properties which are preferably improved in the processes of the present invention include wash performance, enzyme stability, enzyme activity and substrate specificity.

Improved wash performance: The term "improved wash performance" is used to indicate that a better end result is obtained in stain removal from items washed (e.g., fabrics or dishware and/or cutlery) under relevant washing conditions as compared to no enzyme or to a reference enzyme, or that less enzyme, on weight basis, is needed to obtain the same end result relative to no enzyme or to a reference enzyme. Improved wash performance could in this context also be that the same effect, e.g., stain removal effect is obtained in shorter wash time, e.g., the enzymes provide their effect more quickly under the tested conditions.

The term "retained wash performance" is used to indicate that the wash performance of an enzyme, on weight basis, is at least 80 percent relative to another enzyme under relevant washing conditions.

Enzyme detergency: The term "enzyme detergency" or "detergency" or "detergency effect" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process an effect that also is termed anti-redeposition, restoring fully or partly the whiteness of textiles, which originally were white but after repeated use and wash have obtained a greyish or yellowish appearance an effect that also is termed whitening. Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric an effect that is also termed dye transfer inhibition or anti-back staining, removal of protruding or broken fibers from a fabric surface to decrease pilling tendencies or remove already existing pills or fuzz an effect that also is termed anti-pilling, improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

Anti-redeposition: The term "anti-redeposition" as used herein describes the reduction or prevention of redeposition of soils dissolved or suspended in the wash liquor onto the cleaned objects. Redeposition may be seen after one or multiple washing cycles (e.g., as a greying, yellowing or other discolorations).

Adjunct materials: The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the metalloprotease enzyme used in the composition. In some embodiments, granular compositions are in "compact" form, while in other embodiments, the liquid compositions are in a "concentrated" form.

Stain removing enzyme: The term "stain removing enzyme" as used herein, describes an enzyme that aids the removal of a stain or soil from a fabric or a hard surface. Stain removing enzymes act on specific substrates, e.g., protease on protein, amylase on starch, lipase and cutinase on lipids (fats and oils), pectinase on pectin and hemicellulases on hemicellulose. Stains are often depositions of complex mixtures of different components which either results in a local discoloration of the material by itself or which leaves a sticky surface on the object which may attract soils dissolved in the washing liquor thereby resulting in discoloration of the stained area. When an enzyme acts on its specific substrate present in a stain the enzyme degrades or partially degrades its substrate thereby aiding the removal of soils and stain components associated with the substrate during the washing process. For example, when a chlorophyllase acts on a grass stain it degrades the chlorophyll components in the grass and allows the green/brown colour to be released during washing.

Reduced amount: The term "reduced amount" means in this context that the amount of the component is smaller than the amount which would be used in a reference process under otherwise the same conditions. In a preferred embodiment the amount is reduced by, e.g., at least 5%, such as at least 10%, at least 15%, at least 20% or as otherwise herein described.

Low detergent concentration: The term "low detergent concentration" system includes detergents where less than about 800 ppm of detergent components is present in the wash water. Asian, e.g., Japanese detergents are typically considered low detergent concentration systems.

Medium detergent concentration: The term "medium detergent concentration" system includes detergents wherein between about 800 ppm and about 2000 ppm of detergent components are present in the wash water. North American detergents are generally considered to be medium detergent concentration systems.

High detergent concentration: The term "high detergent concentration" system includes detergents wherein greater than about 2000 ppm of detergent components are present in the wash water. European detergents are generally considered to be high detergent concentration systems.

DETAILED DESCRIPTION OF THE INVENTION

Polypeptides Having Protease Activity

The present invention relates to polypeptides having protease activity characterized in that the protease has high detergency performance at low temperatures and the stability is not affected by the presence of a strong chelator.

Thus, on aspect of the invention relates to isolated polypeptides having protease activity selected from the group consisting of:

(a) a polypeptide having at least 60% sequence identity to the mature polypeptide of SEQ ID NO: 2;

(b) a polypeptide encoded by a polynucleotide that hybridizes under medium stringency conditions with (i) the mature polypeptide coding sequence of SEQ ID NO: 1, (ii) the cDNA sequence comprising the mature polypeptide coding sequence of SEQ ID NO: 1, or (iii) the full-length complementary strand of (i) or (ii);

(c) a polypeptide encoded by a polynucleotide having at least 60% sequence identity to the mature polypeptide coding sequence of SEQ ID NO: 1;

(d) a variant comprising a substitution, deletion, and/or insertion of one or more (several) amino acids of the mature polypeptide of SEQ ID NO: 2; and (e) a fragment of a polypeptide of (a), (b), (c), or (d) that has protease activity.

Another aspect of the invention relates to isolated polypeptides having protease activity selected from the group consisting of:

(a) a polypeptide having at least 60% sequence identity to the mature polypeptide of SEQ ID NO: 4;

(b) a polypeptide encoded by a polynucleotide that hybridizes under medium stringency conditions with (i) the mature polypeptide coding sequence of SEQ ID NO: 3, (ii) the cDNA sequence comprising the mature polypeptide coding sequence of SEQ ID NO: 3, or (iii) the full-length complementary strand of (i) or (ii);

(c) a polypeptide encoded by a polynucleotide having at least 60% sequence identity to the mature polypeptide coding sequence of SEQ ID NO: 3;

(d) a variant comprising a substitution, deletion, and/or insertion of one or more (several) amino acids of the mature polypeptide of SEQ ID NO: 4; and (e) a fragment of a polypeptide of (a), (b), (c), or (d) that has protease activity.

The present invention also relates to isolated polypeptides comprising a catalytic domain selected from the group consisting of:

(a) a catalytic domain having at least 60% sequence identity to amino acids 7 to 270 of SEQ ID NO: 2;

(b) a catalytic domain encoded by a polynucleotide that hybridizes under medium stringency conditions with (i) nucleotides 729 to 1520 of SEQ ID NO: 1, (ii) the genomic DNA sequence comprising the catalytic domain of SEQ ID NO: 1, or (iii) the full-length complementary strand of (i) or (ii);

(c) a catalytic domain encoded by a polynucleotide having at least 60% sequence identity to the catalytic domain of SEQ ID NO: 1;

(d) a variant of a catalytic domain comprising a substitution, deletion, and/or insertion of one or more (several) amino acids of the catalytic domain of SEQ ID NO: 2; and (e) a fragment of a catalytic domain of (a), (b), (c) or (d) that has protease activity.

The present invention relates to isolated polypeptides or catalytic domains having a sequence identity to the mature polypeptide of SEQ ID NO: 2 of at least 60%, e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 2.

The present invention relates to isolated polypeptides having a sequence identity to the mature polypeptide of SEQ ID NO: 4 of at least 60%, e.g., at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 4.

A polypeptide of the present invention preferably comprises or consists of the amino acid sequence of SEQ ID NO: 2 or an allelic variant thereof; or is a fragment thereof having protease activity. A polypeptide of the present invention preferably comprises or consists of the amino acid sequence of SEQ ID NO: 4 or an allelic variant thereof; or is a fragment thereof having protease activity. In another aspect, the polypeptide comprises or consists of the mature polypeptide of SEQ ID NO: 2. In another aspect, the polypeptide comprises or consists of the mature polypeptide of SEQ ID NO: 4. In another preferred aspect, the polypeptide comprises or consists of amino acids 1 to 275 of SEQ ID NO: 2. In another preferred aspect, the polypeptide comprises or consists of amino acids 1 to 275 of SEQ ID NO: 4.

The proteases of the present invention share the motif His Gly Thr (Xaa)$_6$ Ala Ser Tyr Gly Ser Val Ser Gly which is located in a region where most other subtilisins have a high-affinity binding site for Ca2+. The loop of the subtilisins of the present invention are shorter than found in subtilisins with the high-affinity binding site for Ca2+, indicating that the site is not present here, see alignment below. This is also represented by the data showing that their performance is not affected by chelators like EDTA, as demonstrated in Example 3, Table 6. This motif is also found in the protease from *Paenibacillus dendritiformis* (*P. dendrite*) with SEQ ID NO 6.

Motif region as found by ClustalW 1.83 alignment of 3 known subtilsins and SEQ ID NO: 2, 4 and 6.

```
BPN'
                            (SEQ ID NO: 50)
HGTHVAGTVAALNNSIGVL

Alcalase
                            (SEQ ID NO: 51)
HGTHVAGTVAALDNTTGVL

Savinase
                            (SEQ ID NO: 52)
HGTHVAGTIAALNNSIGVL
```

-continued

HGTHVAGTIASYG---SVS    SEQ ID NO: 2

HGTHVAGTIASYG---SVS    SEQ ID NO: 4

HGTHVAGTIASYG---SVS    SEQ ID NO: 6

Thus, in one embodiment the present invention relates to isolated polypeptides comprising the motif His Gly Thr (Xaa)$_6$ Ala Ser Tyr Gly Ser Val Ser Gly (SEQ ID NO: 13) and having a sequence identity to the mature polypeptide of SEQ ID NO: 2 of at least 40%, e.g., at least 50%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity.

In one embodiment, the present invention relates to isolated polypeptides comprising the motif His Gly Thr (Xaa)$_6$ Ala Ser Tyr Gly Ser Val Ser Gly (SEQ ID NO: 13) and having a sequence identity to the mature polypeptide of SEQ ID NO: 4 of at least 40%, e.g., at least 50%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity.

Thus, in one embodiment the present invention relates to isolated polypeptides comprising the motif His Gly Thr (Xaa)6 Ala Ser Tyr Gly Ser Val Ser Gly (SEQ ID NO: 13) and having a sequence identity to the mature polypeptide of SEQ ID NO: 6 of at least 40%, e.g., at least 50%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity.

One aspect of the invention concerns isolated polypeptides comprising the motif His Gly Thr (Xaa)6 Ala Ser Tyr Gly Ser Val Ser Gly (SEQ ID NO: 13) and having a sequence identity to the mature polypeptide of SEQ ID NO: 2, 4 and 6 of at least 60%, e.g., at least 65%, at least 70%, at least 75%, at least 80%, at least 85%, at least 90%, at least 95%, at least 96%, at least 97%, at least 98%, at least 99%, or 100%, which have protease activity.

In another embodiment, the present invention relates to isolated polypeptides having protease activity, comprising the following motif:

(SEQ ID NO: 13)
His Gly Thr (Xaa)$_6$ Ala Ser Tyr Gly Ser Val Ser Gly wherein Xaa is any natural amino acid and (Xaa)$_6$ mean 6 consecutive amino acids, where each amino acid may be any natural amino acid, or the corresponding motif comprising one or two substitutions among the last 8 amino acids in the motif. In particular, the present invention relates to isolated polypeptides having proteas activity, comprising a motif selected among:

(SEQ ID NO: 14)
His Gly Thr-(Xaa)$_6$-Xaa Xaa Tyr Gly Ser Val Ser Gly;

(SEQ ID NO: 15)
His Gly Thr-(Xaa)$_6$-Xaa Ser Xaa Gly Ser Val Ser Gly;

(SEQ ID NO: 16)
His Gly Thr-(Xaa)$_6$-Xaa Ser Tyr Xaa Ser Val Ser Gly;

(SEQ ID NO: 17)
His Gly Thr-(Xaa)$_6$-Xaa Ser Tyr Gly Xaa Val Ser Gly;

(SEQ ID NO: 18)
His Gly Thr-(Xaa)$_6$-Xaa Ser Tyr Gly Ser Xaa Ser Gly;

(SEQ ID NO: 19)
His Gly Thr-(Xaa)$_6$-Xaa Ser Tyr Gly Ser Val Xaa Gly;

(SEQ ID NO: 20)
His Gly Thr-(Xaa)$_6$-Xaa Ser Tyr Gly Ser Val Ser Xaa;

(SEQ ID NO: 21)
His Gly Thr-(Xaa)$_6$-Ala Xaa Xaa Gly Ser Val Ser Gly;

(SEQ ID NO: 22)
His Gly Thr-(Xaa)$_6$-Ala Xaa Tyr Xaa Ser Val Ser Gly;

(SEQ ID NO: 23)
His Gly Thr-(Xaa)$_6$-Ala Xaa Tyr Gly Xaa Val Ser Gly;

(SEQ ID NO: 24)
His Gly Thr-(Xaa)$_6$-Ala Xaa Tyr Gly Ser Xaa Ser Gly;

(SEQ ID NO: 25)
His Gly Thr-(Xaa)$_6$-Ala Xaa Tyr Gly Ser Val Xaa Gly;

(SEQ ID NO: 26)
His Gly Thr-(Xaa)$_6$-Ala Xaa Tyr Gly Ser Val Ser Xaa;

(SEQ ID NO: 27)
His Gly Thr-(Xaa)$_6$-Ala Ser Xaa Xaa Ser Val Ser Gly;

(SEQ ID NO: 28)
His Gly Thr-(Xaa)$_6$-Ala Ser Xaa Gly Xaa Val Ser Gly;

(SEQ ID NO: 29)
His Gly Thr-(Xaa)$_6$-Ala Ser Xaa Gly Ser Xaa Ser Gly;

(SEQ ID NO: 30)
His Gly Thr-(Xaa)$_6$-Ala Ser Xaa Gly Ser Val Xaa Gly;

(SEQ ID NO: 31)
His Gly Thr-(Xaa)$_6$-Ala Ser Xaa Gly Ser Val Ser Xaa;

(SEQ ID NO: 32)
His Gly Thr-(Xaa)$_6$-Ala Ser Tyr Xaa Xaa Val Ser Gly;

(SEQ ID NO: 33)
His Gly Thr-(Xaa)$_6$-Ala Ser Tyr Xaa Ser Xaa Ser Gly;

(SEQ ID NO: 34)
His Gly Thr-(Xaa)$_6$-Ala Ser Tyr Xaa Ser Val Xaa Gly;

(SEQ ID NO: 35)
His Gly Thr-(Xaa)$_6$-Ala Ser Tyr Xaa Ser Val Ser Xaa;

-continued

His Gly Thr-(Xaa)₆-Ala Ser Tyr Gly Xaa Xaa Ser Gly; (SEQ ID NO: 36)

His Gly Thr-(Xaa)₆-Ala Ser Tyr Gly Xaa Val Xaa Gly; (SEQ ID NO: 37)

His Gly Thr-(Xaa)₆-Ala Ser Tyr Gly Xaa Val Ser Xaa; (SEQ ID NO: 38)

His Gly Thr-(Xaa)₆-Ala Ser Tyr Gly Ser Xaa Xaa Gly; (SEQ ID NO: 39)

His Gly Thr-(Xaa)₆-Ala Ser Tyr Gly Ser Xaa Ser Xaa; (SEQ ID NO: 40)

His Gly Thr-(Xaa)₆-Ala Ser Tyr Gly Ser Val Xaa Xaa; (SEQ ID NO: 41)

His Gly Thr-(Xaa)₆-Xaa Ser Tyr Gly Ser Val Ser Gly; (SEQ ID NO: 42)

His Gly Thr-(Xaa)₆-Ala Xaa Tyr Gly Ser Val Ser Gly; (SEQ ID NO: 43)

His Gly Thr-(Xaa)₆-Ala Ser Xaa Gly Ser Val Ser Gly; (SEQ ID NO: 44)

His Gly Thr-(Xaa)₆-Ala Ser Tyr Xaa Ser Val Ser Gly; (SEQ ID NO: 45)

His Gly Thr-(Xaa)₆-Ala Ser Tyr Gly Xaa Val Ser Gly; (SEQ ID NO: 46)

His Gly Thr-(Xaa)₆-Ala Ser Tyr Gly Ser Xaa Ser Gly; (SEQ ID NO: 47)

His Gly Thr-(Xaa)₆-Ala Ser Tyr Gly Ser Val Xaa Gly; (SEQ ID NO: 48)
or

His Gly Thr-(Xaa)₆-Ala Ser Tyr Gly Ser Val Ser Xaa. (SEQ ID NO: 49)

Preferably, isolated polypeptides having protease activity according to the invention are selected from the group consisting of:

(a) a polypeptide having at least 60% sequence identity, e.g., at least 65%, at least 70%, at least 75%, at least 80%, at least 85%, at least 90%, at least 95%, at least 96%, at least 97%, at least 98%, at least 99%, or 100%, to the mature polypeptide of SEQ ID NO: 2;

(b) a polypeptide comprising a catalytic domain having at least 60% sequence identity, e.g., at least 65%, at least 70%, at least 75%, at least 80%, at least 85%, at least 90%, at least 95%, at least 96%, at least 97%, at least 98%, at least 99%, or 100%, to the amino acids 7-270 of SEQ ID NO: 2

(c) a polypeptide encoded by a polynucleotide that hybridizes under medium stringency conditions with (i) the mature polypeptide coding sequence of SEQ ID NO: 1, (ii) the cDNA sequence comprising the mature polypeptide coding sequence of SEQ ID NO: 1, or (iii) the full-length complementary strand of (i) or (ii);

(d) a polypeptide encoded by a polynucleotide having at least 60% sequence identity to the mature polypeptide coding sequence of SEQ ID NO: 1;

(e) a variant comprising a substitution, deletion, and/or insertion of one or more (several) amino acids of the mature polypeptide of SEQ ID NO: 2; and (f) a fragment of a polypeptide of (a), (b), (c), (d) or (e) that has protease activity;

wherein the isolated polypeptide having protease activity, comprising the following motif:

His Gly Thr (Xaa)₆ Ala Ser Tyr Gly Ser Val Ser Gly (SEQ ID NO: 13)

wherein Xaa is any natural amino acid and (Xaa)₆ mean 6 consecutive amino acids, where each amino acid may be any natural amino acid, or the corresponding motif comprising one or two substitutions among the last 8 amino acids in the motif.

In another preferably embodiment the isolated polypeptides having protease activity according to the invention are selected from the group consisting of:

(a) a polypeptide having at least 60% sequence identity, e.g., at least 65%, at least 70%, at least 75%, at least 80%, at least 85%, at least 90%, at least 95%, at least 96%, at least 97%, at least 98%, at least 99%, or 100%, to the mature polypeptide of SEQ ID NO: 4;

(b) a polypeptide encoded by a polynucleotide that hybridizes under medium stringency conditions with (i) the mature polypeptide coding sequence of SEQ ID NO: 3, (ii) the cDNA sequence comprising the mature polypeptide coding sequence of SEQ ID NO: 3, or (iii) the full-length complementary strand of (i) or (ii);

(c) a polypeptide encoded by a polynucleotide having at least 60% sequence identity to the mature polypeptide coding sequence of SEQ ID NO: 3;

(d) a variant comprising a substitution, deletion, and/or insertion of one or more (several) amino acids of the mature polypeptide of SEQ ID NO: 4; and (e) a fragment of a polypeptide of (a), (b), (c) or (d) that has protease activity;

wherein the isolated polypeptide having protease activity, comprising the following motif:

His Gly Thr (Xaa)₆ Ala Ser Tyr Gly Ser Val Ser Gly (SEQ ID NO: 13)

wherein Xaa is any natural amino acid and (Xaa)₆ mean 6 consecutive amino acids, where each amino acid may be any natural amino acid, or the corresponding motif comprising one or two substitutions among the last 8 amino acids in the motif.

In yet another preferably embodiment the isolated polypeptides having protease activity according to the invention are selected from the group consisting of:

(a) a polypeptide having at least 60% sequence identity, e.g., at least 65%, at least 70%, at least 75%, at least 80%, at least 85%, at least 90%, at least 95%, at least 96%, at least 97%, at least 98%, at least 99%, or 100%, to the mature polypeptide of SEQ ID NO: 6;

(b) a polypeptide encoded by a polynucleotide that hybridizes under medium stringency conditions with (i) the mature polypeptide coding sequence of SEQ ID NO: 5, (ii) the cDNA sequence comprising the mature polypeptide coding sequence of SEQ ID NO: 5, or (iii) the full-length complementary strand of (i) or (ii);

(c) a polypeptide encoded by a polynucleotide having at least 60% sequence identity to the mature polypeptide coding sequence of SEQ ID NO: 5;

(d) a variant comprising a substitution, deletion, and/or insertion of one or more (several) amino acids of the mature polypeptide of SEQ ID NO: 6; and (e) a fragment of a polypeptide of (a), (b), (c) or (d) that has protease activity;

wherein the isolated polypeptide having protease activity, comprising the following motif:

(SEQ ID NO: 13)
His Gly Thr (Xaa)$_6$ Ala Ser Tyr Gly Ser Val Ser Gly wherein Xaa is any natural amino acid and (Xaa)$_6$ mean 6 consecutive amino acids, where each amino acid may be any natural amino acid, or the corresponding motif comprising one or two substitutions among the last 8 amino acids in the motif.

The polypeptides of the present invention sharing the motif His Gly Thr (Xaa)$_6$ Ala Ser Tyr Gly Ser Val Ser Gly (SEQ ID NO: 13) or any of the motif with SEQ ID NO: 14 to SEQ ID NO: 49 may have the advantage of being stably in the presence of a strong chelator such as EDTA. Thus the stability in the presence of a strong chelator is preferably at least 50% of the stability under same conditions but without chelator, more preferred at least 60%, more preferred at least 70% more preferred at least 80% more preferred at least 90% even more preferred at least 95% and most preferred at least 97%.

This may be determined by assaying the stability of a polypeptide of the invention in the presence of 1 mM EDTA and in the presence of 1 mM CaCl$_2$ but without EDTA, and comparing the stability with and without EDTA. By this assay it is apparent that the stability of the polypeptides in the presence or in the absence of EDTA is almost identical. This is in complete contrast to prior art commercially available proteases such as, e.g., Savinase (alkaline protease derived from Bacillus lentus and available from Novozymes A/S, Copenhagen Denmark), where the stability is significantly lower in the presence of EDTA compared with the stabuility under same conditions but in the absence of EDTA.

The present invention also relates to isolated polypeptides having protease activity that are encoded by polynucleotides that hybridize under very low stringency conditions, low stringency conditions, medium stringency conditions, medium-high stringency conditions, high stringency conditions, or very high stringency conditions with (i) the mature polypeptide coding sequence of SEQ ID NO: 1 or 3, (ii) the genomic DNA sequence encoding the mature polypeptide coding sequence of SEQ ID NO: 1, or (iii) the full-length complementary strand of (i) or (ii) (J. Sambrook, E. F. Fritsch, and T. Maniatis, 1989, Molecular Cloning, A Laboratory Manual, 2d edition, Cold Spring Harbor, N.Y.).

The polynucleotide of SEQ ID NO: 1 or 3 or a subsequence thereof, as well as the amino acid sequence of SEQ ID NO: 2 or 4 or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or 3 or a subsequence thereof, the carrier material is preferably used in a Southern blot.

For purposes of the present invention, hybridization indicates that the polynucleotide hybridizes to a labeled nucleic acid probe corresponding to the mature polypeptide coding sequence of SEQ ID NO: 1 or 3; the genomic DNA sequence comprising the mature polypeptide coding sequence of SEQ ID NO: 1 or 3; its full-length complementary strand; or a subsequence thereof; under very low to very high stringency conditions. Molecules to which the nucleic acid probe hybridizes under these conditions can be detected using, for example, X-ray film.

In one aspect, the nucleic acid probe is the mature polypeptide coding sequence of SEQ ID NO: 1. In another aspect, the nucleic acid probe is nucleotides 711 to 1535 of SEQ ID NO: 1, In one aspect, the nucleic acid probe is the mature polypeptide coding sequence of SEQ ID NO: 3. In another aspect, the nucleic acid probe is nucleotides 581 to 1405 of SEQ ID NO: 3. In another aspect, the nucleic acid probe is a polynucleotide that encodes the polypeptide of SEQ ID NO: 2 or 4 or a fragment thereof. In another preferred aspect, the nucleic acid probe is SEQ ID NO: 1 or 3.

For long probes of at least 100 nucleotides in length, very low to very high stringency conditions are defined as prehybridization and hybridization at 42° C. in 5× SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2× SSC, 0.2% SDS at 45° C. (very low stringency), at 50° C. (low stringency), at 55° C. (medium stringency), at 60° C. (medium-high stringency), at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated T$_m$ using the calculation according to Bolton and McCarthy (1962, Proc. Natl. Acad. Sci. USA 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6× SCC plus 0.1% SDS for 15 minutes and twice each for 15 minutes using 6× SSC at 5° C. to 10° C. below the calculated T$_m$.

The present invention relates to isolated polypeptides having protease activity encoded by polynucleotides having a sequence identity to the mature polypeptide coding sequence of SEQ ID NO: 1 of at least 60%, e.g., at least 65%, at least 70%, at least 75%, at least 80%, at least 85%, at least 90%, at least 95%, at least 96%, at least 97%, at least 98%, at least 99%, or 100%.

The present invention also relates to isolated polypeptides having protease activity encoded by polynucleotides having a sequence identity to the mature polypeptide coding sequence of SEQ ID NO: 3 of at least 60%, e.g., at least 65%, at least 70%, at least 75%, at least 80%, at least 85%, at least 90%, at least 95%, at least 96%, at least 97%, at least 98%, at least 99%, or 100%.

The present invention also relates to variants comprising a substitution, deletion, and/or insertion of one or more (or several) amino acids of the mature polypeptide of SEQ ID NO: 2, 4 or 6, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain. Preferably the variant has at least 60% sequence identity to the mature polypeptide of SEQ ID NO: 2; e.g., at least 65%, at least 70%, at least 75%, at least 80%, at least 85%, at least 90%, at least 95%, at least 96%, at least 97%, at least 98%, at least 99%, but less than 100% identity to the mature polypeptide of SEQ ID NO: 2.

In another preferred embodiment the variant has at least 60% sequence identity to the mature polypeptide of SEQ ID NO: 4; e.g., at least 65%, at least 70%, at least 75%, at least 80%, at least 85%, at least 90%, at least 95%, at least 96%, at least 97%, at least 98%, at least 99%, but less than 100% identity to the mature polypeptide of SEQ ID NO: 4.

In yet another preferred embodiment the variant has at least 60% sequence identity to the mature polypeptide of SEQ ID NO: 6; e.g., at least 65%, at least 70%, at least 75%, at least 80%, at least 85%, at least 90%, at least 95%, at least 96%, at least 97%, at least 98%, at least 99%, but less than 100% identity to the mature polypeptide of SEQ ID NO: 6.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to the parent polypeptide.

The amino acids Asp 176, His 209 and Ser 359 form the catalytic triade of the prosease having SEQ ID NO: 2 and are therefore critical for activity of the molecule and should not be modified. Thus, amino acid residues corresponding to Asp 176, His 209 and Ser 359 in SEQ ID NO: 2 should not be modified in the variants of the invention.

The amino acids Asp 33, His 66 and Ser 216 form the catalytic triade of the prosease having SEQ ID NO: 4 and are therefore critical for activity of the molecule and should not be modified. Thus, amino acid residues corresponding to Asp 33, His 66 and Ser 216 in SEQ ID NO: 2 should not be modified in the variants of the invention.

The amino acids Asp 34, His 67 and Ser 217 form the catalytic triade of the prosease having SEQ ID NO: 6 and are therefore critical for activity of the molecule and should not be modified. Thus, amino acid residues corresponding to Asp 34, His 67 and Ser 217 in SEQ ID NO: 2 should not be modified in the variants of the invention.

The catalytic residues have been determined by alignment with known S8 serine protease where it has been found that the catalytic residues are conserved in all such poroteases.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 2, 4 or 6 are not more than 10, e.g., 1, 2, 3, 4, 5, 6, 7, 8 or 9.

The polypeptide may be hybrid polypeptide in which a portion of one polypeptide is fused at the N-terminus or the C-terminus of a portion of another polypeptide.

The polypeptide may be a fused polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Protease Activity

A polypeptide having protease activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a bacterial polypeptide. For example, the polypeptide may be a gram-positive bacterial polypeptide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* polypeptide having protease activity, or a gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* polypeptide.

In one aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide.

In another aspect, the polypeptide is a *Streptococcus equisimilis*, *Streptococcus pyogenes*, *Streptococcus uberis*, or *Streptococcus equi* subsp. *Zooepidemicus* polypeptide.

In another aspect, the polypeptide is a *Streptomyces achromogenes*, *Streptomyces avermitilis*, *Streptomyces coelicolor*, *Streptomyces griseus*, or *Streptomyces lividans* polypeptide.

The polypeptide may also be a fungal polypeptide. For example, the polypeptide may be a yeast polypeptide such as a *Candida*, *Kluyveromyces*, *Pichia*, *Saccharomyces*, *Schizosaccharomyces*, or *Yarrowia* polypeptide; or a filamentous fungal polypeptide such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide.

In another aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide.

In another aspect, the polypeptide is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* polypeptide.

In one aspect, the polypeptide is a protease from *Bacillus* sp. In another aspect of the invention the polypeptide is a protease from *Bacillus borgouniensis*.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) using the above-mentioned probes. Techniques for isolating microorganisms from natural habitats are well known in the art. The polynucleotide encoding the polypeptide may then be obtained by similarly screening a genomic or cDNA library of another microorganism or mixed DNA sample. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Propeptide

The present invention also relates to isolated polypeptides comprising a propeptide binding domain operably linked to a catalytic domain, wherein the propeptide is selected from the group consisting of:

(a) a propeptide having at least 60% sequence identity to amino acids −143 to −1 of SEQ ID NO: 2, −131 to −1 of SEQ ID NO: 4 or −128 to −1 of SEQ ID NO:6;

(b) a propeptide encoded by a polynucleotide that hybridizes under medium stringency conditions with (i) nucleotides 282 to 710 of SEQ ID NO: 1 or nucleotides 188 to 580 of SEQ ID NO: 3, (ii) the genomic DNA sequence comprising nucleotides 282 to 710 of SEQ ID NO: 1 or nucleotides 188 to 580 of SEQ ID NO: 3 or (iii) the full-length complementary strand of (i) or (ii);

(c) a propeptide encoded by a polynucleotide having at least 60% sequence identity to nucleotides 282 to 710 of SEQ ID NO: 1 or nucleotides 188 to 580 of SEQ ID NO: 3; and (d) a variant comprising a substitution, deletion, and/or insertion of one or more (several) amino acids of amino acids −143 to −1 of SEQ ID NO: 2, −131 to −1 of SEQ ID NO: 4 or −128 to −1 of SEQ ID NO:6.

The propeptide preferably has a degree of sequence identity to amino acids −143 to −1 of SEQ ID NO: 2 of at least 60%, e.g., at least 65%, at least 70%, at least 75%, at least 80%, at least 85%, at least 90%, at least 95%, at least 96%, at least 97%, at least 98%, and at least 99%. In an aspect, the propeptide comprises an amino acid sequence that differs by ten amino acids, e.g., by five amino acids, by four amino acids, by three amino acids, by two amino acids, and by one amino acid from amino acids 1 to 143 of SEQ ID NO: 2.

The propeptide preferably has a degree of sequence identity to amino acids −131 to −1 of SEQ ID NO: 4 of at least 60%, e.g., at least 65%, at least 70%, at least 75%, at least 80%, at least 85%, at least 90%, at least 95%, at least 96%, at least 97%, at least 98%, and at least 99%. In an aspect, the propeptide comprises an amino acid sequence that differs by ten amino acids, e.g., by five amino acids, by four amino acids, by three amino acids, by two amino acids, and by one amino acid from amino acids −131 to −1 of SEQ ID NO: 4.

The propeptide preferably comprises or consists of amino acids −143 to −1 of SEQ ID NO: 2 or an allelic variant thereof.

The propeptide preferably comprises or consists of amino acids −131 to −1 of SEQ ID NO: 4 or an allelic variant thereof.

The propeptide may be encoded by a polynucleotide that hybridizes under very low stringency conditions, low stringency conditions, medium stringency conditions, medium-high stringency conditions, high stringency conditions, and very high stringency conditions (as defined above) with (i) the nucleotides 282 to 710 of SEQ ID NO: 1 or nucleotides 188 to 580 of SEQ ID NO: 3, (ii) the genomic DNA sequence comprising nucleotides 282 to 710 of SEQ ID NO: 1, nucleotides 188 to 580 of SEQ ID NO: 3 or (iii) the full-length complementary strand of (i) or (ii) (J. Sambrook et al., 1989, supra).

The propeptide may be encoded by a polynucleotide having a degree of sequence identity to nucleotides 282 to 710 of SEQ ID NO: 1 of at least 60%, e.g., at least 65%, at least 70%, at least 75%, at least 80%, at least 85%, at least 90%, at least 95%, at least 96%, at least 97%, at least 98%, and at least 99%.

The propeptide may be encoded by a polynucleotide having a degree of sequence identity to nucleotides 188 to 580 of SEQ ID NO: 3 of at least 60%, e.g., at least 65%, at least 70%, at least 75%, at least 80%, at least 85%, at least 90%, at least 95%, at least 96%, at least 97%, at least 98%, and at least 99%.

In another aspect, the polynucleotide encoding the propeptide comprises or consists of nucleotides 282 to 710 of SEQ ID NO: 1.

In another aspect, the polynucleotide encoding the propeptide comprises or consists of nucleotides 188 to 580 of SEQ ID NO: 3.

The propeptide may be a variant comprising a substitution, deletion, and/or insertion of one or more (or several) amino acids of amino acids −143 to −1 of SEQ ID NO: 2. The total number of amino acid substitutions, deletions and/or insertions of amino acids −143 to −1 of SEQ ID NO: 2 is 10, e.g., 1, 2, 3, 4, 5, 6, 8, or 9.

The propeptide may be a variant comprising a substitution, deletion, and/or insertion of one or more (or several) amino acids of amino acids −131 to −1 of SEQ ID NO: 4. The total number of amino acid substitutions, deletions and/or insertions of amino acids −131 to −1 of SEQ ID NO: 4 is 10, e.g., 1, 2, 3, 4, 5, 6, 8, or 9.

The propeptide may be a variant comprising a substitution, deletion, and/or insertion of one or more (or several) amino acids of amino acids −128 to −1 of SEQ ID NO: 6. The total number of amino acid substitutions, deletions and/or insertions of amino acids −128 to −1 of SEQ ID NO: 6 is 10, e.g., 1, 2, 3, 4, 5, 6, 8, or 9.

The catalytic domain may be obtained from an oxidoreductase, transferase, hydrolase, lyase, isomerase, or ligase, e.g., an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase. Preferably the catalytic domain is obtained from a protease, preferably a serine protease, more preferred a subtilisin or a S8-serin protease.

The polynucleotide encoding the catalytic domain may be obtained from any prokaryotic, eukaryotic, or other source.

Polynucleotides

The present invention also relates to isolated polynucleotides encode a polypeptide of the present invention.

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus*, or another or related organism and thus, for example, may be an allelic or species variant of the polypeptide encoding region of the polynucleotide.

The present invention relates to isolated polynucleotides comprising or consisting of polynucleotides having a degree of sequence identity to the mature polypeptide coding sequence of SEQ ID NO: 1 of at least 60%, e.g., at least 65%, at least 70%, at least 75%, at least 80%, at least 85%, at least 90%, at least 95%, at least 96%, at least 97%, at least 98%, at least 99%, or 100%, which encode a polypeptide having protease activity. The present invention also relates to isolated polynucleotides comprising or consisting of polynucleotides having a degree of sequence identity to the mature polypeptide coding sequence of SEQ ID NO: 3 of at least 60%, e.g., at least 65%, at least 70%, at least 75%, at least 80%, at least 85%, at least 90%, at least 95%, at least 96%, at least 97%, at least 98%, at least 99%, or 100%, which encode a polypeptide having protease activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1 or 3 e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

The present invention also relates to isolated polynucleotides encoding polypeptides of the present invention, which hybridize under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii); or allelic variants and subsequences thereof (Sambrook et al., 1989, supra), as defined herein.

The present invention also relates to isolated polynucleotides encoding polypeptides of the present invention, which hybridize under very low stringency conditions, low stringency conditions, medium stringency conditions, medium-high stringency conditions, high stringency conditions, or very high stringency conditions with (i) the mature polypeptide coding sequence of SEQ ID NO: 3, (ii) the genomic DNA sequence comprising the mature polypeptide coding sequence of SEQ ID NO: 3, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 1, the mature polypeptide coding sequence of SEQ ID NO: 1 or a subsequence of SEQ ID NO: 1 that encode a fragment of SEQ ID NO: 2 having protease activity, such as the polynucleotide of nucleotides 711 to 1535 of SEQ ID NO: 1.

In one aspect, the polynucleotide comprises or consists of SEQ ID NO: 3, the mature polypeptide coding sequence of SEQ ID NO: 3 or a subsequence of SEQ ID NO: 3 that encode a fragment of SEQ ID NO: 4 having protease activity, such as the polynucleotide of nucleotides 581 to 1405 of SEQ ID NO: 3.

In another aspect, the polynucleotide comprises or consists of the catalytic domain of nucleotides 729 to 1520 of SEQ ID NO: 1.

In another aspect, the polynucleotide comprises or consists of the propeptide of nucleotides 282 to 710 of SEQ ID NO: 1.

In another aspect, the polynucleotide comprises or consists of the propeptide of nucleotides 188 to 580 of SEQ ID NO: 3.

Nucleic Acid Constructs

The present invention also relates to nucleic acid constructs comprising a polynucleotide of the present invention operably linked to one or more (several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter sequence, a polynucleotide that is recognized by a host cell for expression of a polynucleotide encoding a polypeptide of the present invention. The promoter sequence contains transcriptional control sequences that mediate the expression of the polypeptide. The promoter may be any polynucleotide that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *E. coli* lac operon, *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American,* 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter including a gene encoding a neutral alpha-amylase in Aspergilli in which the untranslated leader has been replaced by an untranslated leader from a gene encoding triose phosphate isomerase in Aspergilli; non-limiting examples include modified promoters including the gene encoding neutral alpha-amylase in *Aspergillus niger* in which the untranslated leader has been replaced by an untranslated leader from the gene encoding triose phosphate isomerase in *Aspergillus nidulans* or *Aspergillus oryzae*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, which is recognized by a host cell to terminate transcription. The terminator sequence is operably linked to the 3'-terminus of the polynucleotide encoding the polypeptide. Any terminator that is functional in the host cell of choice may be used in the present invention.

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, when transcribed is a nontranslated region of an mRNA that is important for translation by the host cell. The leader sequence is operably linked to the 5'-terminus of the polynucleotide encoding the polypeptide. Any leader sequence that is functional in the host cell of choice may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell of choice may be used.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice may be used.

Effective signal peptide coding sequences for bacterial host cells are the signal peptide coding sequences obtained from the genes for *Bacillus* NCI B 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present at the N-terminus of a polypeptide, the propeptide sequence is positioned next to the N-terminus of a polypeptide and the signal peptide sequence is positioned next to the N-terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (several) convenient restriction sites to allow for insertion or substitution of the polynucleotide encoding the polypeptide at such sites. Alternatively, the polynucleotide may be expressed by inserting the polynucleotide or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, chloramphenicol, kanamycin, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished using the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any gram-positive or gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may, for instance, be effected by protoplast transformation (see, e.g., Chang and Cohen, 1979, *Mol. Gen. Genet.* 168: 111-115), by using competent cells (see, e.g., Young and Spizizen, 1961, *J. Bacteriol.* 81: 823-829, or Dubnau and Davidoff-Abelson, 1971, *J. Mol. Biol.* 56: 209-221), by electroporation (see, e.g., Shigekawa and Dower, 1988, *Biotechniques* 6: 742-751), or by conjugation (see, e.g., Koehler and Thorne, 1987, *J. Bacteriol.* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect Immun.* 32: 1295-1297), by protoplast transformation (see, e.g., Catt and Jollick, 1991, *Microbios* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium*

*graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023 and Yelton et al., 1984, *Proc. Natl. Acad. Sci. USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Bacillus*.

The present invention also relates to methods of producing a polypeptide of the present invention, comprising: (a) cultivating a recombinant host cell of the present invention under conditions conducive for production of the polypeptide; and (b) recovering the polypeptide.

The host cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

In an alternative aspect, the polypeptide is not recovered, but rather a host cell of the present invention expressing a polypeptide is used as a source of the polypeptide.

Compositions

The present invention also relates to compositions comprising a polypeptide of the present invention. Preferably, the compositions are enriched in such a polypeptide. The term "enriched" indicates that the protease activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, e.g., *Aspergillus aculeatus, Aspergillus awamori, Aspergillus foetidus, Aspergillus fumigatus, Aspergillus japonicus, Aspergillus nidulans, Aspergillus niger,* or *Aspergillus oryzae; Fusarium*, e.g., *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium suiphureum, Fusarium toruloseum, Fusarium trichothecioides,* or *Fusarium venenatum; Humicola*, e.g., *Humicola insolens* or *Humicola lanuginosa*; or *Trichoderma*, e.g., *Trichoderma harzianum, Trichoderma koningii, Trichoderma longibrachiatum, Trichoderma reesei,* or *Trichoderma viride*.

The compositions may be prepared in accordance with methods known in the art and may be in the form of a liquid or a dry composition. For instance, the composition may be in the form of a granulate or a microgranulate. The polypeptide may be stabilized in accordance with methods known in the art.

Detergent Compositions

In one embodiment, the invention is directed to detergent compositions comprising an enzyme of the present invention in combination with one or more additional cleaning composition components.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product.

Although components mentioned below are categorized by general header according to a particular functionality, this is not to be construed as a limitation, as a component may comprise additional functionalities as will be appreciated by the skilled artisan.

Thus, one embodiment of the invention concerns a detergent composition comprising a polypeptide having a sequence identity to the mature polypeptide of SEQ ID NO: 2 of at least 60%, e.g., at least 65%, at least 70%, at least 75%, at least 80%, at least 85%, at least 90%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 2.

Another embodiment relates to a detergent composition comprising a polypeptide having a sequence identity to the mature polypeptide of SEQ ID NO: 4 of at least 60%, e.g., at least 65%, at least 70%, at least 75%, at least 80%, at least 85%, at least 90%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 4.

Yet another embodiment relates to a detergent composition comprising a polypeptide having a sequence identity to the mature polypeptide of SEQ ID NO: 6 of at least 60%, e.g., at least 65%, at least 70%, at least 75%, at least 80%, at least 85%, at least 90%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 6.

In a preferred embodiment, the composition further comprises at least one other enzyme selected from the group of further proteases, amylases, lipases, cutinases, cellulases, endoglucanases, xyloglucanases, pectinases, pectin lyases, xanthanases, peroxidases, haloperoxygenases, catalases, mannanases, or any mixture thereof.

Enzyme of the Present Invention

In one embodiment of the present invention, the polypeptide of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, most preferably 0.02-2 mg of protein, and even most preferably 0.01-1 mg of protein per liter of wash liquor.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

A polypeptide of the present invention may also be incorporated in the detergent formulations disclosed in WO 97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 1% to about 40% by weight of a cationic surfactant. Non-limiting examples of cationic surfactants include alklydimethylehanolamine quat (ADMEAQ), cetyltrimethylammonium bromide (CTAB), dimethyldistearylammonium chloride (DSDMAC), and alkylbenzyldimethylammonium, and combinations thereof, Alkyl quaternary ammonium compounds, Alkoxylated quaternary ammonium (AQA).

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 1% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 1% to about 40% by weight of a zwitterionic surfactant. Non-limiting examples of zwitterionic surfactants include betaine, alkyldimethylbetaine, and sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however, the molecular structure of hydrotropes generally do not favor spontaneous self-aggregation, see, e.g., review by Hodgdon and Kaler, 2007, *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The detergent composition may also contain 0-65% by weight, such as about 5% to about 40%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N, N-diacetic acid (GLDA), 1-hydroxyethane-1,1-diylbis(phosphonic acid) (HEDP), ethylenediaminetetrakis(methylene)tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N, N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO 2009/102854, U.S. Pat. No. 5,977,053. Incrustation inhibitors such as phosphonates.

Bleaching Systems

The detergent may contain 0-10% by weight, such as about 1% to about 5%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. By Bleach activator is meant herin a compound which reacts with peroxygen bleach like hydrogen peroxide to form a Peracid. The peracid thus formed constitutes the activated bleach. Suitable bleach activators to be used herin include those belonging to the class of esters amides, imides or anhydrides, Suitable examples are tetracetyl athylene diamine (TAED), sodium 3,5,5 trimethyl hexanoyloxybenzene sulphonat, diperoxy dodecanoic acid, 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxy)benzenesulfonate (ISONOBS), tetraacetylethylenediamine (TAED) and 4-(nonanoyloxy) benzenesulfonate (NOBS), and/or those disclosed in WO 98/17767. A particular family of bleach activators of interest was disclosed in EP 624154 and particularly preferred in that family is acetyl triethyl citrate (ATC). ATC or a short chain triglyceride like Triacin has the advantage that it is environmental friendly as it eventually degrades into citric acid and alcohol. Furthermore, acethyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthaloylamino)percapronic acid (PAP). The bleaching system may also include a bleach catalyst. In some embodiments the bleach component may be an organic catalyst selected from the group consisting of organic catalysts having the following formulae:

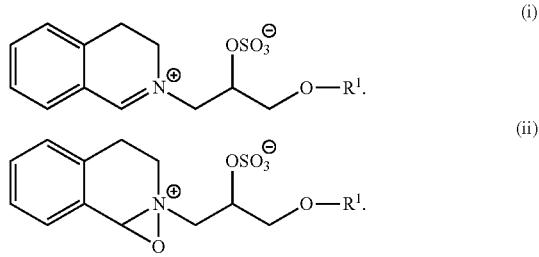

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259, WO 2007/087242. Suitable photobleaches may for example be sulfonated zinc phthalocyanine Polymers The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of polyethylene terephthalate and polyoxyethene terephthalate (PET-POET), PVP, poly(vinylimidazole) (PVI), poly(vinylpyridin-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments which when formulated in detergent compositions can deposit onto a fabric when said fabric is contacted with a wash liquor comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt. % to 0.2 wt. % fabric hueing agent, this may be especially preferred when the composition is in the form of a unit dose pouch. Suitable hueing agents are also disclosed in, e.g., WO 2007/087257, WO 2007/087243.

(Additional) Enzymes

The detergent additive as well as the detergent composition may comprise one or more [additional] enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera Bacillus, Pseudomonas, Humicola, Fusarium, Thielavia, Acremonium, e.g., the fungal cellulases produced from Humicola insolens, Myceliophthora thermophila and Fusarium oxysporum disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™ Primase™, Duralase™, Esperase™, and Kannase™ (Novozymes A/S), Maxatase™, Maxacal™ Maxapem™, Properase™, Purafect™, Purafect OxP™, FN2™, and FN3™ (Genencor International Inc.).

Lipases and Cutinases: Suitable lipases and cutinases include those of bacterial or fungal origin. Chemically modified or protein engineered mutants are included. Examples include lipase from *Thermomyces*, e.g., from *T. lanuginosus* (previously named *Humicola lanuginosa*) as described in EP 258 068 and EP 305 216, cutinase from *Humicola*, e.g., *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochemica et Biophysica Acta, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079, WO 97/07202, WO 00/060063, WO 2007/087508 and WO 2009/109500.

Preferred commercially available lipase enzymes include Lipolase™, Lipolase Ultra™, and Lipex™; Lecitase™, Lipolex™; Lipoclean™, Lipoprime™ (Novozymes A/S). Other commercially available lipases include Lumafast (Genencor Int Inc); Lipomax (Gist-Brocades/Genencor Int Inc) and *Bacillus* sp lipase from Solvay.

Amylases: Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants—The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents—The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent whitening agent—The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxyethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethyl-amino)-s-triazin-6-ylamino) stilbene-2,2'-disulphonate and 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

Soil Release Polymers—The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents—The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, structurants for liquid detergents and/or structure elasticizing agents.

Formulation of Detergent Products

The detergent composition of the invention may be in any convenient form, e.g., a bar, a homogenous tablet, a tablet having two or more layers, a regular or compact powder, a granule, a paste, a gel, or a regular, compact or concentrated liquid.

Detergent formulation forms: Layers (same or different phases), Pouches, versus forms for Machine dosing unit.

Pouches can be configured as single or multicompartments. It can be of any form, shape and material which is suitable for hold the composition, e.g., without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US 2009/0011970).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

Definition/Characteristics of the Forms:

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous, the term non-aqueous is in the present context defined as a water content below 15%, e.g., below 10% or even below 5% of the total volume.

Granular Detergent Formulations

A granular detergent may be formulated as described in WO 2009/092699, EP 1705241, EP 1382668, WO 2007/001262, U.S. Pat. No. 6,472,364, WO 2004/074419 or WO 2009/102854. Other useful detergent formulations are described in WO 2009/124162, WO 2009/124163, WO 2009/117340, WO 2009/117341, WO 2009/117342, WO 2009/072069, WO 2009/063355, WO 2009/132870, WO 2009/121757, WO 2009/112296, WO 2009/112298, WO 2009/103822, WO 2009/087033, WO 2009/050026, WO 2009/047125, WO 2009/047126, WO 2009/047127, WO 2009/047128, WO 2009/021784, WO 2009/010375, WO 2009/000605, WO 2009/122125, WO 2009/095645, WO 2009/040544, WO 2009/040545, WO 2009/024780, WO 2009/004295, WO 2009/004294, WO 2009/121725, WO 2009/115391, WO 2009/115392, WO 2009/074398, WO 2009/074403, WO 2009/068501, WO 2009/065770, WO 2009/021813, WO 2009/030632, WO 2009/015951, WO 2011/025615, WO 2011/016958, WO 2011/005803, WO 2011/005623, WO 2011/005730, WO 2011/005844, WO 2011/005904, WO 2011/005630, WO 2011/005830, WO 2011/005912, WO 2011/005905, WO 2011/005910, WO 2011/005813, WO 2010/135238, WO 2010/120863, WO 2010/108002, WO 2010/111365, WO 2010/108000, WO 2010/107635, WO 2010/090915, WO 2010/033976, WO 2010/033746, WO 2010/033747, WO 2010/033897, WO 2010/033979, WO 2010/030540, WO 2010/030541, WO 2010/030539, WO 2010/024467, WO 2010/024469, WO 2010/024470, WO 2010/025161, WO 2010/014395, WO 2010/044905, WO 2010/145887, WO 2010/142503, WO 2010/122051, WO 2010/102861, WO 2010/099997, WO 2010/084039, WO 2010/076292, WO 2010/069742, WO 2010/069718, WO 2010/069957, WO 2010/057784, WO 2010/054986, WO 2010/018043, WO 2010/003783, WO 2010/003792, WO 2011/023716, WO 2010/142539, WO 2010/118959, WO 2010/115813, WO 2010/105942, WO 2010/105961, WO 2010/105962, WO 2010/094356, WO 2010/084203, WO 2010/078979, WO 2010/072456, WO 2010/069905, WO 2010/076165, WO 2010/072603, WO 2010/066486, WO 2010/066631, WO 2010/066632, WO 2010/063689, WO 2010/060821, WO 2010/049187, WO 2010/031607, WO 2010/000636.

Uses

The present invention is also directed to methods for using the compositions thereof in laundry of textilea and fabrics, such as house hold laundry washing and industrial laundry washing.

The invention is also directed to methods for using the compositions thereof in hard surface cleaning such as automated Dish Washing (ADW), car wash and cleaning of Industrial surfaces.

Use in Detergents.

The polypeptides of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein.

Use of Proteases of the Invention in Detergents

The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In one aspect, the present invention concerns the use of protease of the invention in detergent compositions and cleaning processes, such as laundry and hard surface cleaning. Thus, in one aspect, the present invention demonstrates the detergency effect of a variety of exemplary proteases of the invention on various stains and under various conditions. In a particular aspect of the invention the detergent composition and the use in cleaning process concerns the use of a protease of the invention together with at least one of the above mentioned stain removal enzymes.

In a preferred aspect of the present invention, the protease of the invention useful according to the invention may be combined with at least two enzymes. These additional enzymes are described in details in the section "other enzymes", more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a protease of the invention with another stain removing enzyme, e.g., a protease of the invention and an amylase, a protease of the invention and a cellulase, a protease of the invention and a hemicellulase, a protease of the invention and a lipase, a protease of the invention and a cutinase, a protease of the invention and a pectinase or a protease of the invention and an anti-redeposition enzyme. More preferably, the protease of the invention is combined with at least two other stain removing enzymes, e.g., a protease of the invention, a lipase and an amylase; or a protease of the invention, an amylase and a pectinase; or a protease of the invention, an amylase and a cutinase; or a protease of the invention, an amylase and a cellulase; or a protease of the invention, an amylase and a hemicellulase; or a protease of the invention, a lipase and a pectinase; or a protease of the invention, a lipase and a cutinase; or a protease of the invention, a lipase and a cellulase; or a protease of the invention, a lipase and a hemicellulase. Even more preferably, a protease of the invention may be combined with at least three other stain removing enzymes, e.g., a protease of the invention, an amylase, a lipase and a pectinase; or a protease of the invention, an amylase, a lipase and a cutinase; or a protease of the invention, an amylase, a lipase and a cellulase; or a protease of the invention, an amylase, a lipase and a hemicellulase. A protease of the invention may be combined with any of the enzymes selected from the non-exhaustive list comprising: carbohydrases, such as an amylase, a hemicellulase, a pectinase, a cellulase, a xanthanase or a pullulanase, a peptidase, other proteases or a lipase.

In another embodiment of the present invention, a protease of the invention may be combined with one or more metalloproteases, such as a M4 Metalloprotease, including Neutrase™ or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a detergent composition, and at least one protease of the invention. The cleaning process or a textile care process can for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

The invention further concerns the use of proteases of the invention a proteinaceous stain removing processes. The proteinaceous stains may be stains such as food stains, e.g., baby food, sebum, cocoa, egg, blood, milk, ink, grass, or a combination hereof.

Typical detergent compositions include various components in addition to the enzymes, these components have different effects, some components like the surfactants lower the surface tension in the detergent, which allows the stain being cleaned to be lifted and dispersed and then washed away, other components like bleach systems removes discolor often by oxidation and many bleaches also have strong bactericidal properties, and are used for disinfecting and sterilizing. Yet other components like builder and chelator softens, e.g., the wash water by removing the metal ions form the liquid.

In a particular embodiment, the invention concerns the use of a composition comprising a protease of the invention, wherein said enzyme composition further comprises at least one or more of the following a surfactant, a builder, a chelator or chelating agent, bleach system or bleach component in laundry or dish wash.

In a preferred embodiment of the invention, the amount of a surfactant, a builder, a chelator or chelating agent, bleach system and/or bleach component are reduced compared to amount of surfactant, builder, chelator or chelating agent, bleach system and/or bleach component used without the added protease of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of protease of the invention, such as a conventional amount of such component. In one aspect, the proteases of the invention is used in detergent compositions wherein said composition is free of at least one component which is a surfactant, a builder, a chelator or chelating agent, bleach system or bleach component and/or polymer.

Thus, one embodiment of the invention relates to the use in a detergent or in a cleaning process of a polypeptide having a sequence identity to the mature polypeptide of SEQ ID NO: 2 of at least 60%, e.g., at least 65%, at least 70%, at least 75%, at least 80%, at least 85%, at least 90%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 2.

Another embodiment of the invention relates to the use in a detergent or in a cleaning process of a polypeptide having a sequence identity to the mature polypeptide of SEQ ID NO: 4 of at least 60%, e.g., at least 65%, at least 70%, at least 75%, at least 80%, at least 85%, at least 90%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 4.

A third embodiment of the invention relates to the use in a detergent or in a cleaning process of a polypeptide having a sequence identity to the mature polypeptide of SEQ ID NO: 6 of at least 60%, e.g., at least 65%, at least 70%, at least 75%, at least 80%, at least 85%, at least 90%, at least 95%, at least 96%, at least 97%, at least 98%, at least 99%, or 100%, which have protease activity. In one aspect, the polypeptides differ by no more than ten amino acids, e.g., by five amino acids, by four amino acids, by three amino acids, by two amino acids, and by one amino acid from the mature polypeptide of SEQ ID NO: 6.

Washing Method

The detergent compositions of the present invention are ideally suited for use in laundry applications. Accordingly, the present invention includes a method for laundering a fabric. The method comprises the steps of contacting a fabric to be laundered with a cleaning laundry solution comprising the detergent compositions according to the invention. The fabric may comprise any fabric capable of being laundered in normal consumer use conditions. The solution preferably has a pH of from about 5.5 to about 8. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25°, about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with detergent compositions comprising the proteases of the invention, i.e., proteases with at least 60% identity to SEQ ID NO 2 or SEQ ID NO 4.

A preferred embodiment concerns a method of cleaning, said method comprising the steps of: contacting an object with a cleaning composition comprising a protease of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a protease of the invention under conditions suitable for cleaning said object.

In a preferred embodiment, the compositions for use in the methods above further comprises at least one additional enzyme as set forth in the "other enzymes" section above, such as an enzyme selected from the group consisting of carbohydrases, peptidases, proteases, lipases, cellulase, xylanases or cutinases or a combination hereof. In yet another preferred embodiment the compositions comprises a reduced amount of at least one or more of the following components a surfactant, a builder, a chelator or chelating agent, bleach system or bleach component or a polymer.

Also, contemplated are compositions and methods of treating fabrics (e.g., to desize a textile) using one or more of the proteases of the invention. The proteases can be used in any fabric-treating method which is well known in the art (see, e.g., U.S. Pat. No. 6,077,316). For example, in one aspect, the feel and appearance of a fabric is improved by a method comprising contacting the fabric with proteases in a solution. In one aspect, the fabric is treated with the solution under pressure.

In one embodiment, the proteases are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The proteases can be applied to remove these sizing protein or protein derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. Also provided is a method of desizing comprising enzymatic hydrolysis of the size by the action of an enzyme.

Low Temperature Uses

It was surprising found that the proteases of the present invention—were actually performing relatively better at low temperature, e.g., temperatures of about 40° C. or below than at higher temperatures, e.g., of about 60° C. or above when tested in AMSA as described in the below Examples.

Moreover, in a particularly preferred embodiment the proteases of the invention perform relatively better than a well known subtilisin protease such as Savinase at a wash temperature of about 40° C. or below when tested in AMSA as described herein.

Thus, in one embodiment of the invention concerns a method of doing laundry, dish wash or industrial cleaning comprising contacting a surface to be cleaned with a protease of the invention, and wherein said laundry, dish wash, industrial or institutional cleaning is performed at a temperature of about 40° C. or below. One embodiment of the invention relates to the use of a protease of the invention in laundry, dish wash or a cleaning process wherein the temperature in laundry, dish wash, industrial cleaning is about 40° C. or below.

In another embodiment, the invention concerns the use of a protease of the invention in a protein removing process, wherein the temperature in the protein removing process is about 40° C. or below.

The present invention also relates to the use in laundry, dish wash or industrial cleaning process of a protease of the invention having at least one improved property compared to Savinase and wherein the temperature in laundry, dish wash or cleaning process is performed at a temperature of about 40° C. or below.

In each of the above-identified methods and uses, the wash temperature is about 40° C. or below, such as about 39° C. or below, such as about 38° C. or below, such as about 37° C. or below, such as about 36° C. or below, such as about 35° C. or below, such as about 34° C. or below, such as about 33° C. or below, such as about 32° C. or below, such as about 31° C. or below, such as about 30° C. or below, such as about 29° C. or below, such as about 28° C. or below, such as about 27° C. or below, such as about 26° C. or below, such as about 25° C. or below, such as about 24° C. or below, such as about 23° C. or below, such as about 22° C. or below, such as about 21° C. or below, such as about 20° C. or below, such as about 19° C. or below, such as about 18° C. or below, such as about 17° C. or below, such as about 16° C. or below, such as about 15° C. or below, such as about 14° C. or below, such as about 13° C. or below, such as about 12° C. or below, such as about 11° C. or below, such as about 10° C. or below, such as about 9° C. or below, such as about 8° C. or below, such as about 7° C. or below, such as about 6° C. or below, such as about 5° C. or below, such as about 4° C. or below, such as about 3° C. or below, such as about 2° C. or below, such as about 1° C. or below.

In another preferred embodiment, the wash temperature is in the range of about 5-40° C., such as about 5-30° C., about 5-20° C., about 5-10° C., about 10-40° C., about 10-30° C., about 10-20° C., about 15-40° C., about 15-30° C., about 15-20° C., about 20-40° C., about 20-30° C., about 25-40° C., about 25-30° C., or about 30-40° C. In a particular preferred embodiment, the wash temperature is about 30° C.

In particular embodiments, the low temperature washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the low temperature washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

Signal Peptide and Propeptide

The present invention also relates to an isolated polynucleotide encoding a signal peptide comprising or consisting of amino acids −169 to −144 of SEQ ID NO: 2 or amino acids −160 to −132 of SEQ ID NO: 4. The present invention also relates to an isolated polynucleotide encoding a propeptide comprising or consisting of amino acids −143 to −1 of SEQ ID NO: 2 or amino acids −131 to −1 of SEQ ID NO: 4. The present invention also relates to an isolated polynucleotide encoding a signal peptide and a propeptide comprising or consisting of amino acids −169 to −1 of SEQ ID NO: 2 or amino acids −160 to −1 of SEQ ID NO: 4. The polynucleotides may further comprise a gene encoding a protein, which is operably linked to the signal peptide and/or propeptide. The protein is preferably foreign to the signal peptide and/or propeptide.

The present invention also relates to nucleic acid constructs, expression vectors and recombinant host cells comprising such polynucleotides.

The present invention also relates to methods of producing a protein, comprising: (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides and fused polypeptides.

Preferably, the protein is a hormone or variant thereof, enzyme, receptor or portion thereof, antibody or portion thereof, or reporter. For example, the protein may be an oxidoreductase, transferase, hydrolase, lyase, isomerase, or ligase such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Strains

*Bacillus* sp. 18132, isolated from an environmental sand sample collected in the United States. *Bacillus borgouniensis*, isolated from Indian soil sample. Public sequence *Paenibacillus dendritiformis* strain available from German culture collection (DSMZ, Braunschweig, Germany) as strain DSM 18844.

Wash Assays

Automatic Mechanical Stress Assay (AMSA) for Laundry

In order to assess the wash performance in laundry washing experiments are performed, using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO 02/42740 especially the paragraph "Special method embodiments" at pages 23-24.

The wash performance is measured as the brightness of the colour of the textile washed. Brightness can also be expressed as the intensity of the light reflected from the sample when illuminated with white light. When the sample is stained the intensity of the reflected light is lower, than that of a clean sample. Therefore, the intensity of the reflected light can be used to measure wash performance.

Colour measurements are made with a professional flat-bed scanner (Kodak iQsmart, Kodak, Midtager 29, DK-2605 Brøndby, Denmark), which is used to capture an image of the washed textile.

To extract a value for the light intensity from the scanned images, 24-bit pixel values from the image are converted into values for red, green and blue (RGB). The intensity value (Int) is calculated by adding the RGB values together as vectors and then taking the length of the resulting vector:

$$Int=\sqrt{r^2+g^2+b^2}.$$

Mini Wash Assay for Laundry

Wash performance is assessed in laundry wash experiment using Mini wash assay, which is a test method, where soiled textile continuously is lifted up and down into the test solution and subsequently rinsed.

The washed and rinsed soiled textiles are subsequently air-dried and the wash performance is measured as the brightness of the color of these textiles. Brightness can also be expressed as the Remission (R), which is a measure for the light reflected or emitted from the test material when illuminated with white light. The Remission (R) of the textiles is measured at 460 nm using a Zeiss MCS 521 VIS spectrophotometer. The measurements are done according to the manufacturer's protocol.

TABLE 1

Composition of model detergent and test materials

| | |
|---|---|
| Laundry liquid model detergent B | Water 30.63% |
| | Sodium hydroxide 2.95% |
| | Dodecylbenzensulfonic acid 11.52% |
| | Fatty acids (Soya) 5.50% |
| | Propane-1,2-diol (MPG) 5.05% |
| | Water 17.38% |
| | C13-alcohol ethoxylate, 10.50% |
| | Diethylenetriaminepentakis (methylenephosphonic acid) (DTMPA) 3.08% |
| | Triethanolamine (TEA) 2.22% |
| | Fatty acids (Coco) 4.50% |
| | Sodium citrate monohydrate 1.00% |
| | Ethanol 4.63% |
| | Syntran 5909 (opacifier) 0.30% |
| | Perfume 0.35% |
| Test material | PC-03 (Chocolate-milk/ink on cotton/polyester) |
| | C-10 (Oil/milk/pigment on cotton) |
| | PC-05 (Blood/milk/ink on cotton/polyester) |
| | EMPA117EH (Blood/milk/ink on cotton/polyester) |

Test materials are obtained from Center For Testmaterials BV, P.O. Box 120, 3133 KT Vlaardingen, the Netherlands and EMPA Testmaterials AG, Mövenstrasse 12, CH-9015 St. Gallen, Switzerland.

Enzyme Assays

Protease Assays

1) Suc-AAPF-pNA Assay:
pNA substrate: Suc-AAPF-pNA (Bachem L-1400).
Temperature: Room temperature (25° C.)
Assay buffers: 100 mM succinic acid, 100 mM HEPES, 100 mM CHES, 100 mM CABS, 1 mM CaCl$_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

Assay buffer with 1 mM EDTA: 100 mM succinic acid, 100 mM HEPES, 100 mM CHES, 100 mM CABS, 1 mM EDTA, 150 mM KCl, 0.01% Triton X-100, pH 7.0.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in OD$_{405}$ was monitored as a measure of the protease activity.

2) Protazyme AK Assay:
Substrate: Protazyme AK tablet (cross-linked and dyed casein; from Megazyme)
Temperature: controlled (assay temperature).
Assay buffer: 100 mM succinic acid, 100 mM HEPES, 100 mM CHES, 100 mM CABS, 1 mM CaCl$_2$, 150 mM KCl, 0.01% Triton X-100, pH 7.0.

A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate. OD$_{650}$ was read as a measure of protease activity. A buffer blind was included in the assay (instead of enzyme).

Example 1

Preparation of Protease

Identification of Protease Conding Gene

The alkaliphilic bacterium *Bacillus* sp. 18132 was found to react positive on agar plates containing casein as substrate. For the discovery of the protease gene, the genomic DNA of *Bacillus* sp. 18132 was sequenced and a serine S8 family protease gene having the sequence of SEQ ID NO: 1, was discovered by homology searches in public protein databases, a technique that is known by the person skilled in the art. The encoded protease having SEQ ID NO: 2 was found to be closest related to the public protein sequence from *Paenibacillus dendritiformis* having the accession number SWISSPROT: D0EVD2. The enzyme properties of *Paenibacillus dendritiformis* protease are not known to-date, enzyme properties of *Bacillus* sp. 18132 are disclosed here.

The alkaliphilic bacterium *Bacillus bogoriensis* O1878 was found to react positive on agar plates containing casein as substrate. For the discovery of the protease gene, the genomic DNA of *Bacillus bogoriensis* O1878 was sequenced and a serine S8 family protease gene having the sequence of SEQ ID NO: 3, was discovered by homology searches in public protein databases, a technique that is known by the person skilled in the art. The encoded protease having SEQ ID NO: 4 was found to be closest related to the public protein sequence from *Paenibacillus dendritiformis* having the accession number SWISSPROT: D0EVD2. The enzyme properties of *Paenibacillus dendritiformis* protease are not known to-date, enzyme properties of *Bacillus bogoriensis* O1878 are disclosed here.

The strain *Paenibacillus dendritiformis* DSM18844 was obtained from the German Collection of microorganisms and cell cultures (DSMZ, Braunschweig, Germany) and used as the donor for the above mentioned protease SWIS-SPROT: D0EVD2.

Cloning and Expression of Proteases Bacillus sp. 18132 and Bacillus Borgouniensis The signal peptide from the alkaline protease from *B. clausii* (aprH) was fused by SOE PCR fusion as described in WO 99/43835 (hereby incorporated by reference) in frame to the DNA encoding the protease. To amplify the coding DNA, genomic DNA of *Bacillus* sp. 18132 was used as template and the oligomers C15U1f and C15U1r to amplify the gene by PCR.

```
C15U1f:
                                            (SEQ ID NO: 7)
GTTCATCGATCGCATCGGCTGATGATATGAAGAAAGAAGACTATATTG

C6224f:
                                            (SEQ ID NO: 8)
CCAAGGCCGGTTTTTTATGTTTTATTGTAATCGAAAAGATGTTGTT
```

To amplify the coding DNA, genomic DNA of *Bacillus borgouniensis* was used as template and the oligomers C57J6f and C57J6r to amplify the gene by PCR.

```
Primer C57J6f:
                                            (SEQ ID NO 9)
CTTTTAGTTCATCGATCGCATCGGCTTCGAAAGGTAAAAATAACGGT Primer C57J6r:
                                            (SEQ ID NO 10)
CCAAGGCCGGTTTTTTATGTTTTAGTTTATGACAAAGCTCGT
``` and the derived PCR product was fused to expression cassette elements. The protease gene from *Bacillus* sp. 18132 and *Bacillus borgouniensis* was expressed by control of a triple promoter system consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The expression cassette has been described in WO 99/43835. Furthermore, the expression cassette contained a terminator (term) sequence and a gene coding for chloramphenicol acetyltransferase (cam) which was used as selection maker (as described in (Diderichsen et al., 1993, *Plasmid* 30: 312-315) for *B. subtilis*.

The fused gene fragment (SEQ ID NO: 11 and SEQ ID NO: 12 that was part of the complete expression cassette described above was transformed into *B. subtilis* and the protease gene was integrated into the *Bacillus subtilis* chromosome by homologous recombination into the pectate lyase gene locus (WO 99/43835).

Chloramphenicol resistant transformants were analyzed by DNA sequencing to verify the correct DNA sequence of the construct. The translated protein sequence corresponds to SEQ ID NOs: 2 and 4, where the first 27 amino acids correspond to the *B. clausii* aprH signal peptide, amino acids −143 to −1 are part of a pro-peptide of the protease and amino acids 1-275 correspond to the mature protease S8 domain.

One expression clone was selected and was cultivated on a rotary shaking table in 500 mL baffled Erlenmeyer flasks each containing 100 ml casein based media supplemented with 34 mg/l chloramphenicol. The clone was cultivated for 4 days at 37° C.

Example 2

Purification and Characterization of the Proteases

Purification of the S8A Protease from *Bacillus* sp. NN018132

The culture broth was centrifuged (20000× g, 20 min) and the supernatant was carefully decanted from the precipitate. The supernatant was filtered through a Nalgene 0.2 μm filtration unit in order to remove the rest of the *Bacillus* host cells. Solid ammonium sulphate was added to the 0.2 μm filtrate to a final ammonium sulfate concentration of 1.5 M $(NH_4)_2SO_4$. The solution became slightly turbid and was again filtered through a Nalgene 0.2 μm filtration unit. The clear filtrate was applied to a Phenyl-sepharose FF (high sub) column (from GE Healthcare) equilibrated in 20 mM HEPES, 2 mM $CaCl_2$, 1.5 M $(NH_4)_2SO_4$, pH 7.0. After washing the column extensively with the equilibration buffer, the protease was eluted with a linear gradient over three column volumes between the equilibration buffer and 20 mM HEPES, 2 mM $CaCl_2$, pH 7.0 with 25% (v/v) 2-propanol. Fractions from the column were analyzed for protease activity (using the Suc-AAPF-pNA assay at pH 9). The protease peak was pooled and the pool was transferred to 100 mM $H_3BO_3$, 10 mM MES, 2 mM $CaCl_2$, pH 6.0 on a G25 Sephadex column (from GE Healthcare). The G25 sephadex transferred enzyme was applied to a SP-sepharose FF column (from GE Healthcare) equilibrated in 100 mM $H_3BO_3$, 10 mM MES, 2 mM $CaCl_2$, pH 6.0. After washing the column extensively with the equilibration buffer, the protease was eluted with a linear NaCl gradient (0->0.5 M) in the same buffer over five column volumes. Fractions from the column were analyzed for protease activity (using the Suc-AAPF-pNA assay at pH 9) and active fractions were further analyzed by SDS-PAGE. Fractions, where only one band was seen on the coomassie stained SDS-PAGE gel, were pooled as the purified preparation and was used for further characterization.

Purification of the S8A Protease from *Paenibacillus dendritiformis*

The culture broth was centrifuged (20000× g, 20 min) and the supernatant was carefully decanted from the precipitate. The supernatant was filtered through a Nalgene 0.2 μm filtration unit in order to remove the rest of the *Bacillus* host cells. Solid ammonium sulphate was added to the 0.2 μm filtrate to a final ammonium sulphate concentration of 1.2 M $(NH_4)_2SO_4$. The solution was applied to a SOURCE Phenyl column (from GE Healthcare) equilibrated in 20 mM HEPES, 2 mM $CaCl_2$, 1.2 M $(NH_4)_2SO_4$, pH 7.0. After washing the column extensively with the equilibration buffer, the protease was eluted with a linear gradient over eight column volumes between the equilibration buffer and 20 mM HEPES, 2 mM $CaCl_2$, pH 7.0 with 25% (v/v) 2-propanol. Fractions from the column were analyzed for protease activity (using the Suc-AAPF-pNA assay at pH 9). The protease peak was pooled and the pool was transferred to 20 mM succinic acid/NaOH, 2 mM $CaCl_2$, pH 5.0 on a G25 Sephadex column (from GE Healthcare). The G25 sephadex transferred enzyme was applied to a SP-sepharose FF column (from GE Healthcare) equilibrated in 20 mM succinic acid/NaOH, 2 mM $CaCl_2$, pH 5.0. After washing the column extensively with the equilibration buffer, the protease was eluted with a linear NaCl gradient (0->0.5 M) in the same buffer over five column volumes. Fractions from the column were analyzed for protease activity (using the Suc-AAPF-pNA assay at pH 9) and active fractions were further analyzed by SDS-PAGE. Fractions, where one major dominant band was seen on the coomassie stained SDS-PAGE gel, were pooled and the pool was transferred to 20 mM HEPES, 2 mM CaCl$_2$, pH 7.0 on a G25 Sephadex column (from GE Healthcare). The G25 sephadex transferred protease was the purified preparation and was used for further characterization.

Purification of the S8A Protease from *Bacillus bogoriensis*

The culture broth was centrifuged (20000× g, 20 min) and the supernatant was carefully decanted from the precipitate. The supernatant was filtered through a Nalgene 0.2 μm filtration unit in order to remove the rest of the *Bacillus* host cells. Solid ammonium sulphate was added to the 0.2 μm filtrate to a final ammonium sulphate concentration of 2.0 M (NH$_4$)$_2$SO$_4$. The solution became slightly turbid and was again filtered through a Nalgene 0.2 μm filtration unit. The clear filtrate was applied to a SOURCE Phenyl column (from GE Healthcare) equilibrated in 20 mM HEPES, 2 mM CaCl$_2$, 2.0 M (NH$_4$)$_2$SO$_4$, pH 7.0. After washing the column extensively with the equilibration buffer, the protease was eluted with a linear gradient over eight column volumes between the equilibration buffer and 20 mM HEPES, 2 mM CaCl$_2$, pH 7.0 with 25% (v/v) 2-propanol. Fractions from the column were analyzed for protease activity (using the Suc-AAPF-pNA assay at pH 9). The protease peak was pooled and the pool was transferred to 100 mM H$_3$BO$_3$, 10 mM MES, 2 mM CaCl$_2$, pH 6.0 on a G25 Sephadex column (from GE Healthcare). The G25 sephadex transferred enzyme was applied to a SP-sepharose FF column (from GE Healthcare) equilibrated in 100 mM H$_3$BO$_3$, 10 mM MES, 2 mM CaCl$_2$, pH 6.0. After washing the column extensively with the equilibration buffer, the protease was eluted with a linear NaCl gradient (0-->0.5 M) in the same buffer over five column volumes. Fractions from the column were analyzed for protease activity (using the Suc-AAPF-pNA assay at pH 9) and active fractions were further analyzed by SDS-PAGE. Fractions, where one major dominant band was seen on the coomassie stained SDS-PAGE gel, were pooled and the pool was transferred to 100 mM H$_3$BO$_3$, 10 mM MES, 2 mM CaCl$_2$, pH 6.0 on a G25 Sephadex column (from GE Healthcare). The G25 sephadex transferred protease was the purified preparation and was used for further characterization.

Characterization of the S8A Protease from *Bacillus* sp. NN018132, *Bacillus* Borgouniensis and *Paenibacillus dendritiformis*

The Suc-AAPF-pNA assay was used for obtaining the pH-activity profile and the pH-stability profile (residual activity after 2 hours at indicated pH-values). For the pH-stability profile the protease was diluted 20× in the different Assay buffers to reach the pH-values of these buffers and then incubated for 2 hours at 37° C. After incubation, the pH of the protease incubations was transferred to the same pH-value, before assay for residual activity, by dilution in the pH 9.0 Assay buffer. The Protazyme AK assay was used for obtaining the temperature-activity profile at pH 7.0. The Suc-AAPF-pNA assay was used for obtaining the temperature-stability profiles in Assay buffer, pH 7.0 and in an Assay buffer, pH 7.0 where 1 mM CaCl$_2$ was substituted with 1 mM EDTA. For the temperature-stability profiles the protease was diluted 10× in the Assay buffer, pH 7.0 or in the Assay buffer with 1 mM EDTA, pH 7.0 and then incubated for 15 minutes at the indicated temperatures. After incubation, the residual activity in the samples was measured (Savinase was included as a reference in the temperature-stability experiments).

The results are shown in Tables 2-6 below. For Table 2, the activities are relative to the optimal pH for the enzyme. For Table 3, the activities are residual activities relative to a sample, which was kept at stable conditions (5° C., pH 9.0). For Table 4, the activities are relative to the optimal temperature at pH 7.0 for the enzyme. For Tables 5 and 6, the activities are residual activities relative to the 37° C. samples.

TABLE 2 pH-activity profile

| pH | *Bacillus* sp. NN018132 S8A protease | *Bacillus borgouniensis* S8A protease | *P. dendriti* S8A protease |
|---|---|---|---|
| 2 | 0.00 | 0.00 | 0.00 |
| 3 | 0.00 | 0.00 | 0.00 |
| 4 | 0.00 | 0.00 | 0.00 |
| 5 | 0.01 | 0.01 | 0.01 |
| 6 | 0.06 | 0.06 | 0.10 |
| 7 | 0.30 | 0.29 | 0.45 |
| 8 | 0.78 | 0.78 | 0.94 |
| 9 | 1.00 | 0.97 | 1.00 |
| 10 | 0.90 | 1.00 | 0.86 |
| 11 | 0.66 | 0.75 | 0.71 |

TABLE 3 pH-stability profile (residual activity after 2 hours at 37° C.)

| pH | *Bacillus* sp. NN018132 S8A protease | *Bacillus borgouniensis* S8A protease | *P. dendriti* S8A protease |
|---|---|---|---|
| 2 | 0.00 | 0.00 | 0.00 |
| 3 | 0.00 | 0.00 | 0.00 |
| 4 | 0.00 | 0.00 | 0.00 |
| 5 | 0.21 | 0.20 | 0.94 |
| 6 | 1.03 | 0.87 | 0.98 |
| 7 | 0.93 | 0.94 | 0.99 |
| 8 | 0.99 | 0.89 | 0.98 |
| 9 | 0.93 | 0.88 | 1.00 |
| 10 | 0.97 | 0.99 | 0.97 |
| 11 | 0.92 | 0.97 | 0.97 |
| After 2 hours at 5° C. | 1.00 (at pH 9) | 1.00 (at pH 9) | 1.00 (at pH 9) |

TABLE 4

Temperature activity profile at pH 7

| Temp (° C.) | *Bacillus* sp. NN018132 S8A protease | *Bacillus borgouniensis* S8A protease | *P. dendriti* S8A protease |
|---|---|---|---|
| 15 | 0.02 | 0.01 | 0.00 |
| 25 | 0.04 | 0.01 | 0.00 |
| 37 | 0.17 | 0.10 | 0.03 |
| 50 | 0.71 | 0.39 | 0.17 |
| 60 | 1.00 | 1.00 | 0.49 |
| 70 | 0.15 | 0.22 | 1.00 |
| 80 | 0.08 | 0.09 | 0.17 |

TABLE 5

Temperature-stability profile in buffer pH 7.0 with 1 mM CaCl$_2$ (residual activity after 15 minutes)

| pH Temp (° C.) | *Bacillus* sp. NN018132 S8A protease | *Bacillus borgouniensis* S8A protease | *P. dendriti* S8A protease | Savinase |
|---|---|---|---|---|
| 15 | 0.97 | 1.01 | 1.03 | 1.00 |
| 25 | 0.97 | 1.01 | 1.03 | 0.95 |
| 37 | 1.00 | 1.00 | 1.00 | 1.00 |
| 50 | 1.00 | 0.99 | 1.03 | 0.98 |

TABLE 5-continued

Temperature-stability profile in buffer pH 7.0 with 1 mM CaCl₂ (residual activity after 15 minutes)

| pH Temp (° C.) | Bacillus sp. NN018132 S8A protease | Bacillus borgouniensis S8A protease | P. dendriti S8A protease | Savinase |
|---|---|---|---|---|
| 60 | 0.67 | 0.74 | 1.03 | 0.98 |
| 70 | 0.00 | 0.00 | 0.49 | 0.29 |
| 80 | 0.00 | 0.00 | 0.00 | 0.00 |

TABLE 6

Temperature-stability profile in buffer pH 7.0 with 1 mM EDTA (residual activity after 15 minutes)

| pH Temp (° C.) | Bacillus sp. NN018132 S8A protease | Bacillus borgouniensis S8A protease | P. dendriti S8A protease | Savinase |
|---|---|---|---|---|
| 15 | 1.02 | 0.97 | 1.02 | 1.07 |
| 25 | 1.01 | 0.95 | 0.99 | 1.00 |
| 37 | 1.00 | 1.00 | 1.00 | 1.00 |
| 50 | 1.02 | 0.94 | 0.97 | 0.52 |
| 60 | 0.67 | 0.69 | 0.98 | 0.00 |
| 70 | 0.00 | 0.00 | 0.45 | 0.00 |
| 80 | 0.00 | 0.00 | 0.00 | 0.00 |

Other Characteristics

The S8A protease from Bacillus sp. NN018132, Paenibacillus dendritiformis and Bacillus bogoriensis was inhibited by PMSF.

N-Terminal

The protease was diluted to approximately 1 mg/ml and 100 µl was mixed with 33 µl 50% TCA solution and incubated 5 minutes on ice. The precipitate was harvested by centrifugation 14.000 g in 5 minutes and resuspended in a mixture of 100 µl 2× Sample Buffer 50 µl 4×NuPAGE LDS Sample buffer (Invitrogen)+125 µl water and 25 µl 15% DTT. The mixture was heated 5 minutes at 95° C. and 20 µl was loaded on a 4-20% Tris-Glycine gel (NuPAGE 4-12%, MES buffer, Bis-Trin (Invitrogen)) and the gel was run at 200V, 100 mA for 35 minutes and developed using Comassie Blue stain. The protease was found to have a molecular weight of approximately 28 kDa.

The protease band was blotted to a PVDF membrane and the N-terminal sequence was determined using an Applied Biosystems Procise Protein Sequencer according to the manufacturer's instructions. The N-terminal sequence of the peptide from Bacillus sp. NN018132 was determined to be: MHNNQRW, corresponding to the amino acids in position 1-7 in SEQ ID NO: 2. Thus the N-terminal of the mature protease corresponds to position 1 of SEQ ID NO: 2.

The N-terminal sequence of the peptide from Bacillus bogoriensis was determined to be: MHNNQRW, corresponding to the amino acids in positions 1-7 in SEQ ID NO: 4. Thus the N-terminal of the mature protease corresponds to position 1 of SEQ ID NO: 4.

The N-terminal sequence of the peptide from Paenibacillus dendritiformis was determined to be: AIHNNQR, corresponding to the amino acids in positions 1-7 in SEQ ID NO: 6. Thus the N-terminal of the mature protease corresponds to position 1 of SEQ ID NO: 6.

Molecular Weight

The molecular weight was further determined using mass spectroscopy by LC-MS consisting using a Agilent 1100HPLC equipped with a Bruker microTOF focus mass analyzer. Samples were desalted using Bio Rad Micro Bi-Spinh 6 chromatography Column Cat no. 732-6221 following the manufacturer's instructions, and 70 µl was loaded on a Waters MassPREP On-Line Desalting 2.1×10 mm column, Part no. 186002785. The sample was eluted with a step elution of 80% Can 0.05% TFA.

LC-method Part: masspresLC10Min2061221TFA
A-solvent=0.05% TFA
B-solvent=Can, 0.05% TFA
MS acquisition Method Part: MassPresMS070529cmc
Data Path: 0711aESIMS
Mass analyzer calibrated with Tunemix fra Agilent.

The measured mass of Bacillus sp. NN018132 was 28116.3 Da (major peak), corresponding to amino acids 1-275 of SEQ ID NO: 2 (calculated to 28116.0 Da). Thus, the mature protein has the amino acid sequence corresponding to amino acids 1-275 of SEQ ID NO: 2.

The measured mass of Bacillus bogoriensis was 28341.2 Da (major peak), corresponding to the amino acids 1-275 of SEQ ID NO: 4 (calculated to 28341.1 Da). Thus, the mature protein has the amino acid sequence corresponding to amino acids 1-275 of SEQ ID NO: 4.

The measured mass of Paenibacillus dendritiformis was 28619.2 Da (major peak), corresponding to the amino acids 1-283 of SEQ ID NO: 6 (calculated to 28619.3 Da). Thus, the mature protein has the amino acid sequence corresponding to amino acids 1-283 of SEQ ID NO: 6.

Example 3

Low Temperature Mini Wash Assay

Wash performance of the protease prepared in Example 2 is assessed in laundry wash experiment using Mini wash assay, which is a test method, where soiled textile continuously is lifted up and down into the test solution and subsequently rinsed.

The experiments were conducted with two selected commercial detergents compositions: UL (Unilever) Persil Small & Mighty and Iconic Base. The performance was compared with the well know detergent protease Savinase (available from Novozymes A/S, Bagsvaerd, Denmark) (Bacilus lentus protease). The tests were conducted at 20° C. in order to evaluate the wash performance at low temperature.

The wash experiment is conducted under the experimental conditions specified in Tables 7 and 8 below:

TABLE 7

Detergent and test materials

| | |
|---|---|
| Detergent | Unilever Persil Small & Mighty non-bio |
| Detergent dose | 1.33 g/l |
| PH | "as is" in the current detergent solution and is not adjusted. |
| Water hardness | 15°dH, adjusted by adding $CaCl_2*2H_2O$, $MgCl_2*6H_2O$ and $NaHCO_3$ (4:1:7.5) to milli-Q water. |
| Enzymes | Savinase, Bacillus sp. NN018132 S8A protease |
| Enzyme conc. | 0 nM, 5 nM, 10 nM, 30 nM, 60 nM, 100 nM |
| Test solution volume | 50 ml |
| Test material | EMPA 117EH textile swatches (23 × 3 cm) PC-03 textile swatches C-10 textile swatches |
| Temperature | 20° C. |
| Wash time | 20 min |
| Rinse time | 10 min |
| Test system | Soiled textile continuously lifted up and down into the test solutions, 50 times per minute. The test solutions are kept in 125 ml glass beakers. After wash of the textiles are continuously lifted up and down into running tap water, 50 times per minute. |

TABLE 8

Detergent and test materials

| | |
|---|---|
| Detergent | Iconic Base |
| Detergent dose | 3.5 g/l |
| pH | "as is" in the current detergent solution and is not adjusted. |
| Water hardness | 15°dH, adjusted by adding $CaCl_2*2H_2O$, $MgCl_2*6H_2O$ and $NaHCO_3$ (4:1:7.5) to milli-Q water. |
| Enzymes | Savinase, *Bacillus* sp. NN018132 S8A protease |
| Enzyme conc. | 0 nM, 5 nM, 10 nM, 30 nM, 60 nM, 100 nM |
| Test solution volume | 50 ml |
| Test material | EMPA 117EH textile swatches (23 × 3 cm) <br> PC-03 textile swatches <br> C-10 textile swatches |
| Temperature | 20° C. |
| Wash time | 20 min |
| Rinse time | 10 min |
| Test system | Soiled textile is continuously washed by lifting up and down into the test solutions, 50 times per minute. The test solutions are kept in 125 ml glass beakers. After wash, the textiles are continuously rinsed by lifting up and down into running tap water, 50 times per minute. |

Test materials are obtained from EMPA Testmaterials AG Mövenstrasse 12, CH-9015 St, Gallen, Switzerland, from Center For Testmaterials BV, P.O. Box 120, 3133 KT Vlaardingen, the Netherlands.

The washed and rinsed soiled textiles are subsequently air-dried and the wash performance is measured as the brightness of the color of these textiles. Brightness can also be expressed as the Remission (R), which is a measure for the light reflected or emitted from the test material when illuminated with white light. The Remission (R) of the textiles is measured at 460 nm using a Zeiss MCS 521 VIS spectrophotometer. The measurements are done according to the manufacturer's protocol.

The Remission of the swatches; EMPA117EH, PC-03 and C-10, using Savinase or *Bacillus* sp. NN018132 S8A protease at various conc. in UL Persil Small & Mighty non-bio, 1.33 g/L, 15° dH, temperature 20° C., Miniwash, 20 min.

TABLE 9

Remission in UL Small and Mighty

| nM | EMPA117EH Savinase | EMPA117EH *Bacillus* sp. NN018132 S8A protease | PC-03 Savinase | PC-03 *Bacillus* sp. NN018132 S8A protease | C-10 Savinase | C-10 *Bacillus* sp. NN018132 S8A protease |
|---|---|---|---|---|---|---|
| 0 | 9.15 | 9.76 | 29.56 | 29.69 | 37.59 | 38.59 |
| 5 | 10.64 | 11.00 | 30.30 | 29.68 | 39.60 | 40.88 |
| 10 | 10.79 | 11.24 | 30.93 | 31.49 | 40.42 | 41.48 |
| 30 | 11.26 | 12.08 | 32.14 | 33.57 | 41.86 | 43.83 |
| 60 | 11.44 | 12.59 | 32.84 | 34.73 | 42.14 | 44.44 |
| 100 | 11.45 | 12.98 | 33.50 | 35.75 | 42.99 | 44.94 |

The Remission of the swatches; EMPA117EH, PC-03 and C-10, using Savinase or *Bacillus* sp. NN018132 S8A protease at various conc. in Iconic Base, 3.5 g/L, 15° dH, temperature 20° C. Miniwash, 20 min.

TABLE 10

Remission in Ionic base

| nM | EMPA117EH Savinase | EMPA117EH *Bacillus* sp. NN018132 S8A protease | PC-03 Savinase | PC-03 *Bacillus* sp. NN018132 S8A protease | C-10 Savinase | C-10 *Bacillus* sp. NN018132 S8A protease |
|---|---|---|---|---|---|---|
| 0 | 8.92 | 9.47 | 28.67 | 28.80 | 37.81 | 38.33 |
| 5 | 10.16 | 9.80 | 29.73 | 29.48 | 39.99 | 38.64 |
| 10 | 11.24 | 10.26 | 30.95 | 29.74 | 41.91 | 39.41 |
| 30 | 12.97 | 11.72 | 34.07 | 31.50 | 44.18 | 42.67 |
| 60 | 14.18 | 13.22 | 35.68 | 33.37 | 45.89 | 44.20 |
| 100 | 14.93 | 13.89 | 36.42 | 35.08 | 46.93 | 46.12 |

The protease of the invention shows good wash performance in the wash experiments and has on pair performance with the commercial protease Savinase at low temperature (20° C.) in one of the two tested detergent composition.

Example 4

Evaluation of the Stability of S8 Protease Bacillus sp. NN018132 in Liquid Detergent Using AMSA The stability of the S8 from Bacillus sp. NN018132 in detergent was tested by examining the wash performance of the detergent with protease using an Automatic Mechanical Stress Assay at 2 different wash temperatures. 3 different stability conditions were tested, which are:
the protease was added to the detergent composition immediately before wash;
the protease was pre-incubated with the detergent for 48 hours at 25° C.; and
the wash liquor was pre-incubated for 30 minutes at 40° C. before starting the wash.
The experiments were conducted as described in the Automatic Mechanical Stress Assay (AMSA) for laundry method using a single cycle wash procedure, with the detergent composition and swatches described in Table 1 and the experimental conditions as specified in Table 11 below.

TABLE 11

Experimental conditions for AMSA in Table 1

| Test solution | 8 g/L model detergent B |
|---|---|
| Test solution volume | 160 micro L |
| pH | As is |
| Wash time | 20 minutes |
| Temperature | 20° C. or 40° C. |
| Water hardness | 15°dH |
| Protease concentration | 0 (blank) or 30 nM |
| Swatch | PC-05 (blood/milk/ink) |

Water hardness was adjusted to 15° dH by addition of $CaCl_2$, $MgCl_2$, and $NaHCO_3$ ($Ca^{2+}$:$Mg^{2+}$:$CO_3^{2-}$=4:1:7.5) to the test system. After washing the textiles were flushed in tap water and dried.

TABLE 12

Delta intensity enzyme value of detergent containing S8 protease Bacillus sp. NN018132 or Savinase compared to detergent without protease on a PC-05 swatch.

| | Δ Wash performance at 20° C. | | | Δ Wash performance at 40° C. | | |
|---|---|---|---|---|---|---|
| | Fresh enzyme | ½-hr pre incubation at 40° C. | 48 hr in-detergent stability at 25° C. | Fresh enzyme | ½-hr pre incubation at 40° C. | 48 hr in-detergent stability at 25° C. |
| Bacillus sp. NN018132 | 90 | 46 | 83 | 76 | 7 | 72 |
| Savinase | 83 | 74 | 80 | 78 | 77 | 73 |

The results show that detergent containing S8 protease Bacillus sp. NN018132 has the same wash performance after 48 hours storage at 25° C. in liquid detergent as the fresh enzyme which is added to the detergent immediately prior to the wash. This shows that under these conditions the S8 protease Bacillus sp. NN018132 shows good detergent stability.

Moreover, the results show that detergent containing S8 protease Bacillus sp. NN018132 has the lost some wash performance after a 30 minute pre-incubation of the wash liquor at 40° C. when compared to the performance in wash liquor prepared with fresh enzyme added to the detergent immediately prior to the wash. This shows that under these conditions the S8 protease Bacillus sp. NN018132 shows good in-wash stability and that the enzyme has to work rapidly at the beginning of the wash cycle as fresh enzymes Savinase and Bacillus sp. NN018132 perform similar.

Example 5

AMSA Wash Performance of S8 Protease Bacillus sp. NN018132 in Different Water Hardness's and Protease Concentrations Using a Liquid Detergent The wash performance of S8 protease Bacillus sp. NN018132 was tested using a liquid detergent in 3 different water hardnesses and 2 different enzyme concentrations on 3 different technical stains using the Automatic Mechanical Stress Assay.

The experiments were conducted as described in the AMSA for laundry method using a single cycle wash procedure, with the detergent composition and swatches described in Table 1 and the experimental conditions as specified in Table 13 below.

TABLE 13

Experimental conditions for AMSA for Tables 14, 15 and 16

| Test solution | 2 g/L model detergent B |
|---|---|
| Test solution volume | 160 micro L |
| pH | As is |
| Wash time | 20 minutes |
| Temperature | 40° C. |
| Protease concentration | 0 (blank), 5 nM or 30 nM |
| Swatch | EMPA117EH, PC-03, C-10 |

Water hardness was adjusted to 6, 16 or 24° dH by addition of $CaCl_2$ and $MgCl_2$, ($Ca^{2+}$:$Mg^{2+}$=5:1) to the test system. After washing the textiles were flushed in tap water and dried.

TABLE 14

Delta intensity enzyme value of detergent containing
S8 protease Bacillus sp. NN018132 or Savinase compared to
detergent without protease on EMPA117EH swatches at 40° C.

| | Enzyme conc. | | | | | |
|---|---|---|---|---|---|---|
| | 5 nM | 5 nM | 5 nM | 30 nM | 30 nM | 30 nM |
| | | | Water hardness | | | |
| | 6°dH | 16°dH | 24°dH | 6°dH | 16°dH | 24°dH |
| Savinase | 1 | 4 | 16 | 22 | 21 | 50 |
| Bacillus sp. NN018132 | 32 | 27 | 30 | 68 | 61 | 57 |

The results show that the detergent containing S8 protease Bacillus sp. NN018132 is especially effective at removing blood/milk/ink on cotton/polyester stains in low to medium water hardnesses both compared to the detergent without protease and to the detergent containing Savinase.

TABLE 15

Delta intensity enzyme value of detergent containing
S8 protease Bacillus sp. NN018132 or Savinase compared to
detergent without protease on PC-03 swatches at 40° C.

| | Enzyme conc. | | | | | |
|---|---|---|---|---|---|---|
| | 5 nM | 5 nM | 5 nM | 30 nM | 30 nM | 30 nM |
| | | | Water hardness | | | |
| | 6°dH | 16°dH | 24°dH | 6°dH | 16°dH | 24°dH |
| Savinase | 3 | 5 | 13 | 14 | 18 | 19 |
| Bacillus sp. NN018132 | 20 | 16 | 21 | 38 | 36 | 41 |

The results show that the detergent containing S8 protease Bacillus sp. NN018132 is especially effective at removing chocolate-milk/ink on cotton/polyester stains in low to medium water hardnesses both compared to the detergent without protease and to the detergent containing Savinase.

TABLE 16

Delta intensity enzyme value of detergent containing
S8 protease Bacillus sp. NN018132 or Savinase compared to
detergent without protease on C-10 swatches at 40° C.

| | Enzyme conc. | | | | | |
|---|---|---|---|---|---|---|
| | 5 nM | 5 nM | 5 nM | 30 nM | 30 nM | 30 nM |
| | | | Water hardness | | | |
| | 6°dH | 16°dH | 24°dH | 6°dH | 16°dH | 24°dH |
| Savinase | 3 | 23 | 24 | 10 | 13 | 16 |
| Bacillus sp. NN018132 | 17 | 14 | 13 | 25 | 24 | 24 |

The results show that detergent containing S8 protease Bacillus sp. NN018132 is effective at removing oil/milk/pigment stains in low to medium water hardnesses both compared to the detergent without protease and to the detergent containing Savinase.

Example 6

AMSA Wash Performance of P. dendriti Using Two Different Liquid Detergents

The wash performance of S8 protease from P. dendriti was tested using a model liquid detergent and a commercial liquid detergent at 2 different wash temperatures on 2 different technical stains using the Automatic Mechanical Stress Assay.

The experiments were conducted as described in the AMSA for laundry method using a single cycle wash procedure, with the detergent composition and swatches described in Table 1 and the experimental conditions as specified in Table 17 below.

TABLE 17

Experimental conditions for AMSA for Table 18 below

| | |
|---|---|
| Test solution | 8 g/L liquid model detergent B and UL Persil Small&Mighty non-bio, 1.33 g/L |
| Test solution volume | 160 microL |
| pH | As is |
| Wash time | 20 minutes |
| Temperature | 20° C. or 40° C. |
| Water hardness | 15°dH |
| Protease concentration | 0 (blank) or 30 nM |
| Swatch | PC-05 (Blood/milk/ink) & PC-03 (Chocolate/milk/soot) |

Water hardness was adjusted to 15° dH by addition of $CaCl_2$, $MgCl_2$, and $NaHCO_3$ ($Ca^{2+}:Mg^{2+}:CO_3^{2-}=4:1:7.5$) to the test system. After washing the textiles were flushed in tap water and dried.

TABLE 18

Delta intensity value of detergent containing S8 protease from
P. dendriti compared to detergent without protease

| Swatch | Small and Mighty (1.33 g/L) at 20° C. | Detergent B (8 g/L) at 20° C. | Small and Mighty (1.33 g/L) at 40° C. | Detergent B (8 g/L) at 40° C. |
|---|---|---|---|---|
| PC-03 | 3 | 4 | 5 | 18 |
| PC-05 | 8 | 23 | 13 | 43 |

The results show that the detergent containing S8 protease from P. dendriti is more effective at removing stains compared to the detergent without any protease. S8 protease from P. dendriti is also effective at removing blood/milk/ink stains even at 20° C.

Example 7

AMSA Wash Performance of Bacillus Borgouniensis Using Two Different Liquid Detergents The wash performance of S8 protease from Bacillus borgouniensis was tested using a model liquid detergent and a commercial liquid detergent at 2 different wash temperatures on 2 different technical stains using the Automatic Mechanical Stress Assay.

The experiments were conducted as described in the AMSA for laundry method using a single cycle wash procedure, with the detergent composition and swatches described in Table 1 and the experimental conditions as specified in Table 19 below.

TABLE 19

Experimental conditions for AMSA for Table 20

| | |
|---|---|
| Test solution | 8 g/L liquid model detergent B and UL Persil Small&Mighty non-bio, 1.33 g/L |

TABLE 19-continued

Experimental conditions for AMSA for Table 20

| | |
|---|---|
| Test solution volume | 160 microL |
| pH | As is |
| Wash time | 20 minutes |
| Temperature | 20° C. or 40° C. |
| Water hardness | 15°dH |
| Protease concentration | 0 (blank) or 30 nM |
| Swatch | PC-05 (Blood/milk/ink) & PC-03 (Chocolate/milk/soot) |

Water hardness was adjusted to 15° dH by addition of $CaCl_2$, $MgCl_2$, and $NaHCO_3$ ($Ca^{2+}:Mg^{2+}:CO_3^{2-}=4:1:7.5$) to the test system. After washing the textiles were flushed in tap water and dried.

TABLE 20

Delta intensity value of detergent containing S8 protease from *Bacillus borgouniensis* compared to detergent without protease

| Swatch | Small and Mighty (1.33 g/L) at 20° C. | Detergent B (8 g/L) at 20° C. | Small and Mighty (1.33 g/L) at 40° C. | Detergent B (8 g/L) at 40° C. |
|---|---|---|---|---|
| PC-03 | 5 | 6 | 7 | 23 |
| PC-05 | 12 | 15 | 31 | 49 |

The results show that the detergent containing S8 protease from *Bacillus* borgouniensis is more effective at removing stains compared to the detergent without any protease. S8 protease from *Bacillus* borgouniensis is also effective at removing blood/milk/ink stains even at 20° C.

The invention claimed is:

1. A method of producing a polypeptide having protease activity, comprising cultivating a recombinant host cell under conditions conducive for production of the polypeptide, wherein
   (a) the recombinant host comprises a polynucleotide encoding the polypeptide,
   (b) the polypeptide has at least 95% sequence identity to amino acids 1-275 of SEQ ID NO: 2, and
   (c) the polynucleotide is operably linked to one or more control sequences that direct the production of the polypeptide in the recombinant host cell.

2. The method of claim 1, wherein the polypeptide has at least 97% sequence identity to amino acids 1-275 of SEQ ID NO: 2.

3. The method of claim 1, wherein the polypeptide is a fragment of amino acids 1-275 of SEQ ID NO: 2 and the fragment has protease activity.

4. A method of producing a polypeptide having protease activity comprising cultivating a recombinant host cell under conditions conducive for production of the polypeptide, wherein the polypeptide comprises amino acids 1-275 of SEQ ID NO: 2.

5. The method of claim 1, further comprising recovering the polypeptide.

6. The method of claim 2, further comprising recovering the polypeptide.

7. The method of claim 3, further comprising recovering the polypeptide.

8. The method of claim 4, further comprising recovering the polypeptide.

9. The method of claim 1, wherein the recombinant host is a *Bacillus* recombinant host cell.

10. The method of claim 2, wherein the recombinant host is a *Bacillus* recombinant host cell.

11. The method of claim 3, wherein the recombinant host is a *Bacillus* recombinant host cell.

12. The method of claim 4, wherein the recombinant host is a *Bacillus* recombinant host cell.

13. The method of claim 9, wherein the *Bacillus* recombinant host cell is a host cell selected from the group consisting of *Bacillus amyloliquefaciens, Bacillus licheniformis*, and *Bacillus subtilis*.

14. The method of claim 10, wherein the *Bacillus* recombinant host cell is a host cell selected from the group consisting of *Bacillus amyloliquefaciens, Bacillus licheniformis*, and *Bacillus subtilis*.

15. The method of claim 11, wherein the *Bacillus* recombinant host cell is a host cell selected from the group consisting of *Bacillus amyloliquefaciens, Bacillus licheniformis*, and *Bacillus subtilis*.

16. The method of claim 12, wherein the *Bacillus* recombinant host cell is a host cell selected from the group consisting of *Bacillus amyloliquefaciens, Bacillus licheniformis*, and *Bacillus subtilis*.

17. A method of producing a polypeptide having protease activity, comprising cultivating a recombinant host cell under conditions conducive for production of the polypeptide, wherein
   (a) the recombinant host comprises a polynucleotide encoding the polypeptide,
   (b) the polypeptide comprises a catalytic domain which has at least 95% sequence identity to amino acids 7-270 of SEQ ID NO: 2, and
   (c) the polynucleotide is operably linked to one or more control sequences that direct the production of the polypeptide in the recombinant host cell.

18. The method of claim 17, wherein the catalytic domain has at least 97% sequence identity to amino acids 7-270 of SEQ ID NO: 2.

19. The method of claim 17, wherein the catalytic domain comprises amino acids 7-270 of SEQ ID NO: 2.

20. The method of claim 17, wherein the recombinant host is a *Bacillus* recombinant host cell.

* * * * *